US012799153B2

(12) United States Patent
Kupryushkin et al.

(10) Patent No.: US 12,799,153 B2

(45) Date of Patent: Nov. 17, 2026

(54) CHEMICAL COMPOUND COMPRISING A TRIAZINE GROUP AND METHOD FOR PRODUCING SAME

(71) Applicant: Maxim Sergeevich Kupryushkin, Novosibirsk (RU)

(72) Inventors: Maxim Sergeevich Kupryushkin, Novosibirsk (RU); Timofei Dmitrievich Zharkov, Novosibirsk (RU); Ilya Sergeevich Dovydenko, Berdsk (RU); Oleg Vladimirovich Markov, Novosibirsk (RU)

(73) Assignee: Maxim Sergeevich Kupryushkin, Novosibirsk (RU)

( * ) Notice: Subject to any disclaimer, the term of this patent is extended or adjusted under 35 U.S.C. 154(b) by 0 days.

(21) Appl. No.: 18/031,420

(22) PCT Filed: Oct. 13, 2021

(86) PCT No.: PCT/RU2021/050339

§ 371 (c)(1),
(2) Date: Apr. 12, 2023

(87) PCT Pub. No.: WO2022/081046

PCT Pub. Date: Apr. 21, 2022

(65) Prior Publication Data

US 2026/0085087 A1 Mar. 26, 2026

(30) Foreign Application Priority Data

Oct. 12, 2020 (RU) ................................ 2020133433

(51) Int. Cl.

*C07H 21/00* (2006.01)
*A61K 31/7125* (2006.01)
*A61P 35/00* (2006.01)

(52) U.S. Cl.

CPC ......... *C07H 21/00* (2013.01); *A61K 31/7125* (2013.01); *A61P 35/00* (2018.01)

(58) Field of Classification Search

None

See application file for complete search history.

(56) References Cited

FOREIGN PATENT DOCUMENTS

RU 2708237 C2 * 12/2019 ................ A61P 3/06

* cited by examiner

*Primary Examiner* — Dale R Miller

(74) *Attorney, Agent, or Firm* — Patentbar International

(57) ABSTRACT

A chemical compound having a triazine group and a method for production thereof are related to novel compounds and methods for production thereof in nucleotide chemistry. In particular, the present invention relates to nucleotides and oligonucleotides comprising a modified phosphate group, and to the method for production thereof. The present invention may be used in cytological studies, in DNA- or RNA-containing pathogen diagnostics, in gene therapy as well as in treating various bacterial and viral diseases, including COVID-19. The objective of the present invention is to provide compounds having a therapeutic potential as well as to develop the available method for production thereof.

24 Claims, 6 Drawing Sheets

Specification includes a Sequence Listing.

OSN4F, * :

PGO, * :

PN, * :

ODF, [D] :

CHEMICAL COMPOUND COMPRISING A TRIAZINE GROUP AND METHOD FOR PRODUCING SAME

CROSS-REFERENCE TO RELATED APPLICATIONS

This Application is a US national stage application of International Application PCT/RU2021/050339 filed on Oct. 13, 2021, which in turn claims priority to Russian patent application RU 2020133433 filed on Oct. 12, 2020, both of which are incorporated herein by reference in their entirety.

FIELD OF THE INVENTION

The present invention relates to novel compounds and methods for production thereof in nucleotide chemistry. In particular, the present invention relates to nucleotides and oligonucleotides comprising a modified phosphate group, and to the method for production thereof. The present invention may be used in cytological studies, in DNA- or RNA-containing pathogen diagnostics, in gene therapy as well as in treating various bacterial and viral diseases, including COVID-19.

BACKGROUND OF THE INVENTION

Nucleic acid (NA) derivatives such as synthetic oligonucleotides modified by various additional functionalities are widely used as research tools in various areas of molecular biology, biotechnology, and medical science. The use of oligonucleotides as therapeutic agents is one of the most promising areas: over 11 drugs have been approved by the Food & Drug Administration (FDA, the USA), and over 150 drugs are currently at different phases of clinical trials. For example, oligonucleotide drugs, such as anti-angiogenic aptamer Macugene (Pegaptanib sodium), Exondys 51 (eteplirsen) and Vyondys 53 (golodirsen), drugs intended for treating Duchenne muscular dystrophy, Spinraza (nusinersen) intended for treating spinal muscular atrophy, etc. (https://www.fda.gov/drugs/development-approval-process-drugs/drug-approvals-and-atabases) have received approval for clinical use.

Many oligonucleotide drugs are directed at treating diseases caused by mutations in one or more genes in the patient. Therefore, these drugs are targeted at correction of expression of the genes responsible for the disease.

Oligonucleotides can inhibit transcription, translation, or modulate the target gene product activity. Transcription is inhibited through binding DNA by triplex-forming oligonucleotides [1], including peptide nucleic acids (PNAs) [2]. Translation is inhibited, or antisense mechanism is implemented by blocking translation using specific mRNA [3]. Activity of a protein coded by a target gene is modulated by oligonucleotide binding with the protein itself or with a low molecular weight cofactor, e.g., in the case of aptamers [4].

Most known oligonucleotides function through the antisense mechanism by binding with a specific mRNA in a cell; however, the principle and conditions of translation inhibition differ for various oligonucleotide types. For example, small interfering RNAs (siRNAs) cause catalytic splitting of specific matrix RNA (mRNA) by forming an NA-protein complex RISC having a nuclease activity. Therefore, siRNA interaction with the target mRNA results in degradation of the latter by preventing mRNA translation on ribosomes into the protein coded by it [5].

NA enzymes, which are catalytic nucleic acids being oligonucleotides with a typical secondary structure, also cause mRNA splitting. However, NA enzymes as RNA hydrolytic splitting catalysts do not need cell proteins [6].

Most antisense oligonucleotide analogs bind to mRNA and suppress translation by functioning as per the steric blocking principle [7]. They include many oligonucleotide analogs with a modified ribose moiety: 2'-fluoro [8], 2'-O-methyl [9], 2'-O-β-methoxyethyl (2'-MOE) [10], LNA [11]. Analogs with an uncharged internucleotide phosphate group: methylphosphonates [12], phosphotriesters [13] and phosphoramides [14] also function as per the steric blocking principle.

The similar mechanism is also effective in the case of NA derivatives where both ribose and phosphate moieties are concomitantly modified, such as peptide nucleic acids (PNAs) [15] and phosphorodiamidate morpholino oligonucleotides (PMO) [16].

Oligonucleotide drugs are also developed and used for treating diseases caused by viruses such as human cytomegalovirus (HCMV), HIV (HIV-1), hepatitis B (HBV), hepatitis C (HCV), Ebola virus, respiratory syncytial virus (RSV), SARS-CoV coronavirus causing severe acute respiratory syndrome (SARS), etc. [17-24].

Development of the therapy using antisense oligonucleotides is a promising area for controlling SARS-CoV-2 coronavirus causing COVID-19. In particular, antisense oligonucleotides complementary to a FSE (frameshift stimulation element), a highly conservative portion of SARS-CoV-2 genome are being developed [25]. The use of oligonucleotides for controlling SARS-CoV-2 coronavirus is especially relevant due to the difficulties related to production of efficient vaccine because of high mutation rate of genes coding virus envelope proteins.

Independently of the mode of action, compounds suitable for drug development, in particular, oligonucleotides, should have a therapeutic potential. The therapeutic potential is intended to mean a wide range of useful properties required to achieve the marked therapeutic effect. In particular, therapeutic oligonucleotides should have the following properties:

a. Improved cell penetration, preferably in the absence of transfection agents;

Improved penetration ensures the achievement of a biological target and the need to use lower dosages in using the respective drugs.

b. Low cell toxicity;

Low toxicity allows using the respective drugs in a wide range of concentrations to obtain the best therapeutic effects, without harmful effects for the body.

c. High stability in biological environments;

High stability allows the drug to stay longer in the body to obtain the required therapeutic effect with minimum drug administrations. Moreover, high stability in biological environments provides diverse drug administration routes.

d. Capability to form strong and specific complexes with a biological target;

Capability to form strong complexes with a biological target provides the required level of exposure process irreversibility to obtain the therapeutic effect. In this case, the specificity of formation of the respective complexes provides the absence of exposure to other biological targets while minimizing side effects to the body.

e. Production availability.

A compound production method may be considered available if it is compatible with the existing and widely used synthesis protocols in various technical fields.

The process aspects related to the development of the respective compound classes exist. For example, leading an oligonucleotide agent all the way through to an effective drug will be significantly limited when using a non-flexible, expensive, or all too specific, i.e. poorly compatible with commonly used, production method. For example, currently the phosphoramidite method is the most efficient and widely used oligonucleotide synthesis method. Phosphoramidite protocols using automated DNA/RNA synthesizers are known to those skilled in the art of nucleotide chemistry. Automated nucleic acid and their derivatives synthesis is a demanded and rapidly emerging area of chemistry, which is permanently supplemented by new, including commercially available, components for oligonucleotide synthesis, such as various nucleoside and non-nucleoside monomers, various modifiers, in particular, fluorescent tags and fluorescence quenchers, as well as different protecting groups.

Therefore, when producing an oligonucleotide having a therapeutic potential, the compatibility of the production method with the existing synthesis protocols in the phosphoramidite chemistry is one of the most crucial factors providing a competitive advantage in the oligonucleotide drug development.

Having at least one of the aforementioned beneficial properties allows regarding the compound as the one having a therapeutic potential. The more of the aforementioned beneficial properties are combined in a particular compound class, and the higher the demonstration level of such properties, the higher the therapeutic potential of the compound class and the more promising it is for the therapeutic drug development.

Although natural oligonucleotides are capable of forming selective complementary complexes with biological targets, while not being a toxic compound class for the body, they are not sufficiently stable in biological environments and poorly penetrate the cells. To improve the aforementioned parameters, various chemical modifications are introduced to oligonucleotides. Introduction of various chemical modifications to oligonucleotides, in particular, allows improving its penetration efficiency through the cellular membrane, resistance to enzymatic hydrolysis, stability in a broad range of pH, specificity, and stability of a complex formed with a complementary portion of the target nucleic acid, while preserving low toxicity for the body [26].

Oligonucleotide contains several modification positions: nucleobases, a ribose moiety, and an internucleotide phosphate group.

The internucleotide phosphate group modification is beneficial compared to other positions in terms of introduction of non-natural chemical groups. Modifications introduced through the phosphate group of the backbone have minor effects on a fundamental oligonucleotide property, i.e. their ability to form strong and specific complexes with biological targets. At the same time, introduction of various groups may impart new properties to the developed compound in a broad range.

Various variants of modifications made to the internucleotide phosphate groups are known, such as methylphosphonates [27], thiophosphates [28, 29], dithiophosphates [30], boranophosphates [31](WO1991008213A1, publ. Jun. 13, 1991; IPC A61K31/69, A61K31/70, A61K31/7135, A61P29/00, A61P3/06, A61P35/00, C07H21/00, C07H21/04, C07H23/00, C12N15/113, C12Q1/68), phosphoramidates, phosphoryl guanidines, etc.

Methylphosphonate oligonucleotides have a high resistance to enzymatic hydrolysis with nucleases as well as slightly increased degree of formation of a complementary complex. At the same time, methylphosphonate oligonucleotides are chemically unstable and are easily alkaline-hydrolyzed. Furthermore, methods other than phosphoramidite synthesis are used to produce methylphosphonate oligonucleotides, which reduces their production efficiency and precludes manufacturers from using a wide range of commercially available monomers and modifiers. The need to use special monomers significantly reduces the ability to use methylphosphonate oligonucleotides as a platform for developing therapeutic drugs [32, 33].

Boranophosphate oligonucleotides have an enhanced enzymatic and chemical stability. Unlike methylphosphonate modifications, boranophosphate modifications do not result in the disappearance of a negative charge of the phosphonate group. As a result, boranophosphate oligonucleotides can recruit RNAse to split the hybrid DNA/RNA complex. Such mechanism of exposure on a target, as opposed to simple steric blocking, allows the therapeutic agent to operate in a catalytic mode. However, complementary complexes thus formed with such modified oligonucleotides are less stable than natural oligonucleotides. Moreover, methods for producing boranophosphate oligonucleotides are also incompatible with the phosphoramidite synthesis and also require preparation of a set of special monomers [34, 35].

Phosphoramidate oligonucleotides contain N-substituted amino group instead of oxygen within the phosphate group. Due to neutralization of the negative charge of the phosphate group, phosphoramidate oligonucleotides are more resistant to nucleases. Substituents at amino group may be a source of various functionalities for the developed oligonucleotide. However, the main drawback of phosphoramidates that limits their application is their susceptibility to acidic hydrolysis due to amino group protonation [36-38].

Thiophosphate oligonucleotides are one of few compound classes which found their use in therapeutic NA development. Thiophosphate oligonucleotides are stable to cellular nucleases, and their synthesis is compatible with the protocols of solid-phase phosphoramidite oligonucleotide synthesis. However, this modification type does not involve any versatility in incorporated groups, except for replacing oxygen to sulphur. Therefore, property modification within this class may only be achieved by varying the amount and incorporation point of thiophosphate units. Moreover, thiophosphate oligonucleotides have a relatively high toxicity and somewhat reduced capability to form complexes with NAs compared to unmodified oligonucleotides. These drawbacks probably limit wide application of this compound class as therapeutic drugs [39].

Dithiophosphate oligonucleotides can activate RNAse N, although with a lower efficiency than thiophosphate oligonucleotides. At the same time, dithiophosphate oligonucleotides are even more resistant to nucleases. However, due to increased sulphur content, dithiophosphate oligonucleotides are less specific in inhibiting translation because of stronger protein binding. Furthermore, their chemical synthesis is even more complicated than that of thiophosphates.

Phosphate group-modified oligonucleotides may also include morpholino oligonucleotides wherein the entire ribose-phosphate backbone is replaced with morpholinophosphoramidate backbone. Such backbone is nowhere near natural, which prevents interaction between morpholino oligonucleotides and any NA-dependent enzymes, including RNAse N. Morpholino oligonucleotides are stable to nucleases and can form rather strong complementary complexes with NAs. However, this compound class contains only one representative, which makes it very difficult to vary properties of morpholino oligonucleotides. Moreover, morpholino oligonucleotide production requires special equipment, monomers, and reagents. The employed morpholino oligonucleotide production methods are incompatible with the standard phosphoramidite synthesis [16,40,41].

Note that aforementioned modifications except for thiophosphates and morpholino oligonucleotides, though they have been known for a long time, are not used in the therapeutic oligonucleotide development. This is often because of a low degree of compatibility of their production methods with the standard phosphoramidite synthesis method.

Recent class of phosphoryl guanidine oligonucleotides is also a compound class containing modification through internucleotide phosphate group (RU2708237C2, publ. Dec. 5, 2019; IPC: A61K31/712, A61P31/12, C07F9/24, C07H19/10, C07H19/20). In this case, this is a moiety of the substituted or unsubstituted guanidine that makes the produced phosphoryl guanidine group electroneutral. The representatives of this oligonucleotide class are stable to cellular nucleases and are resistant in a wide range of pH. Furthermore, upon incorporation of a sufficiently large amount of such modifications to the developed oligonucleotide, preferably at all internucleotide phosphate groups, we can achieve minor improvements in cell penetration. However, upon incorporation of many modifications to an oligonucleotide, its backbone becomes very different from the natural ribose-phosphate backbone. As a result, such modified oligonucleotides lose their ability to interact with NA-dependent enzymes, in particular with RNAse N, which strongly limits the available therapeutic mechanisms of this compound class.

Therefore, there is a need to provide compounds having a high therapeutic potential which are produced by an available, readily scalable method.

TERMS AND DEFINITIONS

Alkyl refers to a branched or linear cyclic or acyclic substituent based on saturated hydrocarbons with a free valence at carbon. For example, $C_{1-4}$ alkyls include, but not limited to, methyl, ethyl, n-propyl, i-propyl, or t-butyl radicals.

Alkenyl refers to a branched or linear acyclic substituent with a free valence at carbon based on unsaturated hydrocarbons containing at least one double C—C bond, which may or may not comprise triple C—C bonds.

Alkynyl refers to a branched or linear acyclic substituent with a free valence at carbon based on unsaturated hydrocarbons containing at least one triple C—C bond. In addition, alkynyl may or may not comprise double C—C bonds.

Aryl refers to an aromatic or heteroaromatic organic group with a free valence at carbon or, in some embodiments, at heteroatom. Examples of aromatic groups may include, but not limited to, phenyl and naphthyl (1-naphthyl or 2-naphthyl). Aryl groups may be monocyclic or polycyclic.

Protecting group refers to a chemical group used to temporarily block a reaction site in an organic compound and can be removed in particular conditions.

Linker refers to a non-nucleotide chemical group that may link adjacent nucleotides in an oligonucleotide (an internucleotide linker); or link nucleotide or its analog with another non-nucleotide group; or link oligonucleotide or its analog with a polymer support; or link nucleoside or its analog with a polymer support.

Nucleoside refers to a chemical compound containing a sugar moiety and a heterocyclic base moiety. Exemplary nucleosides may include, but not limited to, ribose, 2-deoxyribose, arabinose, etc. Exemplary heterocyclic bases may include, but not limited to, thymine, uracil, cytosine, adenine, guanine, purine, hypoxanthine, xanthine, 2-aminopurine, 2,6-diaminopurine, 5-methylcytosine, 5-fluorouracil, 5-choloruracil, 5-bromouracil, 5-iodouracil, 5-trifluoromethyl uracil, 5-fluorocytosine, 5-chlorocytosie, 5-bromocytosine, 5-iodocytosine, 2-thiouracil, 4-thiouracil, 2-thiothymine, 4-thiothymine, 5-propynyl uracil, 5-propynyl cytosine, 7-deazaadenine, 7-deazaguanine, 7-deaza-8-azaadenine, 7-deaza-8-deazaguanine, isocytosine, isoguanine, etc.

Nucleoside may also refer to a protected nucleoside, nucleoside analog, and protected nucleoside analog.

Nucleoside analog is used to designate a modified nucleoside wherein the sugar moiety is replaced with another cyclic or acyclic structure. Exemplary nucleoside analogs wherein the sugar moiety is replaced with another cyclic structure may include, but not limited to, monomers of morpholino oligonucleotides (PMO) and tricyclo-DNA. Exemplary nucleoside analogs wherein the sugar moiety is replaced with another acyclic structure may include, but not limited to, monomers of peptide nucleic acids (PNAs) and glycerol nucleic acids (GNAs). Furthermore, nucleoside analog is used to designate a nucleoside containing a chemical modification, e.g. a substituent in the sugar moiety and/or in the heterocyclic base. Examples of such nucleoside analogs may include, but not limited to, 2'-substituted 2'-deoxynucleosides, such as 2'-amino and 2'-fluoro, and ribonucleosides, such as 2'-O-methyl, 2'-O-allyl, 2'-O-β-methoxyethyl ribonucleosides, "locked" nucleosides (LNAs), etc.

Among others, nucleoside analogs may include analogs wherein the sugar moiety is replaced with a morpholine ring, as shown in the following Formula:

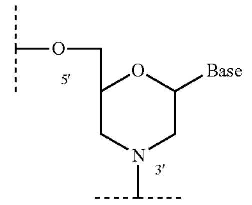

wherein Base is a heterocyclic base.

Structures of this type use designations of 3' and 5' similarly to natural nucleosides. In particular, in the above structure, hydroxymethyl substituent in the morpholine ring corresponds to the 5'-end, while the third valence of nitrogen corresponds to the 3'-end of nucleoside.

Protected nucleoside refers to a nucleoside comprising one or more protecting groups. Nucleoside analog can also be protected. For example, DMTr-nucleoside contains the DMTr protecting group at its 5'-end.

Nucleotide refers to a chemical compound containing a nucleoside and at least one phosphate group covalently bonded to it. Example of covalent bond is, independently and not limited to, an ester bond between 3'-, 2'- or 5'-hydroxyl group of the nucleoside and the phosphate group.

Nucleotide may also refer to a nucleotide analog.

Nucleotide analog refers to a chemical compound containing a nucleoside analog and at least one phosphate group covalently bonded to it. Exemplary nucleotide analogs with the replaced sugar moiety may include, but not limited to, 2'-substituted 2'-deoxynucleotides, such as 2'-amino and 2'-fluoro, and ribonucleotides, such as 2-O-methyl, 2-O-allyl, 2'-O-β-methoxyethyl ribonucleotides, "locked" nucleotides (LNAs), morpholino nucleotides, tricyclo-deoxyribonucleotides, glycol nucleotides.

Oligonucleotide refers to a chemical compound consisting of two or more nucleotides interconnected to form a polymer chain. Oligonucleotide may be a DNA or RNA fragment. Oligonucleotides may be single-stranded or double-stranded, i.e. they may contain two strands with a high complementarity degree. In this case, any strand or both strands may be modified according to the present invention. A key feature of oligonucleotide is its capability to form stable duplexes with complementary NA portions and derivatives thereof via non-covalent bond. Hydrogen bond may represent such non-covalent bond.

Oligonucleotide may also refer to oligonucleotide analog or modified oligonucleotide containing modification that is beyond the scope of this invention.

Oligonucleotide analog refers to an oligonucleotide variant that includes at least one nucleotide analog, and wherein the total amount of nucleotides and/or nucleotide analogs is two or more. Specifically, oligonucleotide analog may be entirely composed of nucleotide analogs. Moreover, oligonucleotide analog may include at least one phosphate group that may be modified according to the present invention.

Oligonucleotide analogs may contain, e.g. chemical groupings at 3'- and/or 5'-end of oligonucleotide (e.g. 3'-"inverted" nucleoside moiety), moieties of a high molecular weight compound of low immunogenicity (e.g. polyethylene glycol), low molecular weight compounds (e.g. cholesterol), peptides (e.g. peptides improving cell penetration), phosphate groups with modifications beyond the scope of this invention (e.g. thiophosphate group). Oligonucleotide analogs may also contain modified heterocyclic bases. For example, chemical modification of heterocyclic bases may include, but not limited to, substitution at C-5 of pyrimidine nucleotide, substitution at C-7 of 7-deazapurine nucleotide, substitution at exocyclic amino group, incorporation of 4-thiouracil, 5-bromo- and/or 5-iodouracil moieties, etc. Oligonucleotide analogs may also contain modified sugar moieties. For example, modification of the sugar moiety may also include incorporation of 2'-aminonucleotide, 2'-fluoronucleotide, 2'-O-methyl ribonucleotide, 2'-O-allyl ribonucleotide, 2'-O-β-methoxyethyl ribonucleotide, "locked" nucleotide (locked nucleic acid, LNA), and/or tricyclo-DNA nucleotide. Furthermore, in oligonucleotide analogs, links between the central phosphorus in the phosphate group may be arranged, but not limited to, through oxygen (common phosphate), nitrogen (N3'-P5' phosphoramide), or sulphur (3'-thiophosphate); respectively, 3'- and/or 5'-end of nucleoside may terminate in, but not limited to, hydroxyl group, like in a natural nucleoside, 3'-amine group (N3'-P5' phosphoramide), or 3'-mercapto group (3'-thiophosphate). Exemplary oligonucleotide analogs may also include, but not limited to, thiophosphates (PS), selenophosphates, dithiophosphates, phosphoramides, boranophosphates, phosphorodiamidate morpholino oligonucleotides (PMO), tricyclo-DNA, phosphoryl guanidine oligonucleotides (PGO), and peptide nucleic acids (PNA). In PNAs, phosphate groups are replaced by peptide links. However, there are PNA variants, which include phosphate groups that may be modified according to the present invention.

Protected oligonucleotide refers to an oligonucleotide containing one or more protecting groups.

Phosphate group refers to a phosphoric acid $H_3PO_4$residue wherein one or more hydrogens are substituted with an organic radical to give, respectively, phosphomonoester, phosphodiester, or phosphotriester. Phosphate group may also refer to a modified phosphate group.

Modified phosphate group refers to a phosphate group wherein any oxygen is substituted with any chemical group. Exemplary substituents may be, but not limited to, sulphurs, seleniums, imine group (—NHR), borane moiety ($—BH_3^-$), substituted or unsubstituted guanidine moiety. The preferred examples of the modified phosphate group are thiophosphate group, phosphoramide group, phosphoryl guanidine group.

Final de-blocking refers to removal of protecting groups and splitting of oligonucleotide or analog thereof from a solid-phase support (if oligonucleotide or its analog production method is implemented in a solid-phase variant).

Therapeutic oligonucleotide refers to an oligonucleotide or oligonucleotide analog having a therapeutic potential, with the length of 5 to 1,000 nucleotides, used in a drug for therapy of cancer, genomic disorders, and infectious diseases of various nature, e.g. as ASO for translation inhibiting (siRNA, microRNA), to modulate splicing by exon skipping, to correct genotype using the CRISPR/Cas method, and as aptamers for specific inhibition of target proteins or directed drug transport.

ABBREVIATIONS AND DESIGNATIONS

- HIV means human immunodeficiency virus
- DNA means deoxyribonucleic acid
- NA means nucleic acid (DNA or RNA)
- RP-HPLC means reverse-phase high-performance liquid chromatography
- RNA means ribonucleic acid
- ASO means antisense oligonucleotide
- DMF means dimethylformamide
- DMTr means 4,4'-dimethoxytrityl group
- FAM means 6-carboxyfluorescein
- FBS means fetal bovine serum
- HEK293T means Human Embryonic Kidney 293, a cell line derived from human embryonic kidneys
- HepG2 means a cell line derived from human hepatocellular carcinoma
- IMDM means Iscove's modified Dulbecco's medium, a medium for culturing mammalian cells; DMEM modification (Dulbecco's modified Eagle's medium) comprising sodium selenite, additional amino acids and vitamins, sodium pyruvate, HEPES (4-(2-hydroxyethyl)-1-piperazineethanesulfonic acid), and potassium nitrate instead of iron nitrate.
- LNA means locked nucleic acid
- IU means international unit, a unit of measurement of a substance dose based on its biological activity. Substance amounts in 1 IU differ for different classes. Activity units, AU, are often the same as IU.
- MEM means minimum essential medium, Eagle's medium; a medium for culturing cell cultures, contains a buffer solution to maintain optimal pH of 7.4, glucose, amino acids, vitamins, and other substances.
- mQ means deionized water, Type I water (ultra-pure water)
- Opti-MEM means medium for culturing cell cultures; it is a modification of minimum DMEM recommended for transfection.
- PBS means phosphate buffered saline, isotonic sodium phosphate buffer which is a water solution of salts containing sodium chloride, sodium hydrophosphate, potassium chloride, and potassium dihydrophosphate. Osmolarity and ion concentrations in the solution approximately match concentrations in the human body.

PG means protecting group.

PMO means phosphorodiamidate morpholino oligomer.

PNA means peptide nucleic acid. Term "peptide nucleic acids" usually refers to oligonucleotide analogs wherein phosphate groups are replaced by peptide bonds. However, the term "peptide nucleic acids" may also include compounds containing modified phosphate groups being the subject matter of this invention. Therefore, such compounds may also be within the scope of the present invention.

siRNA means small interfering RNA

T98G means a cell line derived from human glioblastoma

THF means tetrahydrofuran

Ts means tosyl

*: in the Examples, means a position of the claimed modification within oligonucleotide d: in the Examples, means a position of dodecyl phosphoramidate group within oligonucleotide.

SUMMARY OF THE INVENTION

The objective of the present invention is to provide compounds having a therapeutic potential as well as to develop the available method for production thereof.

The objective is attained by the claimed invention through achieving the technical result such as to provide compounds including oligonucleotides which may have one or more of the following properties:

a. improved cell penetration, preferably in the absence of transfection agents;

b. low cell toxicity;

c. high chemical and enzymatic stability;

d. capability to form strong and specific complexes with a biological target.

Also, an important part of the technical result is the ability to provide the claimed compounds using an available method (e), i.e. the method compatible with the existing common synthesis methods.

The claimed technical result is achieved by that the claimed invention includes compounds of Formula F0:

(F0)

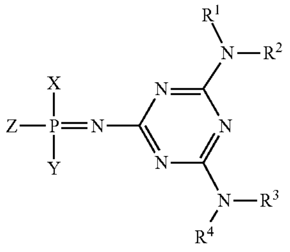

Wherein substituent Z is selected from the group of: —OH, —SH, —SeH, —$NHR^N$, —O—PG, —S—PG, —Se—PG, or —$N(PG)R^N$.

In an embodiment, X is selected from the group consisting of the 5'-O end of a nucleoside or oligonucleotide, and Y is selected from the group consisting of the 3'-O end of a nucleoside or oligonucleotide, —H, —OH, —SH, —$NHR^N$, —O—PG, or —S—PG, a linker, a monophosphate, or a diphosphate.

In another embodiment, Y is selected from the group consisting of the 5'-O end of a nucleoside or oligonucleotide, and X is selected from the group consisting of the 3'-O end of a nucleoside or oligonucleotide, —H, —OH, —SH, —$NHR^N$, —O—PG, or —S—PG, a linker, a monophosphate, or a diphosphate.

Substituents $R^1$, $R^2$, $R^3$, $R^4$ are selected from the series of —H, —$C_{1-18}$alkyl, —$C_{2-18}$alkenyl, —$C_{2-18}$alkynyl, and —$C_{6-18}$aryl, which may include various lipophilic and/or cationic groups.

By using various substituents $R^1$, $R^2$, $R^3$ and $R^4$ within triazine group, lipophilicity and charge of the claimed compounds may be widely varied. Biodistribution parameters in the body, in particular, ability to penetrate a particular type of cells may be thus modulated. This may be used in the development of targeted therapeutic drugs.

Triazine moiety imparts chemical and enzymatic stability to the claimed compounds. Moreover, phosphate group modified according to the present invention is electroneutral, which improves the ability of the claimed compounds to penetrate the cell membrane. These properties are typical of all claimed compounds independently of substituents within the triazine moiety.

The subject matter of the present invention may be an oligonucleotide including at least one modified phosphate group of Formula Fx:

(Fx)

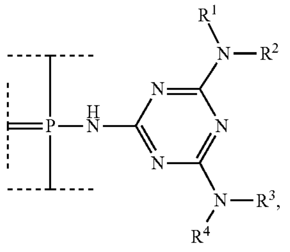

wherein ---- indicates attachment of substituents corresponding to oligonucleotide.

The presence of at least one claimed modification may improve therapeutic potential of the developed compound, in particular, the ability of oligonucleotide to penetrate cell membranes. This allows developing modified oligonucleotides with the desired efficiency and cell penetration specificity with a minimum degree of oligonucleotide modification. Providing minimum modifications simplifies the production of the claimed oligonucleotide significantly, and the resulting compound backbone maintains its ability to interact with cell enzymes. Of no less importance is the fact that the claimed modification does not weaken the modified oligonucleotides' ability to form specific complexes with the complementary portions of NAs or derivatives thereof.

The subject matter of the present invention also includes the method for production of the compound of Formula (F0). The method involves interaction of a trivalent phosphorus derivative of Formula (F1) with an azidotriazine of Formula (F2) to give a compound of Formula (F3), with subsequent processing with amines $HNR^1R^2$, $HNR^3R^4$, or $HNR^XR^Y$. Wherein substituents $R^X$ and $R^Y$ will be converted to substituents $R^1$, $R^2$, $R^3$, $R^4$ using conversion reactions known in the art for the respective reactive groups included in $R^X$ and $R^Y$.

(F1)

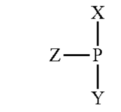

(F2)

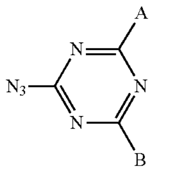

(F3)

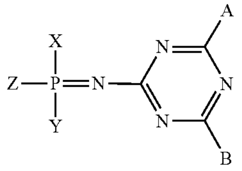

Substituents X, Y, Z are defined as in Formula (F0).

A and B may be independently selected from the series of —$NR^1R^2$, —$NR^3R^4$, —$NR^XR^Y$, -Q.

Substituents $R^1$, $R^2$, $R^3$, $R^4$, R as described in claim 1 are defined as in Formula (F0).

Q is a group capable of taking part in the replacement reactions. Q is selected from the series of: —OR, —OC(O)R, —$OS(O)_2R$, —CN, —Cl, —Br, —I, —F, —$N_3$. The Q group may be substituted with —$NR^1R^2$, —$NR^3R^4$, —$NR^XR^Y$ in a reaction with the respective amine $HNR^1R^2$, $HNR^3R^4$, $HNR^XR^Y$. Substituents $R^X$, $R^Y$ are selected from the series comprising —H, —$C_{1-18}$alkyl, —$C_{2-18}$alkenyl, —$C_{2-18}$alkynyl, and —$C_{6-18}$aryl, which may include the groups of —NH—, —N<, —O—, —NHC(O)—, —$NHS(O)_2$—, and/or —$N(CH_2CH_2)_2N$—, and terminate in the groups of —$NR_2$, —OR, —SR, —OC(O)R, —NHC(O)R, —C(O)OR, —C(O)NHR, —$N{=}C(N(R_2))_2$, —S(O)R, —$S(O)_2R$, —$S(O)_2NR_2$, —CN, —Cl, —Br, —I, —F, —$N_3$.

Wherein R is a substituent is selected from the series of —H, —$C_{1-18}$alkyl, —$C_{2-18}$alkenyl, —$C_{2-18}$alkynl and —$C_{6-18}$aryl, which may include the groups of —NH—, —N<, —O—, —NHC(O)—, —$NHS(O)_2$—, and/or —$N(CH_2CH_2)_2N$—, and terminate in the groups of —$NR^N_2$, —$OR^N$, —$SR^N$, —$OC(O)R^N$, —$NHC(O)R^N$, —$C(O)OR^N$, —$C(O)NHR^N$, —$N{=}C(N(R_2))_2$, —S(O)R, —$S(O)_2R$, —$S(O)_2NR_2$, —CN, —Cl, —Br, —I, —F, —$N_3$. Wherein substituents $R^1$, $R^2$, $R^3$, $R^4$ are as defined in Formula (F0).

In an embodiment of the method, A=—$NR^1R^2$, B=—$NR^3R^4$. In this case, the production of the compound of Formula (F0) does not require additional chemical transformations.

In another embodiment of the method, A=B=-Q. In yet another embodiment of the method, A=—$NR^1R^2$, B=-Q. In both cases, where one or both substituents A and B are -Q, the Q group is replaced by —$NR^1R^2$, —$NR^3R^4$, —$NR^XR^Y$ in a reaction with the respective amine $HNR^1R^2$, $HNR^3R^4$, $HNR^XR^Y$. Substitution may be performed both within the compound of Formula (F2) and within the compound of Formula (F3).

Substituents $R^X$ and $R^Y$ contain reactive centers which are further subjected to chemical transformation or a series of chemical transformations to bring structures of substituents $R^X$ and $R^Y$ to structures of $R^1$, $R^2$, $R^3$, $R^4$. Wherein $R^X$, $R^Y$ to $R^1$, $R^2$, $R^3$ or $R^4$ may be converted both within the compound of Formula (F2) and within the compound of Formula (F3).

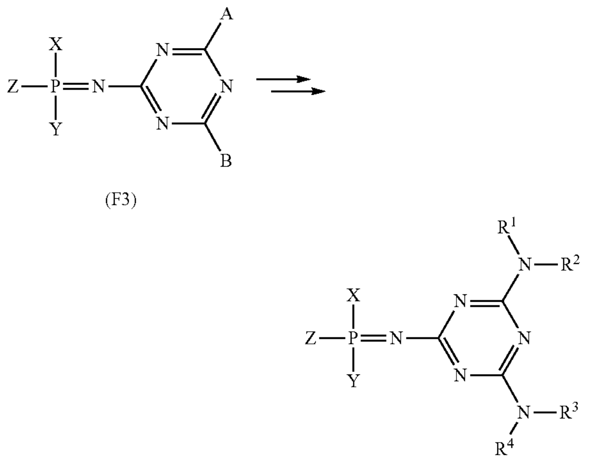

(F3)

(F0)

Substituents $R^1$, $R^2$, $R^3$, $R^4$, $R^X$ and $R^Y$ may be widely defined using the respective commercial and individually synthesized amines $HNR^1R^2$, $HNR^3R^4$, and $HNR^XR^Y$, which provides for the flexibility of the selected production method and variability of the produced compound class of general Formula (F0). Wherein $R^X$ and $R^Y$ may be converted to $R^1$, $R^2$, $R^3$ or $R^4$ in several consecutive steps. This multistep nature of $R^X$ and $R^Y$ transformations also provides the ability to produce a wide range of the claimed compounds without complicating the method.

In an embodiment of the method related to the oligonucleotide production, a derivative of trivalent phosphorus is represented by an H-phosphonate unit produced using the H-phosphonate oligonucleotide synthesis method, or a phosphite unit produced according to the phosphoramidite method of oligonucleotide synthesis.

At that, the method for production of modified oligonucleotides according to the present invention may be implemented in a liquid phase variant wherein all reagents in all reactions are present in solutions. In a preferred embodiment, the claimed method is implemented in a solid-phase variant wherein the oligonucleotide to be synthesized is immobilized on a solid-phase support. Polymer support may be used as a solid-phase support.

In a preferred embodiment, all phosphoramidite units are condensed automatically using a DNA synthesizer. At that, the triazine group may be incorporated into any internucleotide phosphate group of the oligonucleotide to be synthesized.

According to the present invention, one or more internucleotide phosphate groups within oligonucleotide may be modified. In an embodiment, all internucleotide phosphate groups within oligonucleotide may be modified. However, in a preferred embodiment, oligonucleotide contains one or two modified internucleotide phosphate groups.

An advantage of the claimed method is that it can be combined with the standard protocol of phosphoramidite synthesis, which dramatically simplifies and lowers the cost of production of modified oligonucleotides.

Equally important advantage of the claimed method is a high variability of the produced compounds, which is provided by a hierarchic sequence of steps for producing a target compound.

The present invention may be used in cytological research, in molecular diagnostics, in anti-cancer therapeutic drugs development and development of the drugs to treat genomic disorders, various diseases of bacterial and viral nature, including COVID-19. In particular, oligonucleotides modified according to the present invention may be used in techniques such as, e.g. alternative splicing, antisense microRNA and siRNA therapy, the use of aptamers, genome editing using CRISPR/Cas, and others.

DETAILED DESCRIPTION OF THE INVENTION

Figure 1:
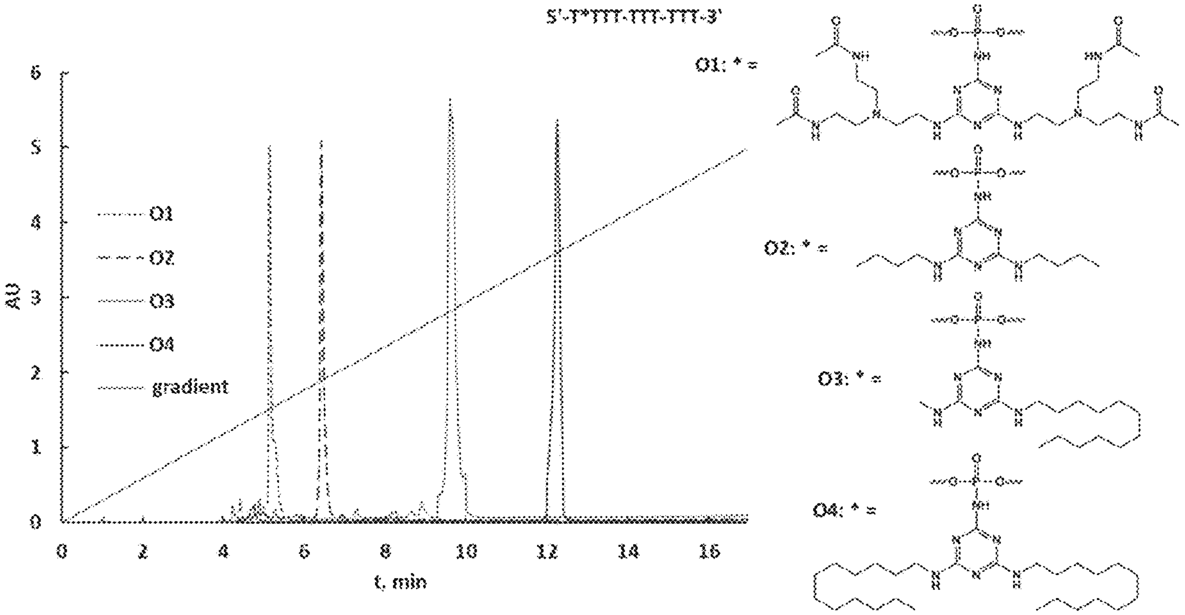
FIG. 1 shows examples of chromatography (RP-HPLC) of the produced compounds.

The following detailed invention embodiment disclosure provides numerous implementation details intended to ensure a clear understanding of this invention. However, it is known by a person skilled in the art how this invention can be used both with or without these implementation details. In other aspect, well-known methods, procedures, and components are not described in details so that not to impede understanding of the features of this invention.

Moreover, it is evident from the disclosure that the invention is not limited by the provided embodiment. Numerous possible modifications, changes, variations, and replacements keeping the essence and spirit of this invention are evident for those skilled in the art.

The present invention relates to the compounds of Formula F0:

(F0)

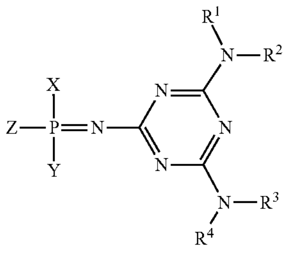

Wherein substituent Z is selected from the group of: —OH, —SH, —SeH, —$NHR^N$, —O—PG, —S—PG, —Se—PG, or —N(PG)$R^N$.

In an embodiment, X is selected from the group consisting of the 5'-O end of a nucleoside or oligonucleotide, and Y is selected from the group consisting of the 3'-O end of a nucleoside or oligonucleotide, —H, —OH, —SH, —$NHR^N$, —O—PG, or —S—PG, a linker, a monophosphate, or a diphosphate.

In another embodiment, Y is selected from the group consisting of the 5'-O end of a nucleoside or oligonucleotide, and X is selected from the group consisting of the 3'-O end of a nucleoside or oligonucleotide, —H, —OH, —SH, —$NHR^N$, —O—PG, or —S—PG, a linker, a monophosphate, or a diphosphate.

Exemplary protecting groups (PG) may include, but not limited to, acetyl (Ac), benzoyl (Bz), isobutyryl (Ibu), m-butyl phenoxyacetyl (Tac), levulinyl (Lev), methyl (Me), β-cyanoethyl (CE), allyl (All), o-chlorophenyl (o-CiPh), 4,4'-dimethoxytrityl (DMTr), 4-methoxytrityl (MMTr), m-butyldimethylsilyl (MMTr), m-butyldimethylsilyl (TBDMS), triisopropylsilyloxymethyl (TOM), and other groups.

Exemplary linkers may include, but not limited to, succinyl, diglycolyl, oxalyl, hydroquinone-O,O'-diacetyl (Q linker), phthaloyl, 4,5-dichlorophthaloyl, malonyl, glutaryl, diisopropylsilyl, 1,1,3,3-tetraisopropyldisiloxane-1,3-diilyl, BHQ linker, amino linker, and other linkers.

Substituents $R^1$, $R^2$, $R^3$, $R^4$ are selected from the series of —H, —$C_{1-18}$alkyl, —$C_{2-18}$alkenyl, —$C_{2-18}$alkynyl, and —$C_{6-18}$aryl, which may include the groups of —NH—, —N<, —O—, —NHC(O)—, —$NHS(O)_2$—, —$N(CH_2CH_2)_2N$—, and/or

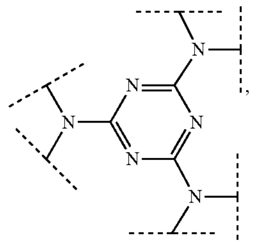

and terminate in —$NR_2$, —OR, —SR, —OC(O)R, —NHC(O)R, —C(O)OR, —C(O)NHR, —N=C(N($R_2$)$_2$, —S(O)R, —$S(O)_2R$, —$S(O)_2NR_2$, —CN, —Cl, —Br, —I, —F, —$N_3$,

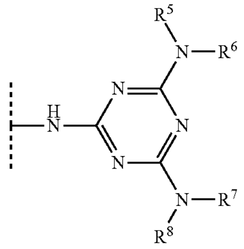 or 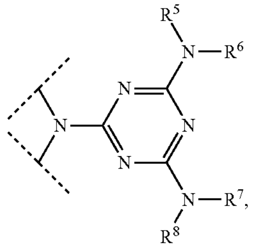

Substituents $R^5$, $R^6$, $R^7$, $R^8$ are selected from the series comprising —H, —$C_{1-18}$alkyl, —$C_{2-18}$alkenyl, —$C_{2-18}$alkynyl, and —$C_{6-18}$aryl, which may include the groups of —NH—, —N<, —O—, —NHC(O)—, —$NHS(O)_2$—, and/or —$N(CH_2CH_2)_2N$—, and terminate in —$NR_2$, —OR, —SR, —OC(O)R, —NHC(O)R, —C(O)OR, —C(O)NHR, —N═C(N($R_2$))$_2$, —S(O)R, —S(O)$_2$R, —S(O)$_2$N$R_2$, —CN, —Cl, —Br, —I, —F, —$N_3$.

Wherein R is a substituent selected from the series of —H, —$C_{1-18}$alkyl, —$C_{2-18}$alkenyl, —$C_{2-18}$alkynyl, and —$C_{6-18}$aryl, which may include the groups of —NH—, —N<, —O—, —NHC(O)—, —NHS(O)$_2$—, and/or —N($CH_2CH_2$)$_2$N—, and terminate in —N$R^N_2$, —O$R^N$, —S$R^N$, —OC(O)$R^N$, —NHC(O)$R^N$, —C(O)O$R^N$, —C(O) NH$R^N$, —N═C(N($R_2$))$_2$, —S(O)R, —S(O)$_2$R, —S(O)$_2$ N$R_2$, —CN, —Cl, —Br, —I, —F, —$N_3$.

Wherein PG is a protecting group, and $R^N$ is —H or —$C_{1-4}$alkyl.

In some embodiments, substituents $R^1$ and $R^2$; $R^3$ and $R^4$; $R^5$ and $R^6$; $R^7$ and $R^8$ together with the atom to which they are bound form a 5-8-membered heterocyclic substituent selected from the group consisting of N-pyrrolidinyl, N-piperidinyl, N-azepanyl, N-azocanyl, or N-piperazinyl.

In the claimed compounds, the introduced triazine moiety imparts chemical and enzymatic stability. Moreover, a phosphate group modified according to the present invention is electroneutral unlike negatively charged unmodified phosphate group, which improves the ability of the claimed compound to penetrate the cell membrane. These properties are typical of the entire class of the disclosed compounds independently of substituents within the triazine moiety.

By using various substituents $R^1$, $R^2$, $R^3$ and $R^4$ within the triazine group, lipophilicity and charge of the compound to be produced may be widely varied, and, respectively, modulate the ability of the claimed compound to biodistributed in the body, in particular, penetrate cells, depending on the cellular membrane composition of a particular cell type. This may be used in the development of therapeutic drugs which should specifically penetrate only the particular cell type.

Note that the presence of at least one claimed modification may improve therapeutic potential of the developed compound, in particular, the ability of oligonucleotide to penetrate cell membranes. This allows developing modified oligonucleotides with the desired efficiency and cell penetration specificity with a minimum degree of oligonucleotide modification. Providing minimum modifications significantly simplifies the production process for the claimed oligonucleotide.

Furthermore, providing minimum modifications, in a preferred embodiment, a single modification localized at the 3-end or 5'-end of oligonucleotide changes the entire structure of the ribose-phosphate backbone of the oligonucleotide to a minimum extent. This maintains interaction of the modified oligonucleotide with NA enzymes, in particular, RNAse N.

Of no less importance is the fact that the claimed modification insignificantly affect the modified oligonucleotides' ability to form specific complexes with complementary portions of NA targets. This is explained by that the triazine group in the complementary complex and substituents attached thereto, upon formation of complexes with the complementary DNA or RNA portions are exposed outwardly from the double helix and thus affect complementary interaction of nucleobases inside of it.

Depending on substituents, the modified phosphate group may be chiral. If the stereochemical configuration is not designated, the structure includes both Rp and Sp configurations, individually or as a mixture, e.g. a racemic mixture (racemate). For example, the structure:

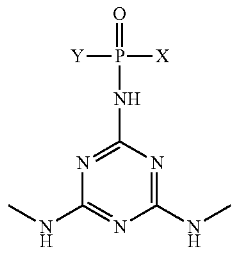

includes the following structures as shown below:

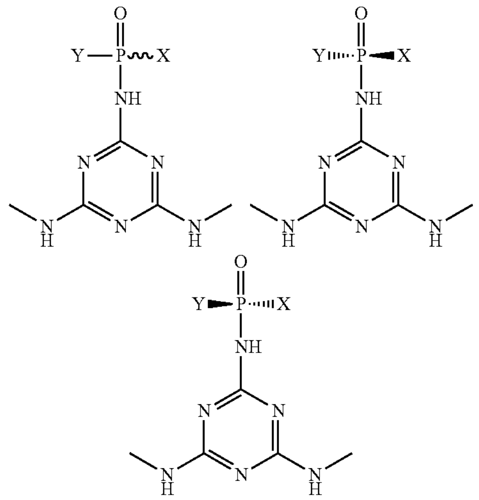

The claimed compounds may also include more than one chiral center. In such case, it is considered that the structure covers all possible enantiomers and diastereomers.

In a particular case, where Z substituent is —OH, Formula F0 may be provided in two tautomeric forms:

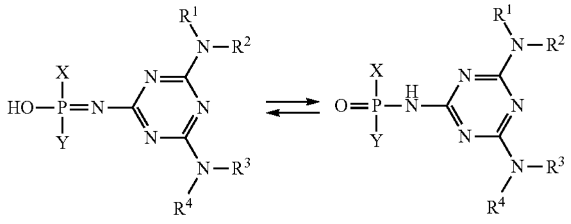

The subject matter of the present invention may be an oligonucleotide comprising at least one modified phosphate group of Formula (Fx):

(Fx)

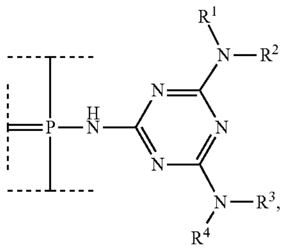

wherein ---- indicates an attachment of substituents corresponding to the oligonucleotide, and $R^1$, $R^2$, $R^3$ and $R^4$ are as defined in Formula (F0).

Formula (Fx) represents the structure of the oligonucleotide modified according to the present invention after the final deblocking step.

Oligonucleotides according to the present invention may consist of any number of nucleotides, at least 2. For example, oligonucleotide may have a minimum length of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. Optionally, oligonucleotide may have a maximum length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 nucleotides, although longer oligonucleotides may be used in particular applications. By way of example only, oligonucleotide consisting of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides may be produced.

In oligonucleotides being the subject matter of the present invention, one or more, e.g. 2, 3, 4, 5, 6, 7, 8, 9, 10 or more nucleotides, or all nucleotides, may contain a phosphate group modified according to the present invention. In a preferred embodiment, oligonucleotide comprises not more than two claimed modifications. In a more preferred embodiment, oligonucleotide comprises one claimed modification.

Oligonucleotides of 5 to 500 nucleotides long as modified according to the present invention, may be used in cancer therapy, in therapy of genomic disorders and infectious diseases, e.g. as ASO for suppressing translation (siRNA, microRNA), to modulate splicing by exone skipping, to correct genotype using the CRISPR/Cas method, and as aptamers for specific inhibition of target proteins or targeted drug transport, as well as in another applications. The length of the modified oligonucleotide is 5-500 nucleotides, on the one hand, provides the specificity of the complex that forms oligonucleotide with a complementary NA portion. On the other hand, the said length allows producing a modified oligonucleotide by using an automated DNA synthesizer.

Oligonucleotides within the scope of the present invention may be produced and isolated in pure form.

A part of preferred compounds covered by the present invention are represented by formulas as shown below:

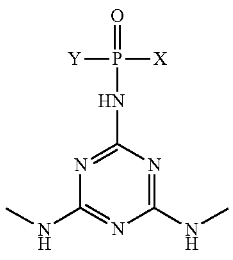

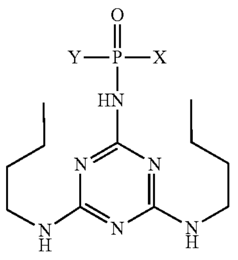

-continued

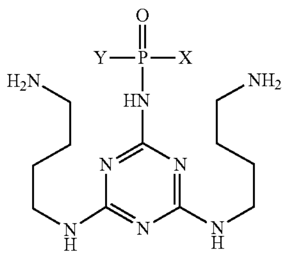

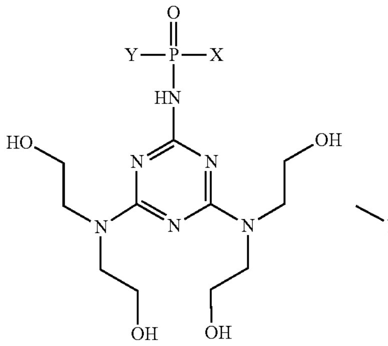

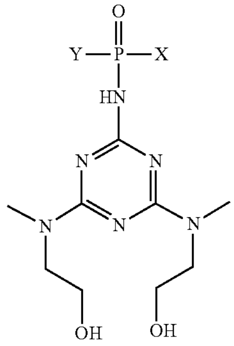

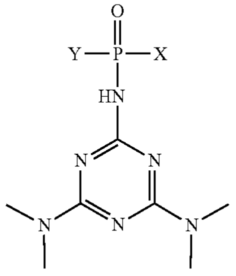

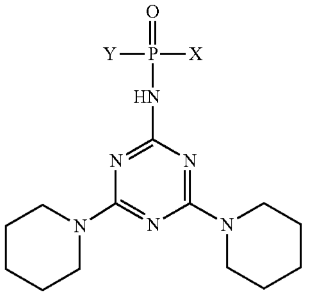

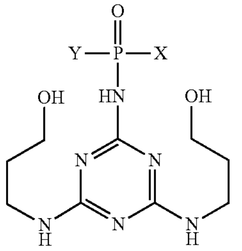

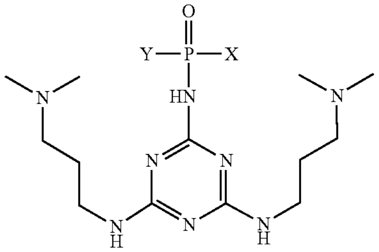

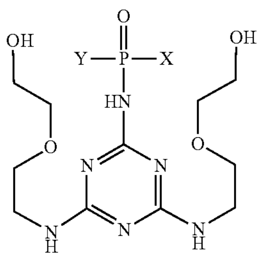

-continued
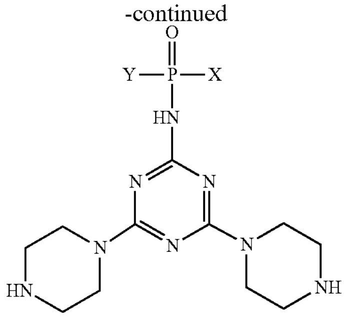
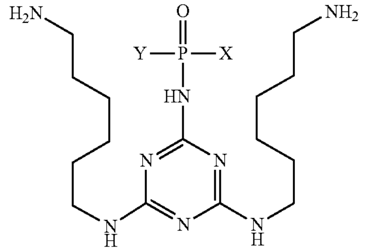
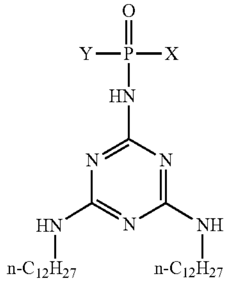
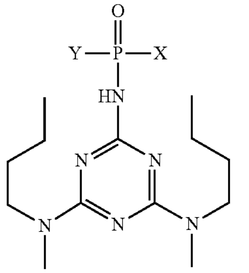
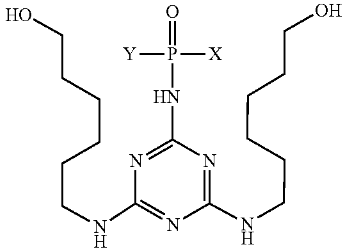
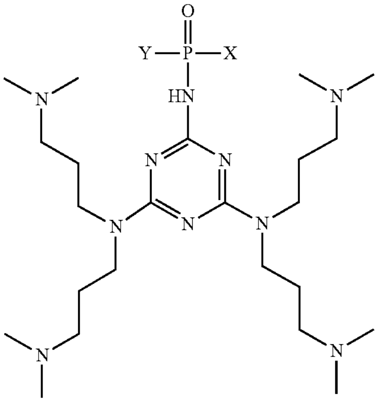
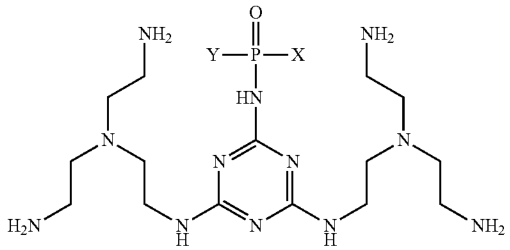
-continued
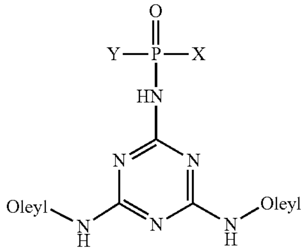
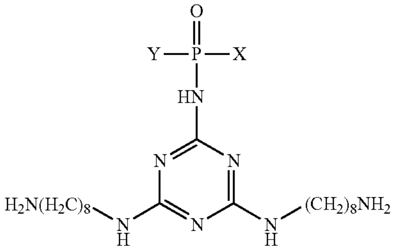
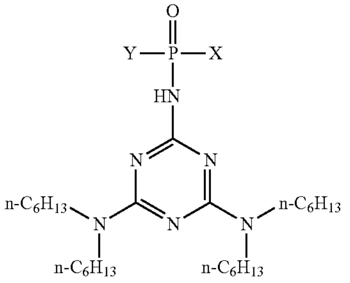
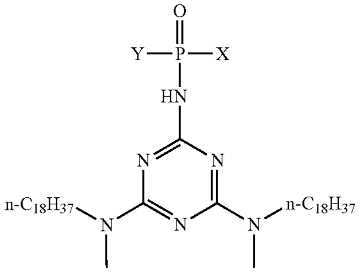
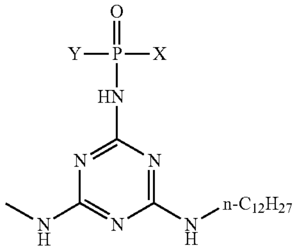
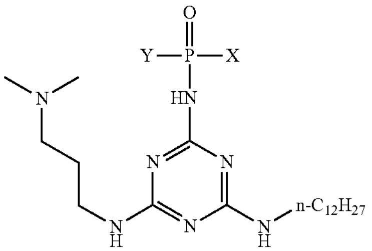

-continued

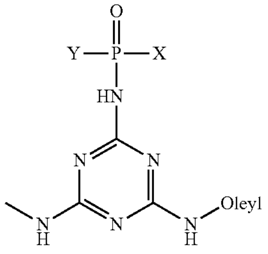

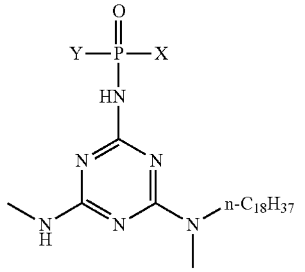

Method for Production of Claimed Compound

The method for production of claimed compounds of Formula (F0) involves interaction of the trivalent phosphorus derivative of Formula (F1) with azidotriazine of Formula (F2) to give compounds of Formula (F3) as shown in the scheme.

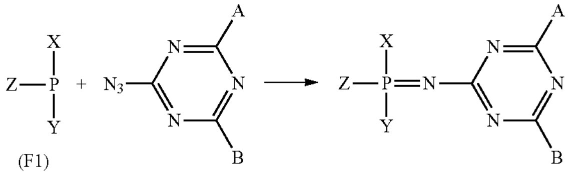

(F1) (F2) (F3)

Substituents X, Y, Z are defined as in Formula (F0).

A and B may be independently selected from the series of $—NR^1R^2$, $—NR^3R^4$, $—NR^XR^Y$, -Q.

Substituents $R^1$, $R^2$, $R^3$, $R^4$ are as defined in Formula (F0).

Q is a group capable of taking part in the replacement reactions. Q may be, e.g. —OR; —OC(O)R; $—OS(O)_2R$; —CN; —Cl; —Br; —I; —F; $—N_3$. According to the claimed method, Q is substituted with $—NR^1R^2$, $—NR^3R^4$, $—NR^XR^Y$ in a reaction with the respective amine $HNR^1R^2$, $HNR^3R^4$, $HNR^XR^Y$. Wherein substitution may be performed both in the used azidotriazine (F2) and in the compound (F3).

The use of azidotriazine (F2) to oxidize the trivalent phosphorus derivative (F1) provides several technical advantages. First, because of the acceptor nature of the triazine group, azidotriazines are much more reactive compounds than azides with more electron-donor substituents, such as, e.g. alkyl azides. Second, structural features of the used azidotriazine allow introducing two functionalities (A and B) at once to the produced compound within one phosphate group, which, in most cases, allows imparting the desired property to the produced compound by using a single modification.

$R^X$ and $R^Y$ are substituents containing lipophilic and/or cationic groups, and they also contain reactive centers which will be further subjected to a chemical transformation or a series of chemical transformations to bring substituent structures to the structures of $R^1$, $R^2$, $R^3$ or $R^4$. Wherein $R^X$, $R^Y_B$ $R^1$, $R^2$, $R^3$ or $R^4$ may be converted both in the compound (F2) and in the compound (F3).

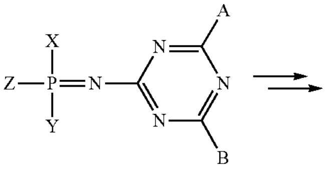

(F3)

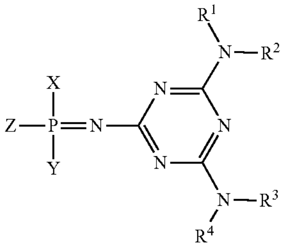

(F0)

Substituents $R^1$, $R^2$, $R^3$, $R^4$, $R^X$ and $R^Y$ may be widely defined by using the respective commercial and individually synthesized amines $HNR^1R^2$, $HNR^3R^4$, and $HNR^XR^Y$, which provides flexibility of the claimed production method and diversity of representatives of the produced compound class having general Formula (F0).

Substituents $R^X$, $R^Y$ are selected from the series comprising —H, $—C_{1-8}$alkyl, $—C_{2-18}$alkenyl, $—C_{2-18}$alkynyl, and $—C_{6-18}$aryl, which may include groups —NH—, —N<, —O—, —NHC(O)—, $—NHS(O)_2—$, and/or $—N(CH_2CH_2)_2N—$, and terminate in $—NR_2$, —OR, —SR, —OC(O)R, —NHC(O)R, —C(O)OR, —C(O)NHR, $—N{=}C(N(R_2))_2$, —S(O)R, $—S(O)_2R$, $—S(O)_2NR_2$, —CN, —Cl, —Br, —I, —F, $—N_3$.

In specific embodiments, $R^X$, $R^Y$, or $R^1$, $R^2$, $R^3$, $R^4$ are defined by amines as provided below:

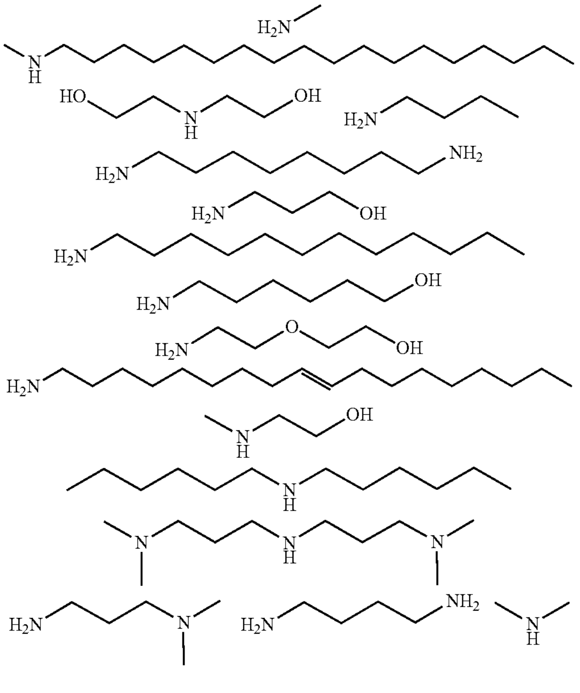

-continued

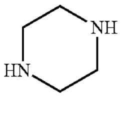

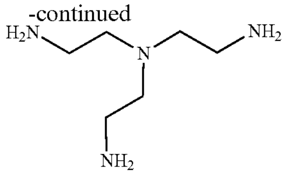

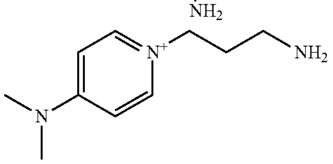

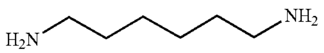

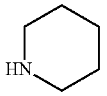

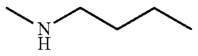

The present functionalities, such as $NH_2$, —OH, —NH—, within substituents $R^X$, $R^Y$ may be converted to other functionalities using simple organic synthesis reactions known by those skilled in the art.

In particular, if $R^X$, $R^Y$ contain group —$NH_2$, the group may be converted, e.g., to —$NR^{X1}{}_2$ in a reaction with $QR^{X1}$; or to —$NHR^{X1}$ in a reaction with $TsOR^{X1}$; or to —NHC(O)$R^{X1}$ in a reaction with $QC(O)R^{X1}$; or to —$NHS(O)_2R^{X1}$ in a reaction with $QS(O)_2R^{X1}$; or to —N═$C(N(R^N{}_2))_2$ in a reaction with $[QC^+(NR^N{}_2)_2]E^-$; or to

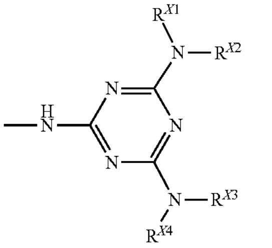

in sequential reactions with

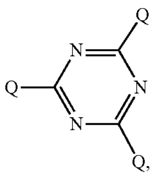 or 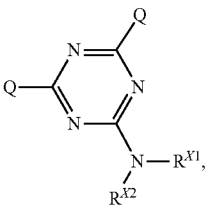 or

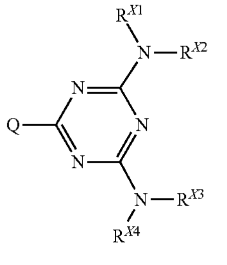

and amines $NHR^{X1}R^{X2}$ and $NHR^{X3}R^{X4}$.

If $R^X$, $R^Y$ contain group —OH, the group may be converted, e.g., to —$OR^{X1}$ in a reaction with $R^{X1}$; or to —$NHR^{X1}$ in sequential reactions with QTs and amine $NH_2R^{X1}$; or to nucleotide or oligonucleotide after automated synthesis, wherein group —OH is a growth point for the oligonucleotide chain.

Wherein $R^{X1}$, $R^{X2}$, $R^{X3}$, $R^{X4}$ are selected from the series comprising —H, —$C_{1-18}$alkyl, —$C_{2-18}$alkenyl, —$C_{2-18}$ alkynyl, and —$C_{6-18}$aryl, which may include the groups of —NH—, —N<, —O—, —NHC(O)—, —$NHS(O)_2$—, and/or —$N(CH_2CH_2)_2N$—, and terminate in —$NR_2$, —OR, —SR, —OC(O)R, —NHC(O)R, —C(O)OR, —C(O)NHR, —N═$C(N(R_2))_2$, —S(O)R, —$S(O)_2R$, —$S(O)_2NR_2$, —CN, —Cl, —Br, —I, —F, —$N_3$.

If $R^{X1}$, $R^{X2}$, $R^{X3}$, $R^{X4}$ comprise group —$NH_2$, the group may be converted to —$NR_2$ in a reaction with QR; or to —NHR in a reaction with TsOR; or to —NHC(O)R in a reaction with QC(O)R; or to —$NHS(O)_2R$ in a reaction with $QS(O)_2R$; or to —N═$C(N(R^N{}_2))_2$ in a reaction with $[QC^+(NR^N{}_2)_2]E^-$; or to

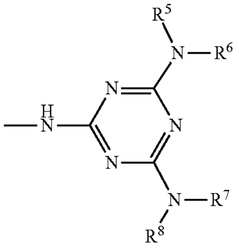

in sequential reactions with

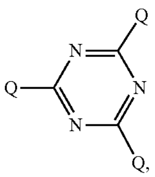 or 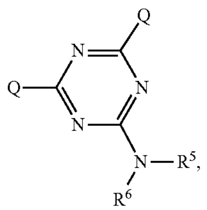 or

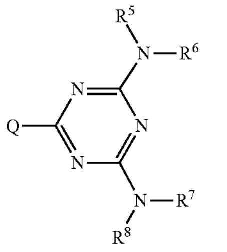

and amines $NHR^5R^6$ and $NHR^7R^8$.

If $R^{X1}$, $R^{X2}$, $R^{X3}$, $R^{X4}$ terminate in —OH, the group may be converted to —OR in a reaction with QR; or to —NHR in consequential reactions with QTs and amine $NH_2R$; or to a nucleotide or oligonucleotide sequence after the automated synthesis is continued.

Wherein substituents $R^5$, $R^6$, $R^7$, $R^8$, R, $R^N$ are as described in (F0).

Wherein $E^-$ is an anionic component selected from the group comprising $I^-$, $Br^-$, $Cl^-$, succinimide ($(CH_2)_2(CO)_2N^-$), $CCl_3^-$, $CBr_3^-$, $CI_3^-$, $CHI_2^-$, trifluoromethanesulfonate ($CF_3SO_3^-$), p-toluenesulhpnate ($C_7H_7SO_3^-$), dichlorophosphate ($PO_2Cl_2^-$), perchlorate ($ClO_4^-$), tetrafluoroborate ($BF_4^-$), tetraphenylborate ($BPh_4^-$), or hexafluorophosphate ($PF_6^-$).

In specific embodiments, in the case of presence in $R^X$, $R^Y$ of primary or secondary amine groups (—$NH_2$, —NH—), modified groups terminating in the moieties selected from the series of tosyl, acetyl, substituted or unsubstituted guanidine moiety, 4,6-dichloro-1,3,5-triazine moiety, may be produced. In the case of selection of 4,6-dichloro-1,3,5-triazine as a terminal residue, its further modification using amines $NHR^{X1}R^{X2}$ selected from the series of methylamine, butylamine, piperazine, etc. may be possible.

In specific embodiments, in the case of presence in $R^X$, $R^Y$ of hydroxyl groups —OH, these groups may be converted to other derivatives in a reaction with the respective nucleophilic reagents. In particular, hydroxyl groups may be converted to ether, ester moieties, and be a growth point for a new oligonucleotide sequence. In the case of substitution with the tosyl moiety, its further modification using amines $NHR^{X1}R^{X2}$ may be possible to give the respective moieties of secondary and primary amines.

Some examples of chemical transformations of groups —$NH_2$ and —OH are as provided below:

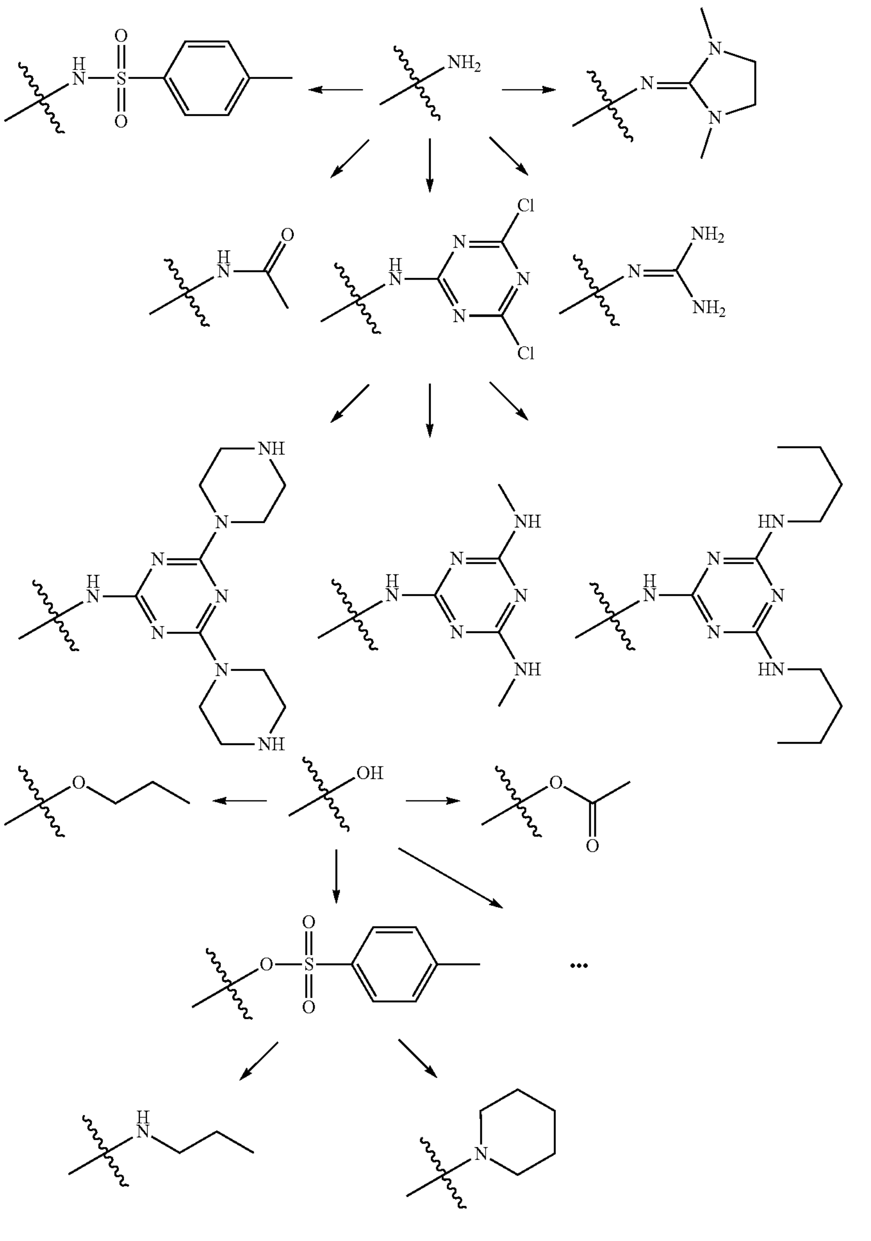

Oligonucleotide comprising at least one modified phosphate group of Formula (Fx) may also be produced according to the claimed method using standard protocols for automated solid-phase phosphoramidite synthesis.

The phosphoramidite method is the most efficient and widely used oligonucleotide synthesis method. Phosphoramidite synthesis protocols are known for those skilled in the art of oligonucleotide production and are primarily implemented in a solid-phase version using an automated DNA synthesizer. Briefly, DMTr nucleoside immobilized on a polymer support is subjected to de-tritylation and then condensation with the respectively activated nucleoside phosphoramidite to form phosphite triester. It is typically followed by "capping", i.e. acetylation of unreacted hydroxyl groups of nucleosides immobilized on a polymer support, and then phosphite triester is oxidized to phosphotriester using the respective oxidizing agent. This cycle is repeated until the target oligonucleotide sequence is grown.

The method for production of modified oligonucleotides according to the present invention includes the following steps:

1. synthesis of oligonucleotide chain is performed using a DNA synthesizer according to the standard phosphoramidite protocol up to the unit condensation step, with its phosphate part being modified according to the present invention; after the condensation of the respective monomer, the synthesis is stopped upon phosphite triester (F1) formation, up to the "capping" and oxidation steps. Phosphite triester (F1) formed at the condensation step is treated by azidotriazine (F2) at 5° C. to 65° C., preferably at 14° C. to 29° C., more preferred at 20° C. to 25° C., even more preferred at 20° C. to 25° C., to form the compound (F3);
2. when necessary, treatment with anhydrous amine solution with substitution of A and/or B with moieties —$NR^1R^2$, —$NR^3R^4$, or —$NR^XR^Y$ in the compound (F3) is performed, and further chemical transformation of functionalities $R^X$ и $R^Y$ are made to give structures $R^1$, $R^2$, $R^3$ and $R^4$;
3. continued oligonucleotide synthesis according to the phosphoramidite protocol up to the following unit condensation step, with its phosphate part being modified according to the present invention, and steps 1, 2 are repeated; or the synthesis is continued to produce full-length oligonucleotide. Final deblocking of the synthesized oligonucleotide to produce target structure according to formula (Fx) is performed.

If A and B in azidotriazine (F2) are —$NR^1R^2$ and —$NR^3R^4$, step 2 is omitted.

In an embodiment, A and B in azidotriazine (F2) may represent chlorines. 2-Azido-4,6-dichloro-1,3,5-triazine may be produced in a single step from a commercially available cyanuric chloride as shown in Example 1.

In another embodiment, azidotriazine (F2) is 2-azido-4-alkylamino-6-chloro-1,3,5-triazine which may be produced from cyanuric chloride and the respective amine as shown in Examples 2-4.

In another embodiment, azidotriazine (F2) is 2-azido-4-alkylamino-4,6-chloro-1,3,5-triazine which may be produced from cyanuric chloride and the respective amines as shown in Example 5.

The disclosed method for production of a modified oligonucleotide may be implemented in a liquid-phase variant where all reagents in all reactions are in a solution and are not bound to solid-phase supports. However, the preferably claimed method is implemented in a solid-phase version where the synthesized oligonucleotide is bound to a solid-phase support.

Polymer support may be used as a solid-phase support. Exemplary polymer supports may include, but not limited to, controlled pore glass (CPG), polystyrene resins, TentaGel®, TSK Gel® Toyopearl®, polyvinyl alcohol, cellulose acetate, etc.

Further solid-phase oligonucleotide treatments provide process advantages such as easy treatment product isolation from unreacted reagent solution, low costs of agent modifications, and high efficiency of conducted reactions.

In a preferred embodiment, all phosphoramidite monomers are condensed automatically using an automated DNA synthesizer. At that, the triazine group may be incorporated into any internucleotide phosphate group of the oligonucleotide to be synthesized.

One of the main advantages of the claimed method is the ability to incorporate to the oligonucleotide of large variety of combinations of organic radicals R1, R2, R3, R4 in even one triazine phosphoramidite modification. At that, the claimed method provides for the initial production of a common precursor, the compound (F3), with possible further assembly of target organic radicals R1, R2, R3, R4 by treating the compound (F3) with various reagents as disclosed above. Such hierarchic assembly of the final structure (F0) allows producing a wide range of representatives of the claimed compound class using an available method having a special advantage of compatibility with the standard protocol of automated solid-phase phosphoramidite method of the oligonucleotide synthesis. Moreover, because of chemical stability of the produced amidotriazine link of this modification type in structure (Fx) both in alkaline and acidic environments, the produced modified oligonucleotides are stable in a wide range of pH.

High diversity of oligonucleotides produced within the claimed method is illustrated by Examples 6-43.

DESCRIPTION OF INVENTION EMBODIMENTS

These materials of the application provide a preferred disclosure of the embodiment of the claimed technical solution that should not be used as limiting other particular embodiments which do not go beyond the claimed scope of legal protection and are evident for those skilled in the art.

Hereinafter, the term "oligonucleotide" will be applied to oligodeoxyribonucleotides, unless otherwise specified.

GENERAL METHODS

Modified oligonucleotides were synthesized using an automated DNA synthesizer ASM-800 (Biosset, Russia) according to the phosphoramidite protocol [42] in the scale of 0.2 μmol using standard 25 μl reactors.

Phosphite triester to introduce to the Staudinger reaction with azidotriazine was produced as follows. Reactor containing 10 mg polymer support based on porous glass (500 Å) with immobilized nucleoside (nucleoside load 40 μmol/g) was placed to the DNA synthesizer, and the protocol of automated solid-phase oligonucleotide synthesis was initiated according to the β-cyanoethyl phoshoramidite scheme in the scale of 0.2 μmol. Oligonucleotide chain was synthesized up to the unit whose phosphate part will be modified with a triazine moiety. After the condensation step which produced phosphite triester, synthesis was terminated, the reactor was removed from the synthesizer and dried using a water-jet pump after washing with dry acetonitrile, the polymer support with immobilized phosphite triester was transferred from the reactor to a plastic tube to perform further reaction with the respective azidotriazine and, if required, additional treatments.

A 6-carboxyfluorescein moiety as a fluorescein phosphoramidite monomer was introduced using a special protocol with 0.1 M fluorescein phosphoramidite monomer, with the total volume of fluorescein phosphoramidite monomer 70 μl, and fluorescein phosphoramidite feed time 30 min. In all subsequent examples, the 6-carboxyfluorescein moiety within oligonucleotide is designated as [FAM].

1.5 ml plastic tubes with twisting caps were used for all reactions. After the solid-phase synthesis, the polymer support was transferred from the reactor to the plastic tube and the final deblocking step was performed using concentrated aqueous methylamine solution. After final deblocking, the supernatant was evaporated to dryness in vacuo on SpeedVac. 200 μl deionized water (mQ) was added to the residue, and the polymer support was isolated by centrifugation.

Modified oligonucleotides were isolated using reverse-phase high performance liquid chromatography (RP-HPLC). The isolation was performed using chromatography unit Agilent 1200 (USA) and column Zorbax SB-C18 (5 μm)

4.6×50 mm in acetonitrile gradient in 20 mM triethylammonium acetate, pH 7, 0 to 90%, for 30 min, at flow rate 1.5 ml/min. Fractions containing the target product were evaporated in vacuo on SpeedVac. Oligonucleotides were then swaged by adding 1 ml of 1 M $LiClO_4$ solution in acetone, and the residue was washed with acetone and dried in air for 20 min. To control purity of modified oligonucleotides, denaturating polyacrylamide gel electrophoresis (PAGE) was used with 15% or 20% methylenebisacrylamide using band visualization by staining with Stains-All dye solution. Molecular weights of modified oligonucleotides were defined using mass spectroscopy MALDI-TOF or ESI in a positive or negative ion recording variant.

Embodiments of the Method for Modified Oligonucleotide Production

Embodiment 1. Incorporation of 4,6-dialkylamino-1,3,5-triazino-2-amidophosphate Using 2-azido-4,6-dichloro-1,3,5-triazine 1. Oligonucleotide chain was synthesized up to the unit whose phosphate part will be modified with a triazine moiety on a DNA synthesizer as described in general methods. Further, phosphite triester immobilized on a solid-phase support was transferred to a tube and 200 μl of 0.03-1 M solution of 2-azido-4,6-dichloro-1,3,5-triazine was added, purged with argon, and shaken for 15 min at room temperature. The suspension was spin at 13,400 rpm for 30 sec, the supernatant was taken, and the polymer support was washed three times with 200 μl dry acetonitrile. 2. In a plastic tube with the polymer support, 200 μl amine solution (0.1-3 M) was added, which contains the desired functional moieties, or functional moieties for further modifications, such as —OH, —$NH_2$, —NH— etc. In the latter case, sequential chemical transformations were performed by treating with various solutions for further modifications, such as reactions with tosyl chloride, acid chlorides, amines, guanidine reagents, etc. (see DETAILED DESCRIPTION OF THE INVENTION). Between treatments with solutions, the suspension was spin at 13,400 rpm for 30 sec, the supernatant was taken, and the polymer support was washed three times with 200 μl dry acetonitrile. 3. The support with the immobilized modified oligonucleotide was transferred to the reactor to synthesize oligonucleotides, and the automated solid-phase synthesis according to the phosphoramidite protocol was then continued. After the oligonucleotide synthesis was completed, final deblocking with an aqueous methylamine solution was performed.

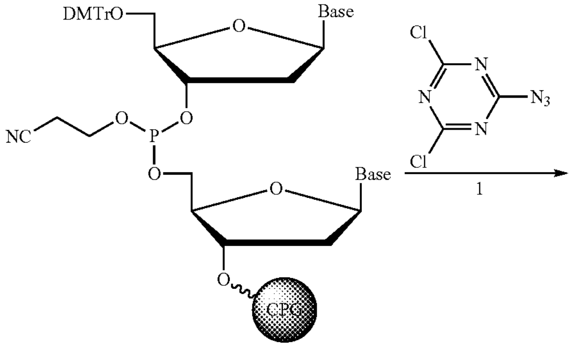

-continued

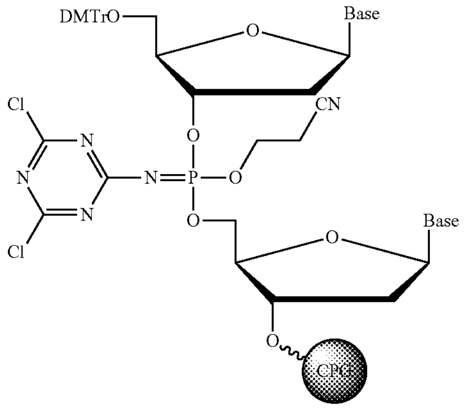

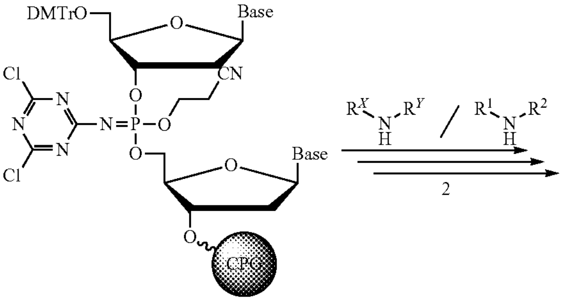

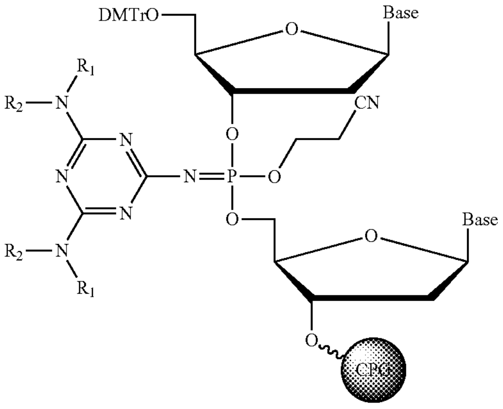

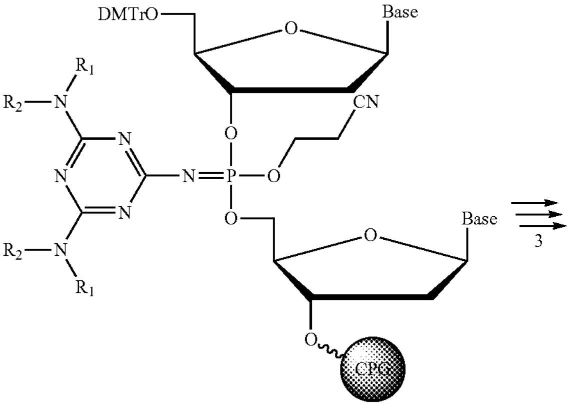

-continued

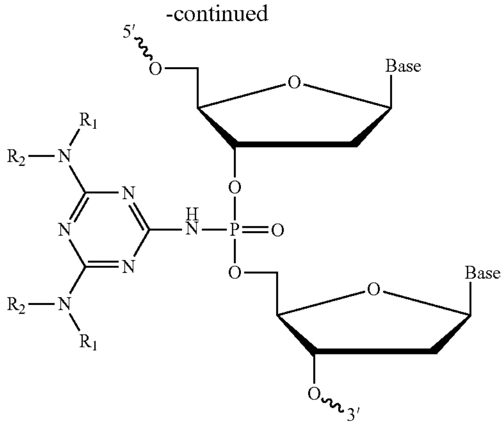

Embodiment 2. Introduction of 4,6-dialkylamino-1,3,5-triazino-2-amidophosphate Moiety Using 2-azido-4-alkylamino-6-chloro-1,3,5-triazines 1. Oligonucleotide chain was synthesized up to the unit whose phosphate part will be modified with a triazine moiety on a DNA synthesizer as described in general methods. Further, phosphite triester immobilized on a solid-phase support was transferred to a tube, and 200 μl of 0.1-3 M 2-azido-4-alkylamino-6-chloro-1,3,5-triazine solution in an anhydrous acetonitrile or toluene was added, purged with argon, and shaken for 1-3 hours at room temperature. The suspension was spin at 13,400 rpm for 30 sec, the supernatant was taken, and the polymer support was washed three times with 200 μl dry acetonitrile.
2. 200 μl amine (0.1-3 M) solution comprising the desired functionalities or functionalities intended for further modification, such as —OH, —$NH_2$, —NH— etc., was added to a plastic tube with the polymer support. In the latter case, sequential chemical transformations were performed by treating with various solutions for further modifications, such as reactions with tosyl chloride, acid chlorides, amines, guanidine reagents, etc. (see DETAILED DESCRIPTION OF THE INVENTION). Between treatments with solutions, the suspension was spin at 13,400 rpm for 30 sec, the supernatant was taken, and the polymer support was washed three times with 200 μl dry acetonitrile.
3. The support with the immobilized modified oligonucleotide was transferred to the reactor for oligonucleotide synthesis, and automated solid-phase synthesis was then continued according to the phosphoramidite protocol. After the oligonucleotide synthesis was completed, final deblocking with an aqueous methylamine solution was performed.

-continued

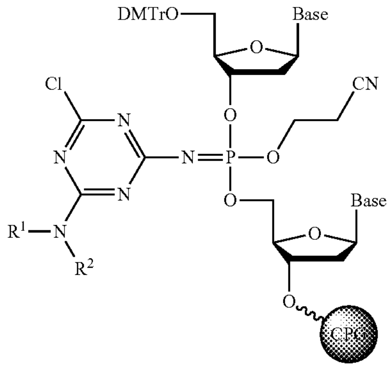

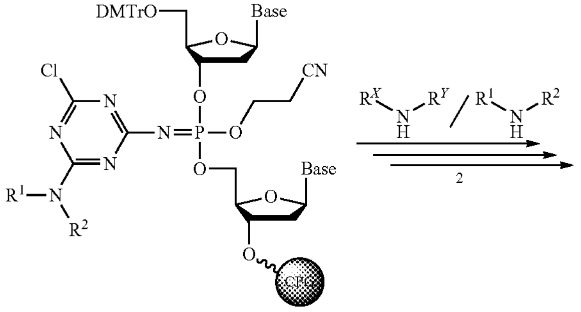

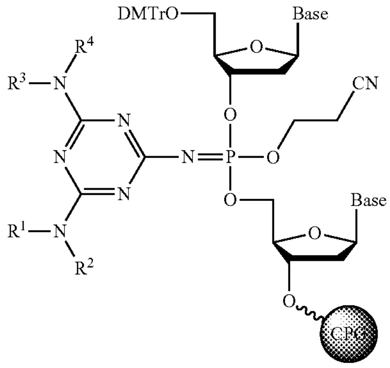

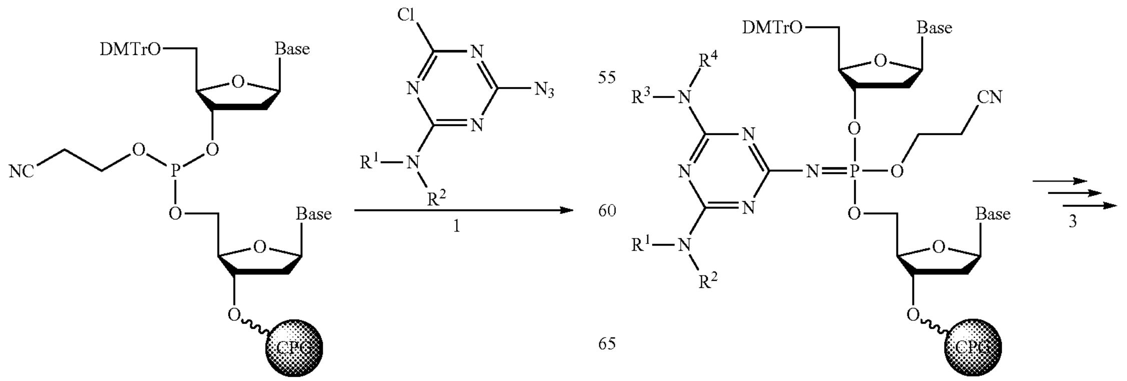

-continued

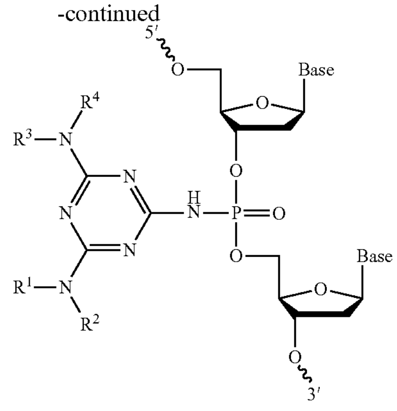

Embodiment 3. Introduction of 4,6-dialkylamino-1,3,5-triazino-2-amidophosphate moiety using 2-azido-4,6-dialkylamino-1,3,5-triazines. 1. The oligonucleotide chain up to the unit whose phosphate part will be modified by a triazine moiety was synthesized on a DNA synthesizer as described in general methods. Further, phosphite triester immobilized on a solid-phase support was transferred to a tube, and 200 μl of 0.5 M 2-azido-4,6-dialkylamino-1,3,5-triazine solutions was added to DMF, purged with argon, and shaken for 1-3 hours at 65° C. The suspension was spin at 13,400 rpm for 30 sec, the supernatant was taken, and the polymer support was washed three times with 200 μl dry acetonitrile. 2. The support with the immobilized modified oligonucleotide was transferred to the reactor to synthesize oligonucleotides, and the automated solid-phase synthesis was then continued according to the β-cyanoethyl phosphoramidite protocol. After the oligonucleotide synthesis was completed, final deblocking with an aqueous methylamine solution was performed.

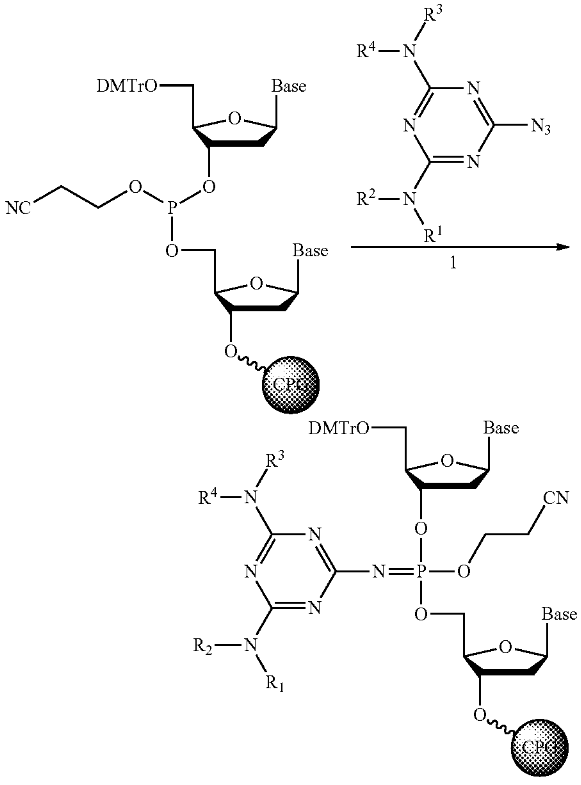

-continued

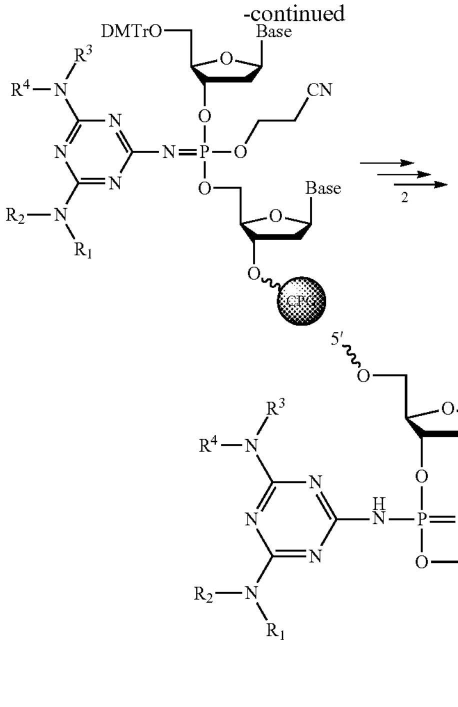

EXAMPLES

These materials of the application provide a preferred disclosure of the embodiment of the claimed technical solution that should not be used as limiting other particular embodiments which do not go beyond the claimed scope of legal protection and are obvious for those skilled in the art.

Figure 2:
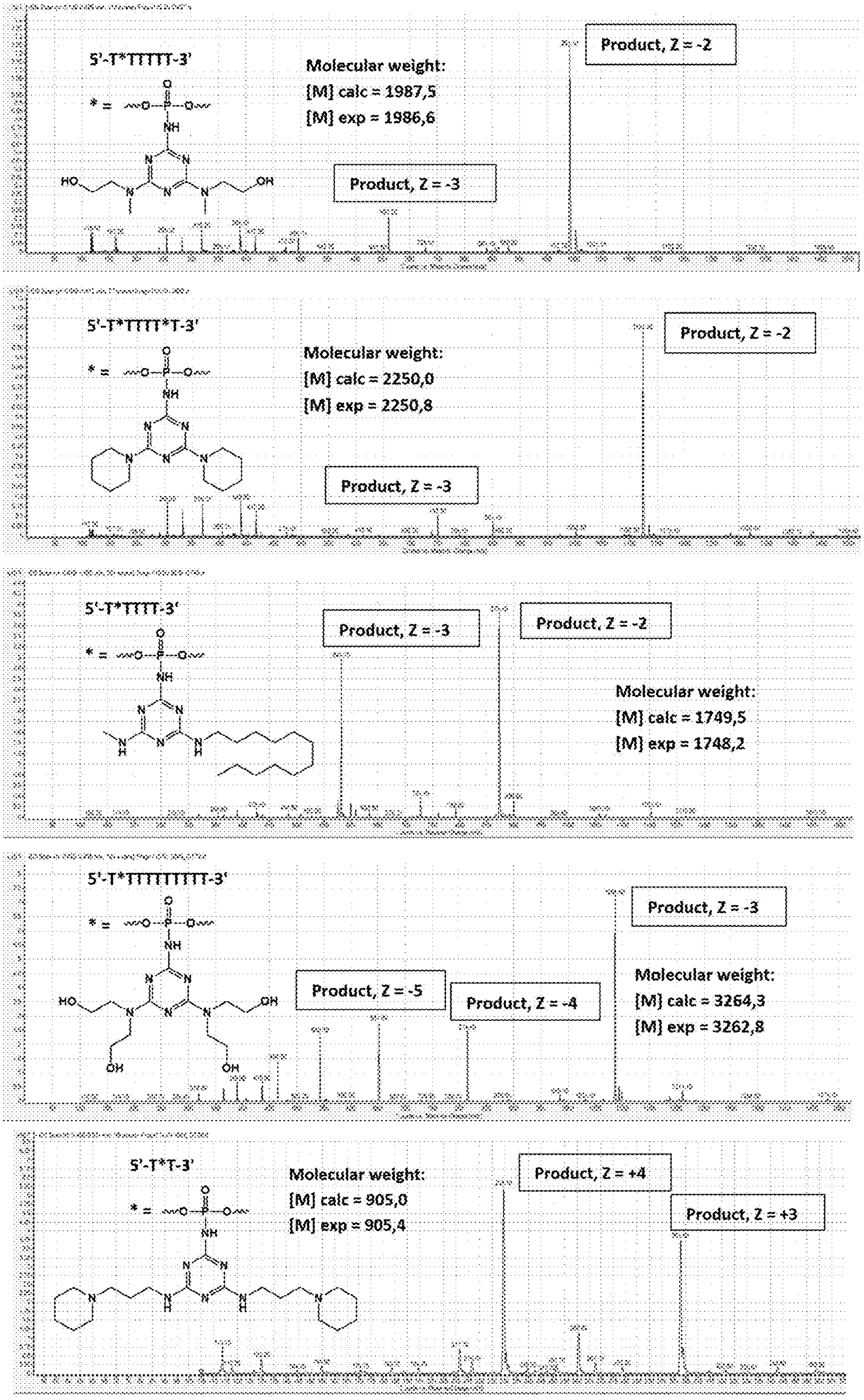
FIG. 2 shows examples of mass spectrometry (ESI MSI) of the produced compounds.

Examples of chromatography and mass-spectrometry of the produced compounds are shown in FIGS. 1 and 2.

Preparation of Azidotriazines

Example 1. Preparation of 2-azido-4,6-dichloro-1,3,5-triazine

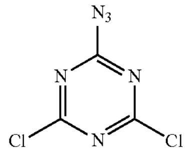 [SMILES: [N-]=[N+]=Nc1nc(Cl)nc(Cl)n1]

1 eq. sodium azide (1.06 g, 16.3 mmol) was added to a cyanuric chloride (3.0 g, 16.3 mmol) solution and stirred on a magnetic stirrer for 2 hours at room temperature. Acetone was evaporated, and the residue was dissolved in methylene chloride. The substance was purified from excessive sodium chloride in a separation funnel and sequentially washed with 20 ml concentrated NaCl solution four times. The organic layer was dried over $Na_2SO_4$, evaporated to dryness, and the formed residue was dried in vacuo. 2.36 g (76%) white precipitate product was obtained. The substance was further purified by column chromatography with 50 g silica gel in a mix of methylene chloride/hexane with methylene chloride gradient 0 to 25%. Chromatographic fractions containing the product were evaporated to dryness and dried in vacuo. 0.616 g (19.8%) pure product was obtained.

Example 2. Preparation of 2-azido-4-dodecylamino-6-chloro-1,3,5-triazine

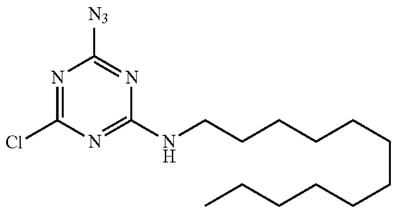 [SMILES: CCCCCCCCCCCCNc1nc(Cl)nc(N=[N+]=[N-])n1]

To a solution of cyanuric chloride (0.7 g, 3.8 mmol) in 25 ml chloroform, 1 eq. dodecyl amine (0.7 g, 3.8 mmol) and 10 ml 10% (wt.) NaOH solution were added and then stirred on a magnetic stirrer for 24 hours at room temperature. The substance was purified from excessive sodium chloride in a separation funnel and washed with 15 ml concentrated NaCl solution three times. The organic layer was dried over $Na_2SO_4$, evaporated to dryness, and the formed residue was dried in vacuo. The substance was further purified by re-crystallization in a mix of methanol/chloroform 5:1 at 0° C. The re-crystallization mix was isolated from the precipitate and dried in vacuo. 0.872 g (68.7%) white precipitate product of 2-dodecylamino-4,6-dichloro-1,3,5-triazine was obtained.

1.25 eq. sodium azide (0.2 g, 3.09 mmol) was added to a solution of 2-dodecylamino-4,6-dichloro-1,3,5-triazine (0.822 g, 2.47 mmol) in 40 ml acetone, and then stirred on a magnetic stirrer for 5 hours at room temperature. Acetone was evaporated, and the residue was dissolved in methylene chloride. The substance was purified from excessive sodium chloride in a separation funnel and washed with 15 ml concentrated NaCl solution four times. The organic layer was dried over $Na_2SO_4$, evaporated to dryness, and the formed residue was dried in vacuo. 0.693 g (82.5%) white precipitate product was obtained. The substance was further purified by column chromatography with 40 g silica gel in a mix of ethyl acetate/hexane with ethyl acetate gradient 0 to 10%. Chromatographic fractions containing the product were evaporated to dryness and dried in vacuo. 0.168 g (20%) pure product was obtained as a white precipitate of 2-azido-4-dodecylamino-6-chloro-1,3,5-triazine.

To prepare 0.1 M solution, 6.8 mg 2-azido-4-dodecylamino-6-chloro-1,3,5-triazine was dissolved in 200 µl dry toluene, shaken until the precipitate dissolution, and purged with argon. The solution was prepared immediately before the reaction.

Example 3. Preparation of 2-azido-4-oleylamino-6-chloro-1,3,5-triazine

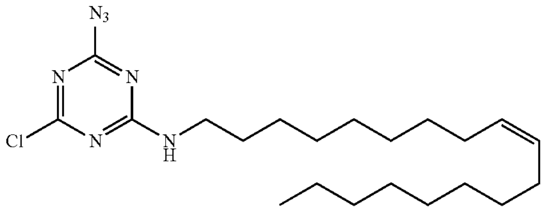 [SMILES: CCCCCCCC/C=C\CCCCCCCCNc1nc(Cl)nc(N=[N+]=[N-])n1]

1 eq. oleylamine (1.25 ml, 3.8 mmol) and 10 ml 10% (wt.) NaOH solution was added to a cyanuric chloride (0.7 g, 3.8 mmol) solution in 20 ml chloroform, and stirred on a magnetic stirrer for 24 hours at room temperature. The substance was purified from excessive sodium chloride in a separation funnel and washed with 15 ml concentrated NaCl solution three times. The organic layer was dried over $Na_2SO_4$, evaporated to dryness, and the formed residue was dried in vacuo. 1.498 g (95%) pink oil-like product was obtained. The substance was further purified by column chromatography with 40 g silica gel in a mix of ethyl acetate/hexane with ethyl acetate gradient 0 to 7.5%. Chromatographic fractions containing the product were evaporated to dryness and dried in vacuo. 0.953 g (60%) pure oil-like product, 2-oleylamino-4,6-dichloro-1,3,5-triazine, was obtained.

1.25 eq. sodium azide (0.173 g, 2.65 mmol) was added to a solution of 2-oleylamino-4,6-dichloro-1,3,5-triazine (0.881 g, 2.12 mmol) in 30 ml acetone, and stirred on a magnetic stirrer for 6 hours at room temperature. Acetone was evaporated, and the residue was dissolved in methylene chloride. The substance was purified from excessive sodium chloride in a separation funnel and washed with 15 ml concentrated NaCl solution four times. The organic layer was dried over $Na_2SO_4$, evaporated to dryness, and the formed residue was dried in vacuo. 0.787 g (87.9%) yellow oil-like product was obtained. The substance was further purified by column chromatography with 40 g silica gel in a mix of ethyl acetate/hexane with ethyl acetate gradient 0 to 10%. Chromatographic fractions containing the product were evaporated to dryness and dried in vacuo. 0.438 g (49%) pure oil-like product, 2-azido-4-oleylamino-6-chloro-1,3,5-triazine, was obtained.

To prepare 0.1 M solution, 8.4 mg 2-azido-4-oleylamino-6-chloro-1,3,5-triazine in 200 µl dry acetonitrile was dissolved, shaken until the precipitate is dissolved, dried over sieves for 24 hours at room temperature, and purged with argon. The solution was prepared immediately before the reaction.

Example 4. Preparation of 2-azido-4-(N-methyl-N-octadecyl)amino-6-chloro-1,3,5-triazine

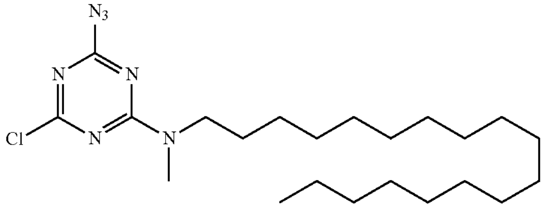 [SMILES: CCCCCCCCCCCCCCCCCCN(C)c1nc(Cl)nc(N=[N+]=[N-])n1]

1 eq. (N-methyl-N-octadecyl)amine (0.38 g, 1.36 mmol) and 10 ml 10% (wt.) NaOH solution was added to a solution of cyanuric chloride (0.25 g, 1.36 mmol) in 20 ml chloroform, and stirred on a magnetic stirrer for 24 hours at room temperature. The substance was purified from excessive sodium chloride in a separation funnel and washed with 15 ml concentrated NaCl solution three times. The organic layer was dried over $Na_2SO_4$, evaporated to dryness, and the precipitate formed was dried in vacuo. 0.472 g (80%) pure product as white precipitate of 2-(N-methyl-N-octadecyl) amino-4,6-dichloro-1,3,5-triazine was prepared.

1.2 eq. sodium azide (0.079 g, 1.19 mmol) was added to a solution of 2-(N-methyl-N-octadecyl)amino-4,6-dichloro- 1,3,5-triazine (0.428 g, 0.99 mmol) in 30 ml acetone, and stirred on a magnetic stirrer for 6 hours at room temperature. Acetone was evaporated, and the residue was dissolved in methylene chloride. The substance was purified from excessive sodium chloride in a separation funnel and washed with 15 ml concentrated NaCl solution four times. The organic layer was dried over $Na_2SO_4$, evaporated to dryness, and the formed residue was dried in vacuo. 0.351 g (80.5%) white precipitate product was prepared. The substance was further purified by column chromatography using 35 g silica gel in a mix of ethyl acetate/hexane with ethyl acetate gradient 0 to 4%. Chromatographic fractions containing the product were evaporated to dryness and dried in vacuo. 0.306 g (49%) pure product as a white precipitate of 2-azido-4-(N-methyl-N-octadecyl)-amino-6-chloro-1,3,5-triazine was prepared.

To prepare 0.1 M solution, 8.8 mg 2-azido-4-(N-methyl-N-octadecyl)amino-6-chloro-1,3,5-triazine in 200 μl dry toluene was dissolved, shaken until the precipitate is dissolved, and purged with argon. The solution was prepared immediately before the reaction.

Example 5. Preparation of 2-azido-4,6-dibutylamino-1,3,5-triazine

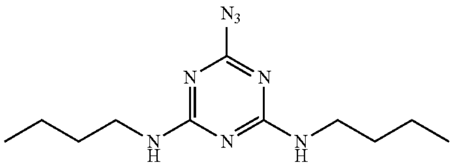 [SMILES: CCCCNc1nc(N=[N+]=[N-])nc(NCCCC)n1]

4 eq. butyl amine (0.52 ml, 5.2 mmol) was added to a solution of 2-azido-4,6-dichloro-1,3,5-triazine (0.25 g, 1.3 mmol) in 20 ml THF, and stirred on a magnetic stirrer for 24 hours at room temperature. Butylamine hydrochloride precipitate was filtered on a glass porous filter (16 pores), the remaining solution was evaporated to dryness, and the precipitate formed was dried in vacuo. 0.34 g (98.6%) pure product as a white precipitate of 2-azido-4,6-dibutylamino-1,3,5-triazine was prepared.

To prepare 0.5 M solution, 26.4 mg 2-azido-4,5-dibutylamino-1,3,5-triazine was dissolved in 200 μl dry DMF, shaken until the precipitate is dissolved, and purged with argon. The solution was prepared immediately before the reaction.

Preparation of Modified Oligonucleotides

Example 6. Preparation of Modified Oligonucleotides According to Embodiment 1 with Incorporation of Methylamine Moieties

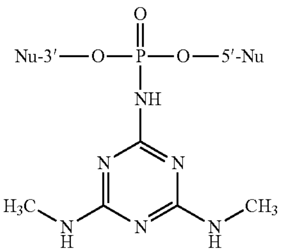

In the example, modified oligonucleotides 5'-d(T*TTTT), 5'-d(T*TTTTTTTTT), 5'-d(T*TTTTT), 5'-d(TT*TTTTT), 5'-d(T*T*TTTTTTTT) were prepared.

Modified oligonucleotides were prepared according to embodiment 1, wherein item 2 was omitted.

Molecular Weights:

5'-d(T*TTTT): calculated [M]1,595.19, obtained [M+H] 1,595.41.

5'-d(TT*TTTTT): calculated [M]2,202.0, obtained [M−H]2,203.0.

Example 7. Synthesis of Modified Oligonucleotides According to Embodiment 1 with the Piperidine Solution Treatment

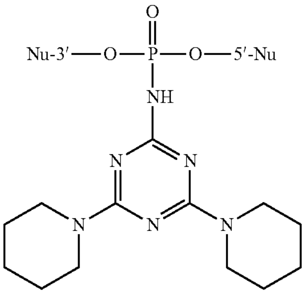

In the example, modified oligonucleotides 5'-d(T*TTTT), 5'-d(T*TTTTTTTTT), 5'-d(T*TTTT*T) were prepared.

Modified oligonucleotides were prepared according to embodiment 1, wherein sequential treatments in item 2 are 10% (vol) piperidine in dry acetonitrile, 1 hour, 25° C.

Molecular Weight:

5'-d(T*TTTT*T): calculated [M]2,250.0, obtained [M−H]2,250.8.

Example 8. Synthesis of Modified Oligonucleotide According to Embodiment 1 with the (N-Methyl) Butylamine Solution Treatment

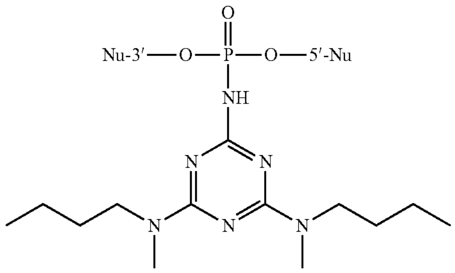

In the example, modified oligonucleotide 5'-d(T*TTTTT) was prepared according to embodiment 1, wherein sequential treatments in item 2 are 50% (vol) (N-methyl) butylamine in dry acetonitrile, 30 min, 25° C.

Molecular Weight:

5'-d(T*TTTTT): calculated [M]2,011.6, obtained [M−H] 2,010.6.

Example 9. Synthesis of Modified Oligonucleotides According to Embodiment 1 with the Dodecylamine Solution Treatment

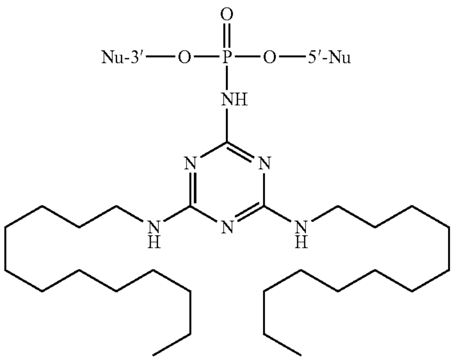

In the example, modified oligonucleotides 5'-d(T*TTTT), 5'-d(TTTT*T), 5'-d(CTGACTATGAAGTAT*T), 5'-[FAM]-d(CTGACTATGAAGTAT*T),5'-[FAM]-d(CTGACTATG-AAGTAT*T*T),5'-d(TTTTTTTTT*T),5'-d(AATACTTC-ATAGTCAGT*T) were prepared.

Modified oligonucleotides were prepared according to embodiment 1, wherein sequential treatments in item 2 are 3 M dodecyl amine in dry pyridine, 30 min, 55° C.

Molecular Weights:

5'-d(T*TTTT): calculated [M]1,903.8, obtained [M−H]1, 902.6.

5'-d(AATACTTCATAGTCAGT*T): calculated [M]5, 917.4, obtained [M−H]5,916.4.

5'-[FAM]-d(CTGACTATGAAGTAT*T): calculated [M] 5,876.8, obtained [M−H]5,876.4.

Example 10. Synthesis of Modified Oligonucleotides According to Embodiment 1 with the Butylamine Solution Treatment

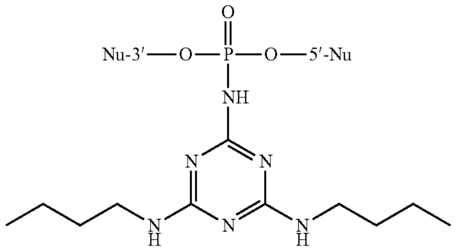

In the example, modified oligonucleotides 5'-d (CTGACTATGAAGTAT*T), 5'-[FAM]-d(CTGACTATG AAGTAT*T), 5'-d(TTTTTTTTT*T), 5'-d(T*T*TTTT-TTTT) were prepared.

Modified oligonucleotides were prepared according to embodiment 1, wherein sequential treatments in item 2 are 20% (vol) butylamine in dry acetonitrile, 1 hour, 40° C.

Molecular Weight:

5'-[FAM]-d(CTGACTATGAAGTAT*T): calculated [M]5,652.5, obtained [M−H]5,652.1.

Example 11. Synthesis of Modified Oligonucleotide According to Embodiment 1 with Oleylamine Solution Treatment

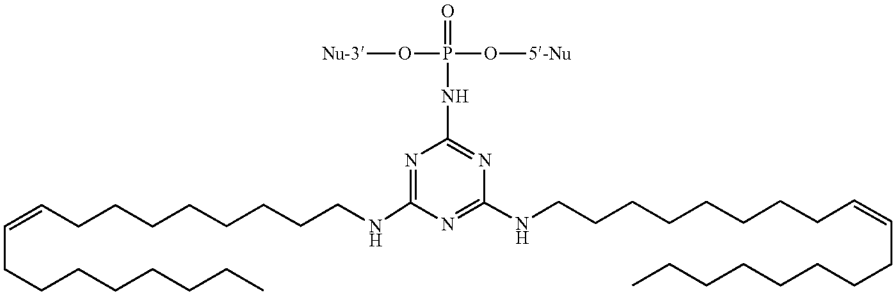

In the example, modified oligonucleotide 5'-d(T*TTTT) was prepared according to embodiment 1, wherein sequential treatments in item 2 are 2 M oleylamine in dry pyridine, 30 min, 55° C.

Molecular Weight:

5'-d(T*TTTT): calculated [M]2,068.1, obtained [M−H]2, 066.1.

Example 12. Synthesis of Modified Oligonucleotide According to Embodiment 1 with the (N-methyl-N-octadecyl)amine Solution Treatment

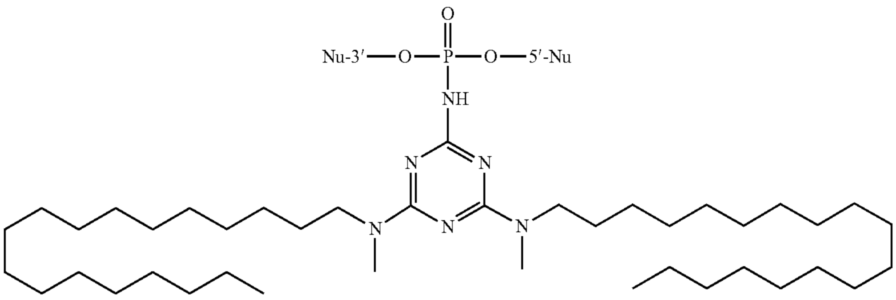

In the example, modified oligonucleotide 5'-d(T*TTTT) was prepared according to embodiment 1, wherein sequential treatments in item 2 are 2 M N-methyl-N-octadecylamine in dry pyridine, 30 min, 55° C.

Molecular Weight:

5'-d(T*TTTT): calculated [M]2,100.0, obtained [M−H]2,099.1.

Example 13. Synthesis of Modified Oligonucleotide According to Embodiment 1 with the Dimethylamine Solution Treatment

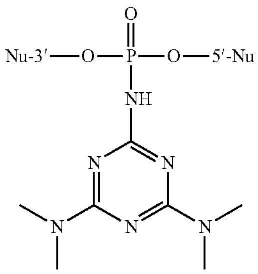

In the example, modified oligonucleotide 5'-d(T*TTTTT) was prepared according to embodiment 1, wherein item 2 was omitted; oligonucleotide was de-blocked from the solid-phase support using conc. (approx. 40%) aqueous solution of dimethylamine at 55° C.

Molecular Weight:

5'-d(T*TTTTT): calculated [M]1,927.4, obtained [M−H] 1,926.4.

Example 14. Synthesis of Modified Oligonucleotide According to Embodiment 1 with the Dihexylamine Solution Treatment

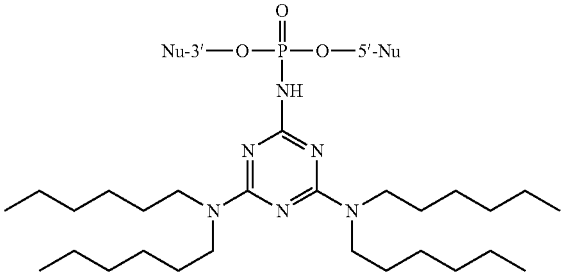

In the example, modified oligonucleotide 5'-d(T*TTTT) was prepared according to embodiment 1, wherein sequential treatments in item 2 are 10% (vol) dihexylamine in dry acetonitrile, 1 hour, 25° C.

Molecular Weight:

5'-d(T*TTTT): calculated [M]1,903.8, obtained [M−H]1,902.7.

Example 15. Synthesis of Modified Oligonucleotides According to Embodiment with the (N,N-Dimethylamino)Propylamino Solution Treatment

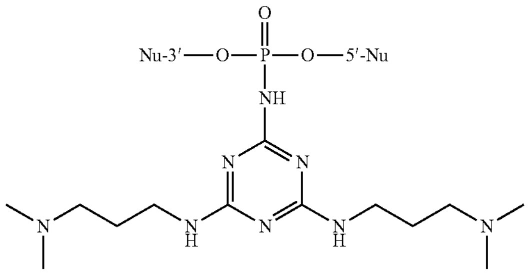

In the example, modified oligonucleotides 5'-d(T*TTTT), 5'-d(CTGACTATGAAGTAT*T), 5'-[FAM]-d(CTGACTATGAAGTAT*T), 5'-d(TTTTTTTTT*T), 5'-d(T*TTTTTTTTT), 5'-d(TTTTTTTT*T*T) were prepared.

Modified oligonucleotides were prepared according to embodiment 1, wherein sequential treatments in item 2 are 10% (vol) (N,N-dimethylamino)propylamine in dry acetonitrile, 1 hour, 25° C.

Molecular Weight:

5'-d(T*TTTT): calculated [M]1,737.43, obtained [M+H] 1,737.64.

Example 16. Synthesis of Modified Oligonucleotides According to Embodiment with the 3,3'-Iminobis(N,N-Dimethyl-Propylamine) Solution Treatment

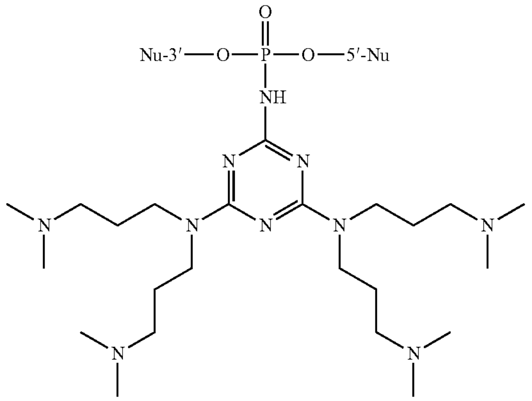

In the example, modified oligonucleotides 5'-d(T*TTTT), 5'-d(TTTT*T), 5'-d(T*T), 5'-d(CTGACTATGAAGTAT*T), 5'-[FAM]-d(CTGACTATGAAGTAT*T), 5'-d(T*TTTTTTTTT), 5'-d(TTTTTTTTT*T) were prepared.

In the embodiment, modified oligonucleotides were prepared according to embodiment 1, wherein sequential treatments in item 2 are 10% (vol) 3,3'-iminobis(N,N-dimethyl-propylamine) in dry acetonitrile, 1 hour, 25° C.

Molecular Weights:

5'-d(TTTT*T): calculated [M]1,907.7, obtained [M−H]1,906.6.

5'-d(T*T): calculated [M]995.1, obtained [M+H]994.1.

Example 17. Synthesis of Modified Oligonucleotide According to Embodiment 1 with the 1,6-Diaminohexane Solution Treatment

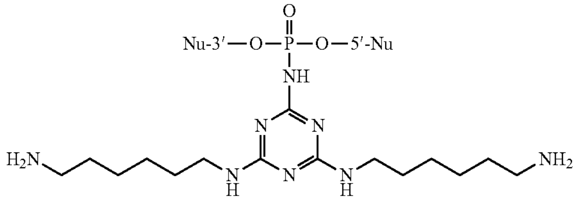

In the example, modified oligonucleotide 5'-d(T*TTTTTTTTT) was prepared according to embodiment 1, wherein sequential treatments in item 2 are 2 M 1,6-diaminohexane in dry acetonitrile, 1 hour, 55° C.

Molecular Weight:

5'-d(T*TTTTTTTTT): calculated [M]3,286.5, obtained [M−H]3,285.8.

Example 18. Synthesis of Modified Oligonucleotide According to Embodiment 1 with the 1,4-Diaminobutane Solution Treatment

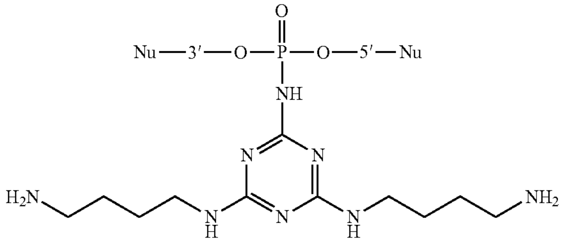

In the example, modified oligonucleotide 5'-d(T*TTTTTTTTT) was prepared according to embodiment 1, wherein sequential treatments in item 2 are 10% (vol) 1,4-diaminobutane in dry acetonitrile, 1 hour, 55° C.

Molecular Weight:

5'-d(T*TTTTTTTTT): calculated [M]3,230.3, obtained [M−H]3,229.7.

Example 19. Synthesis of Modified Oligonucleotides According to Embodiment 1 with the Tris (2-Aminoethyl)Amine Solution Treatment

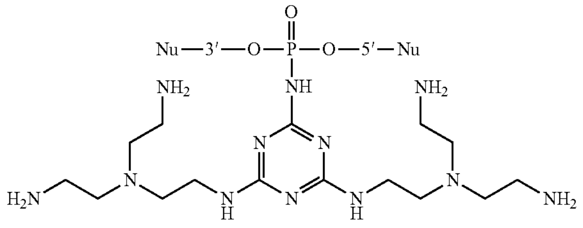

In the example, modified oligonucleotides 5'-d(T*TTTT), 5'-d(T*T), 5'-d(T*TTTTTTTTT) were prepared according to embodiment 1, wherein sequential treatments in item 2 are 10% (vol) tris (2-aminoethyl)amine in dry acetonitrile, 1 hour, 25° C.

Molecular Weights:

5'-d(T*TTTTTTTTT): calculated [M]3,346.5, obtained [M−H]3,345.0.

5'-d(T*TTTT): calculated [M]1,825.5, obtained [M−H]1,824.2.

Example 20. Synthesis of Modified Oligonucleotide According to Embodiment 1 with the Piperazine Solution Treatment

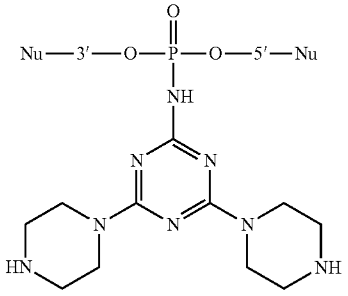

In the example, modified oligonucleotide 5'-d(T*TTTTTTTTT) was prepared according to embodiment 1, wherein sequential treatments in item 2 are 2 M piperazine in dry chloroform, 2 hours, 25° C.

Molecular Weight:

5'-d(T*TTTTTTTTT): calculated [M]3,226.3, obtained [M−H]3,225.7.

Example 21. Synthesis of Modified Oligonucleotide According to Embodiment 1 Using Sequential Treatments with the Tris (2-Aminoethyl)Amine and Guanidine and S-Methylurea Solutions

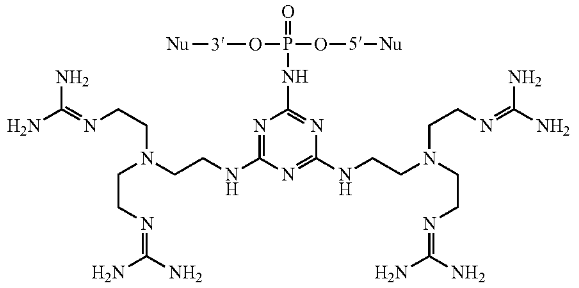

In the example, modified oligonucleotide 5'-d(T*TTTTT) was prepared according to embodiment 1, wherein sequential treatments in item 2 are 10% (vol) tris (2-aminoethyl) amine in dry acetonitrile, 1 hour, 25° C.→10 mg S-methylurea/100 µl dry acetonitrile/50 µl 25 mM $NaHCO_3$, 24 hours, 55° C.

Molecular Weight:

5'-d(T*TTTTT): calculated [M]2,297.9, obtained [M−H] 2,297.0.

Example 22. Synthesis of Modified Oligonucleotides According to Embodiment 1 Using Sequential Treatments with the Tris (2-Aminoethyl)Amine and Dimethylimidazolidinium Hexafluorophosphate Chloride Solutions

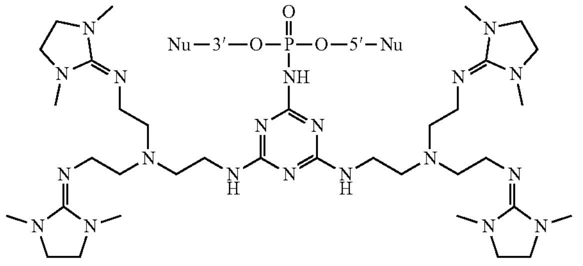

In the example, modified oligonucleotides 5'-d(T*TTTT), 5'-d(T*TTTTTTTTT), 5'-[FAM]-d(T*TTTTTTTTT), 5'-d(T*T) were prepared.

Modified oligonucleotides in the embodiment were prepared according to embodiment 1, wherein sequential treatments in item 2 are 10% (vol) tris (2-aminoethyl)amine in dry acetonitrile, 1 hour, room temperature→10 mg dimethylimidazolidinium hexafluorophosphate chloride/200 µl dry acetonitrile/7 µl DIPEA, 30 min, 55° C.

Molecular Weight:

5'-d(T*T): calculated [M]1,297.5, obtained [M+H]1, 296.0.

Example 23. Synthesis of Modified Oligonucleotides According to Embodiment 1 Using Sequential Treatments of the Tris (2-Aminoethyl)Amine and Acetic Anhydride Solutions

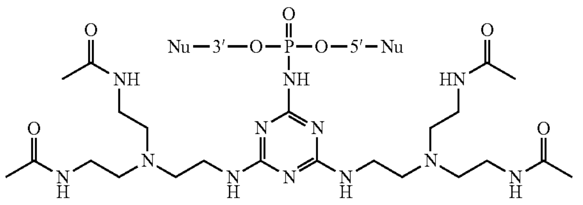

In the example, modified oligonucleotides 5'-d(T*TTTT), 5'-d(T*TTTTTTTTT), 5'-[FAM]-d(T*TTTTTTTTT) were prepared.

Modified oligonucleotides in the embodiment were prepared according to embodiment 1, wherein sequential treatments in item 2 are 10% (vol) tris (2-aminoethyl)amine in dry acetonitrile, 1 hour, 25° C.→standard solutions and capping step conditions in automated solid-phase phosphoramidite synthesis.

Molecular Weights:

5'-d(T*TTTTTTTTT): calculated [M]3,514.6, obtained [M−H]3,513.3.

5'-d(T*TTTT): calculated [M]1,993.7, obtained [M−H]1,992.4.

Example 24. Synthesis of Modified Oligonucleotide According to Embodiment 1 Using Sequential Treatments with the Piperazine and Tosyl Chloride Solutions

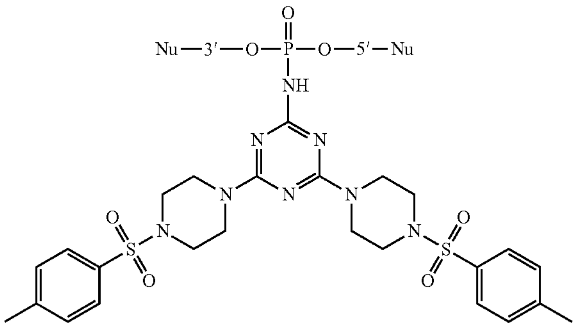

In the example, modified oligonucleotide 5'-d(T*TTTTTTTTT) was prepared according to embodiment 1, wherein sequential treatments in item 2 are 2 M piperazine in dry chloroform, 2 hours, 25° C.→2 M tosyl chloride in dry acetonitrile with addition of 2 M DIPEA in dry acetonitrile, 1 hour, 25° C.

Molecular Weight:

5'-d(T*TTTTTTTTT): calculated [M]3,534.6, obtained [M−H]3,533.4.

Example 25. Synthesis of Modified Oligonucleotide According to Embodiment 1 Using Sequential Treatments with the 1,6-Diaminohexane and Tosyl Chloride Solutions

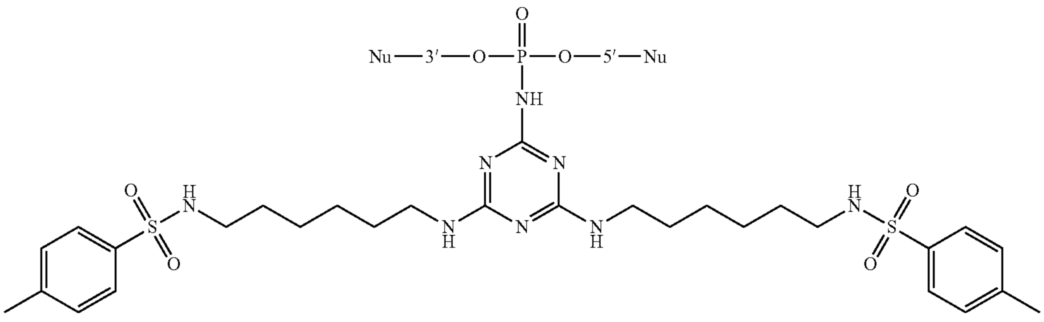

In the example, modified oligonucleotide 5'-d(T*TTTTTTTTT) was prepared according to embodiment 1, wherein sequential treatments in item 2 are 2 M 1,6-diaminohexane in dry acetonitrile, 1 hour, 55° C.→2 M tosyl chloride in dry acetonitrile with addition of 2 M DIPEA in dry acetonitrile, 1 hour, 25° C.

Molecular Weight:

5'-d(T*TTTTTTTTT): calculated [M]3,594.8, obtained [M−H]3,593.4.

Example 26. Synthesis of Modified Oligonucleotide According to Embodiment 1 Using Sequential Treatments of the Piperazine, Cyanuric Chloride and Methylamine Solutions

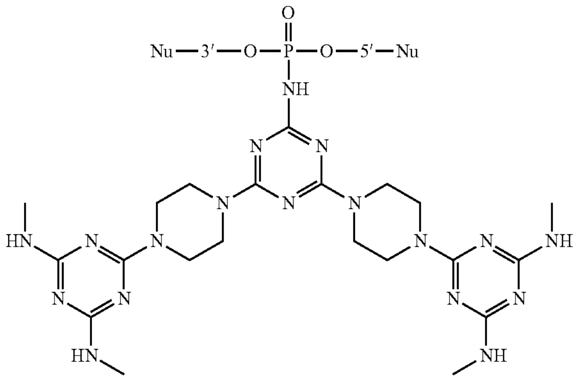

In the example, modified oligonucleotide 5'-d(T*TTTTTTTTT) was prepared according to embodiment 1, wherein sequential treatments in item 2 are 2 M piperazine in dry chloroform, 2 hours, 25° C.→1.5 M cyanuric chloride in dry acetonitrile with addition of 1.5 M DIPEA in dry acetonitrile, 15 min, 25° C.

Molecular Weight:

5'-d(T*TTTTTTTTT): calculated [M]3,498.0, obtained [M−H]3,498.9.

Example 27. Synthesis of Modified Oligonucleotide According to Embodiment 1 Using Sequential Treatments with the Piperazine, Cyanuric Chloride and Butylamine Solutions

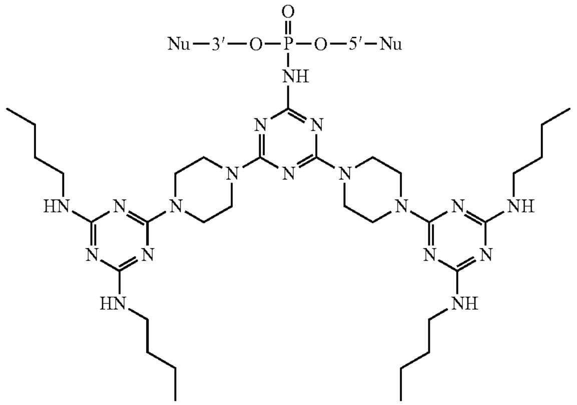

In the example, modified oligonucleotide 5'-d(T*TTTTTTTT) was prepared according to embodiment 1, wherein sequential treatments in item 2 are 2 M piperazine in dry chloroform, 2 hours, 25° C.→1.5 M cyanuric chloride in dry acetonitrile with addition of 1.5 M DIPEA in dry acetonitrile, 15 min, 25° C.→10% (vol) butylamine in dry acetonitrile, 1 hour, 55° C.

Molecular Weight:

5'-d(T*TTTTTTTT): calculated [M]3,668.9, obtained [M−H]3,667.2.

Example 28. Synthesis of Modified Oligonucleotide According to Embodiment 1 Using Sequential Treatments with the Piperazine, Cyanuric Chloride, Piperazine and Tosyl Chloride Solutions

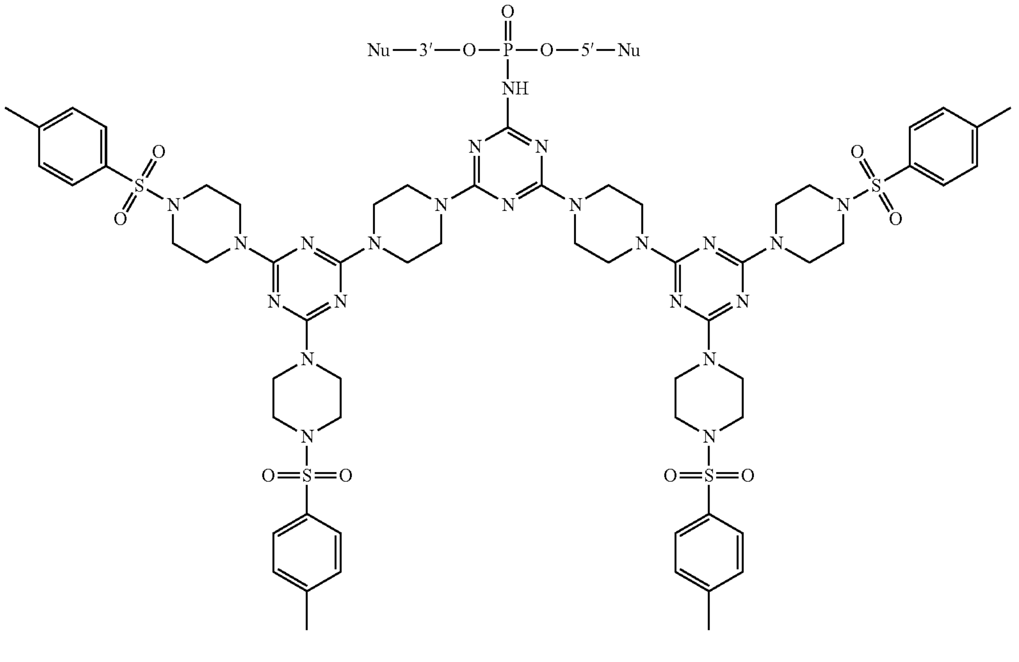

In the example, modified oligonucleotide 5'-d(T*TTTTTTTT) was prepared according to embodiment 1, wherein sequential treatments in item 2 are 2 M piperazine in dry chloroform, 2 hours, 25° C.→1.5 M cyanuric chloride in dry acetonitrile with addition of 1.5 M DIPEA in dry acetonitrile, 15 min, 25° C.→2 M piperazine in dry chloroform, 15 min, 25° C.→2 M tosyl chloride in dry acetonitrile with addition of 2 M DIPEA in dry acetonitrile, 1 hour, 25° C.

Molecular Weight:

5'-d(T*TTTTTTTT): calculated [M]4,337.7, obtained [M−H]4,336.0.

Example 29. Synthesis of Modified Oligonucleotide According to Embodiment 1 with the (N-Methyl)Aminoethanol Solution Treatment

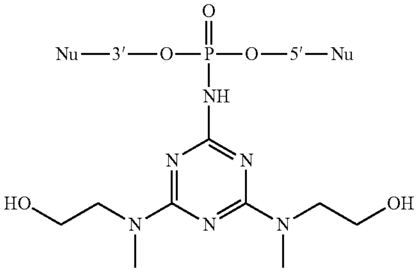

In the example, modified oligonucleotide 5'-d(T*TTTTT) was prepared according to embodiment 1, wherein sequential treatments in item 2 are 10% 2-(N-methyl)aminoethanol in dry acetonitrile, 1 hour, 25° C.

Molecular Weight:

5'-d(T*TTTTT): calculated [M]1,987.5, obtained [M−H]1,986.6.

Example 30. Synthesis of Modified Oligonucleotides According to Embodiment 1 with the Diethanolamine Solution Treatment

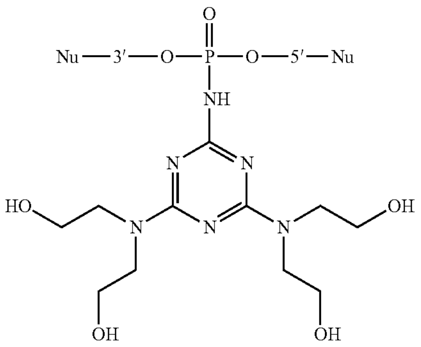

In the example, modified oligonucleotides 5'-d(T*TTTTTTTTT), 5'-d(T*TTTTT) are prepared according to embodiment 1, wherein sequential treatments in item 2 are 5% (vol) diethanolamine in a mix of acetone:acetonitrile 1:1, 1 hour, 55° C.

Molecular Weights:

5'-d(T*TTTTT): calculated [M]2,047.5, obtained [M−H]2,046.4.

5'-d(T*TTTTTTTTT): calculated [M]3,264.3, obtained [M−H]3,262.8.

Example 31. Synthesis of Modified Oligonucleotide According to Embodiment 1 with the 3-Aminopropanol Solution Treatment

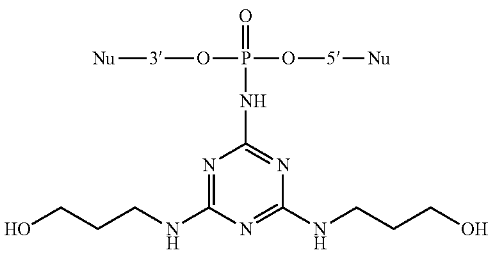

In the example, modified oligonucleotide 5'-d(T*TTTTTTTTT) was prepared according to embodiment 1, wherein sequential treatments in item 2 are 1.5 M 3-aminopropanol-1 in dry acetonitrile, 1 hour, 55° C.

Molecular Weight:

5'-d(T*TTTTTTTTT): calculated [M]3,204.3, obtained [M−H]3,203.6.

Example 32. Synthesis of Modified Oligonucleotide According to Embodiment 1 with the 6-Aminohexanol Solution Treatment

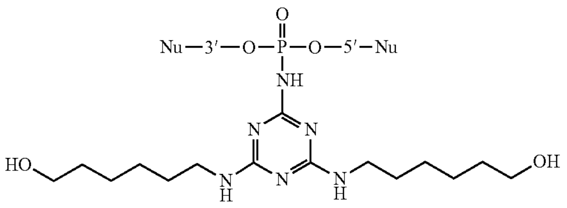

In the example, modified oligonucleotide 5'-d(T*TTTTTTTTT) was prepared according to embodiment 1, wherein sequential treatments in item 2 are 1.5 M 6-aminohexanol-1 in dry acetonitrile, 1 hour, 55° C.

Molecular Weight:

5'-d(T*TTTTTTTTT): calculated [M]3,288.4, obtained [M−H]3,287.7.

Example 33. Synthesis of Modified Oligonucleotide According to Embodiment 1 with the 2-(2-Aminoethoxy)Ethanol Solution Treatment

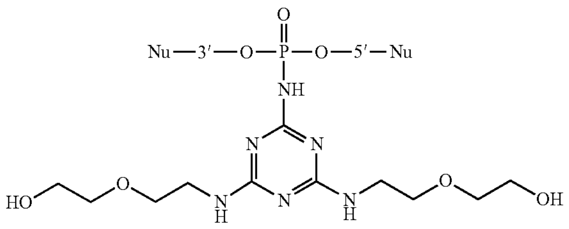

In the example, modified oligonucleotide 5'-d(T*TTTTT) was prepared according to embodiment 1, wherein sequential treatments in item 2 are 62.5% (vol) 2-(2-aminoethoxy) ethanol in dry acetonitrile, 1 hour, 25° C.

Molecular Weight:

5'-d(T*TTTTT): calculated [M]2,047.5, obtained [M−H]2,046.4.

Example 34. Synthesis of Modified Oligonucleotides According to Embodiment 1 Using Sequential Treatments with the 3-Aminopropanol and Piperidine Solutions

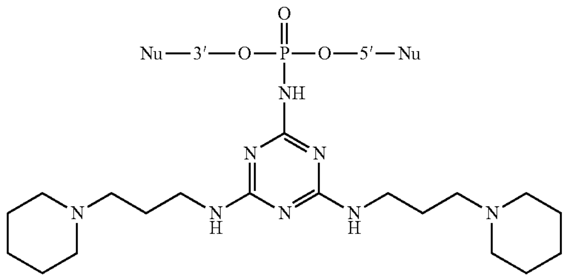

In the example, modified oligonucleotides 5'-d(T*TTTTTTTTT), 5'-d(T*T) according to embodiment 1, wherein sequential treatments in item 2 are 1.5 M 3-aminopropanol-1 in dry acetonitrile, 1 hour, 55° C.→2 M tosyl chloride in dry acetonitrile with addition of 2 M DIPEA in dry acetonitrile, 1 hour, 25° C.→10% (vol) piperidine in dry acetonitrile, 24 hours, 40° C.

Molecular Weight:

5'-d(T*T): calculated [M]905.0, obtained [M+H]905.4.

Example 35. Synthesis of Modified Oligonucleotide According to Embodiment 1 Using Sequential Treatments with the Solutions of 3-Aminopropanol and Phosphoramidite Monomers of Thymidylate Units

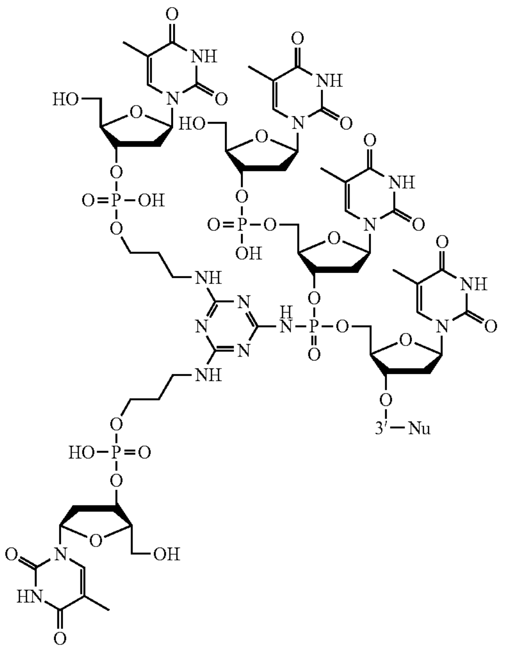

In the example, modified oligonucleotide 5'-d(TT(T)$_2$*TTTTTT) was prepared according to embodiment 1, wherein sequential treatments in item 2 are 1.5 M 3-aminopropanol-1 in dry acetonitrile, 1 hour, 55° C.→condensation of thymidylate unit according to the standard protocol of solid-phase phosphoramidite synthesis.

Molecular Weight:

5'-d(TT(T)$_2$*TTTTTT): calculated [M]3,204.3, obtained [M−H]3,203.6.

Example 36. Synthesis of Modified Oligonucleotide According to Embodiment 1 Using Sequential Treatments with the Solutions of 6-Aminohexanol and Phosphoramidite Monomers of Thymidylate Units

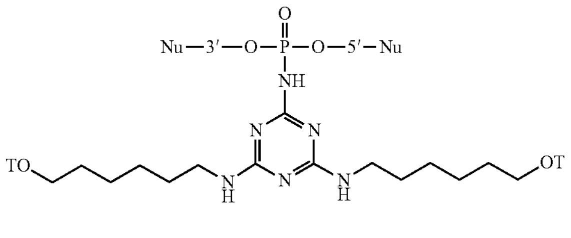

In the example, modified oligonucleotide 5'-d(TT(T)$_2$*TTTTTT) was prepared according to embodiment 1, wherein sequential treatments in item 2 are 1.5 M 6-aminohexanol-1 in dry acetonitrile, 1 hour, 55° C.→condensation of thymidylate unit according to the standard protocol of solid-phase phosphoramidite synthesis.

Molecular Weight:

5'-d(TT(T)$_2$*TTTTTT): calculated [M]3,288.4, obtained [M−H]3,287.7.

Example 37. Synthesis of Modified Oligonucleotide According to Embodiment 1 Using Sequential Treatments with the Solutions of 2-(2-Aminoethoxy)Ethanol and Phosphoramidite Monomers of Thymidylate Units

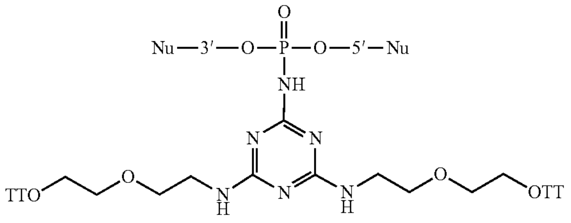

In the example, modified oligonucleotide 5'-d(TTT(T$_2$)$_2$*TTTTT) was prepared according to embodiment 1, wherein sequential treatments in item 2 are 62.5% (vol) 2-(2-aminoethoxy)ethanol in dry acetonitrile, 1 hour, 25° C.→condensation of two thymidylate units according to the standard protocol of solid-phase phosphoramidite synthesis.

Molecular Weight:

5'-d(T*TTTTT): calculated [M]3,872.7, obtained [M−H]3,871.2.

Example 38. Synthesis of Modified Oligonucleotides According to Embodiment 2 Using 2-Azido-4-Dodecylamino-6-Chloro-1,3,5-Triazine with the Methylamine Solution Treatment

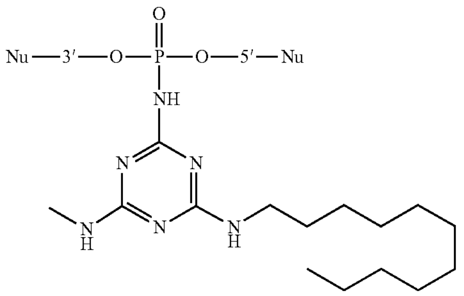

In the example, modified oligonucleotides 5'-d(T*TTTT), 5'-d(TTTT*TTTT) were prepared according to embodiment 2 using 0.1 M solution of 2-azido-4-dodecylamino-6-chloro-1,3,5-triazine in toluene in item 1; item 2 was omitted.

Molecular Weight:

5'-d(T*TTTT): calculated [M]1,749.48, obtained [M+H]1,749.57.

Example 39. Synthesis of Modified Oligonucleotide According to Embodiment 2 Using 2-Azido-4-Dodecylamino-6-Chloro-1,3,5-Triazine with the (N,N-Dimethylamino)Propylamine Solution Treatment

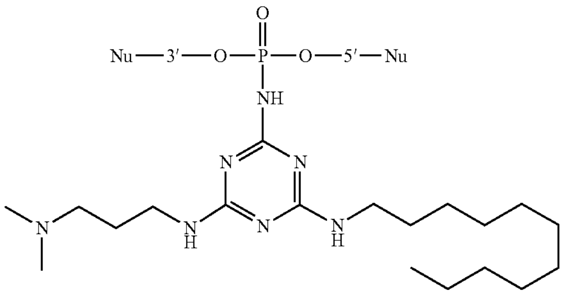

In the example, modified oligonucleotide 5'-d(T*TTTT) was prepared according to embodiment 2 using 0.1 M solution of 2-azido-4-dodecylamino-6-chloro-1,3,5-triazine in toluene in item 1, sequential treatments in item 2 are 10% (vol) (N,N-dimethylamino)propylamine in dry acetonitrile, 1 hour, 25° C.

Molecular Weight:

5'-d(T*TTTT): calculated [M]1,820.61, obtained [M+H] 1,820.59.

Example 40. Synthesis of Modified Oligonucleotide According to Embodiment 2 Using 2-Azido-4-Olelylamino-6-Chloro-1,3,5-Triazine with the Methylamine Solution Treatment

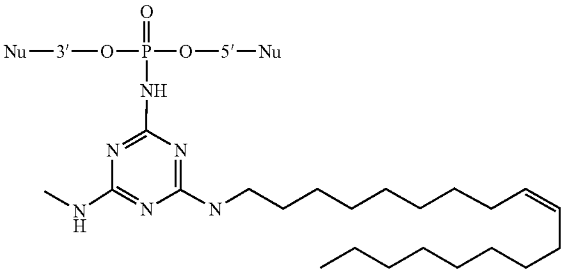

In the example, modified oligonucleotide 5'-d(T*TTTT) was prepared according to embodiment 2 using 0.1 M solution of 2-azido-4-oleylamino-6-chloro-1,3,5-triazine in toluene in item 1; item 2 was omitted.

Molecular Weight:

5'-d(T*TTTT): calculated [M]1,831.65, obtained [M+H] 1,831.30.

Example 41. Synthesis of Modified Oligonucleotide According to Embodiment 2 Using 2-Azido-4-(N-Methyl-N-Octadecyl)Amino-6-Chloro-1,3,5-Triazine with the Methylamine Solution Treatment

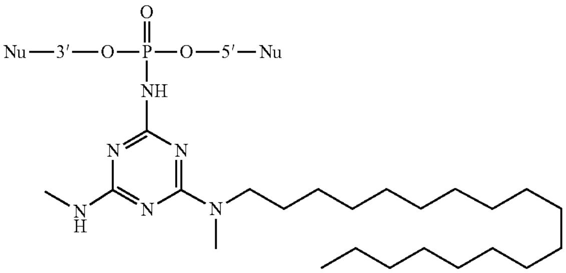

In the example, modified oligonucleotide 5'-d(T*TTTT) was prepared according to embodiment 2 using 0.1 M solution of 2-azido-4-(N-methyl-N-octadecyl)amino-6-chloro-1,3,5-triazine in toluene in item 1; item 2 was omitted.

Molecular Weight:

5'-d(T*TTTT): calculated [M]1,847.67, obtained [M+H] 1,847.59.

Example 42. Synthesis of Modified Oligonucleotide According to Embodiment 3 Using 2-Azido-4,6-Dibutylamino-1,3,5-Triazine

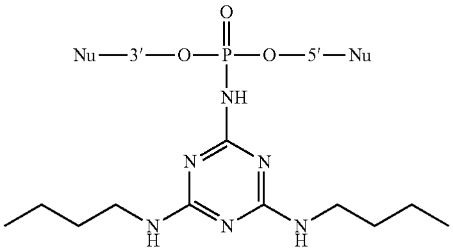

In the example, modified oligonucleotide 5'-d(T*TTTT) was prepared according to embodiment 3 using 0.5 M solution of 2-azido-4-dodecylamino-6-chloro-1,3,5-triazine in DMF in item 1.

Molecular Weight:

5'-d(T*TTTT): calculated [M]1,679.35, obtained [M+H] 1,679.53.

Example 43. Synthesis of Modified Oligoribonucleotides According to Embodiment 1 Using the Piperidine Solution Treatment

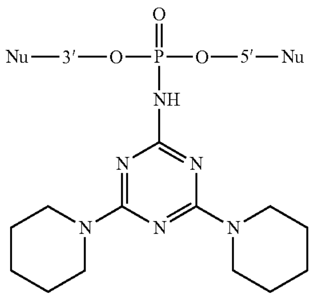

In the example, modified oligonucleotides 5'-A$^m$C$^m$G$^m$U$^m$*U$^m$, 5'-U$^m$U$^m$U$^m$U$^m$*[BHQ], 5'-A$^m$C$^m$G-$^m$U$^m$*[$NH_2$]; herein, $^m$ means 2'-O-methyl nucleotides within the sequence; [BHQ] and [$NH_2$] designate CPG polymer supports with the fluorescence quencher and hexylamine moieties, respectively.

Modified oligonucleotides were prepared according to embodiment 1, wherein sequential treatments in item 2 are 10% (vol) piperidine in dry acetonitrile, 1 hour, 25° C.

Molecular Weights:

5'-A$^m$C$^m$G$^m$U$^m$*U$^m$: calculated [M]1,844.5, obtained [M–H]1,843.5.

5'-U$^m$U$^m$U$^m$U$^m$*[BHQ]: calculated [M]2,017.7, obtained [M–H]2,016.5.

5'-A$^m$C$^m$G$^m$U$^m$*[$NH_2$]: calculated [M]1,703.4, obtained [M–H]1,702.5.

Study of Therapeutic Potential of Modified Oligonucleotides

Figure 3:
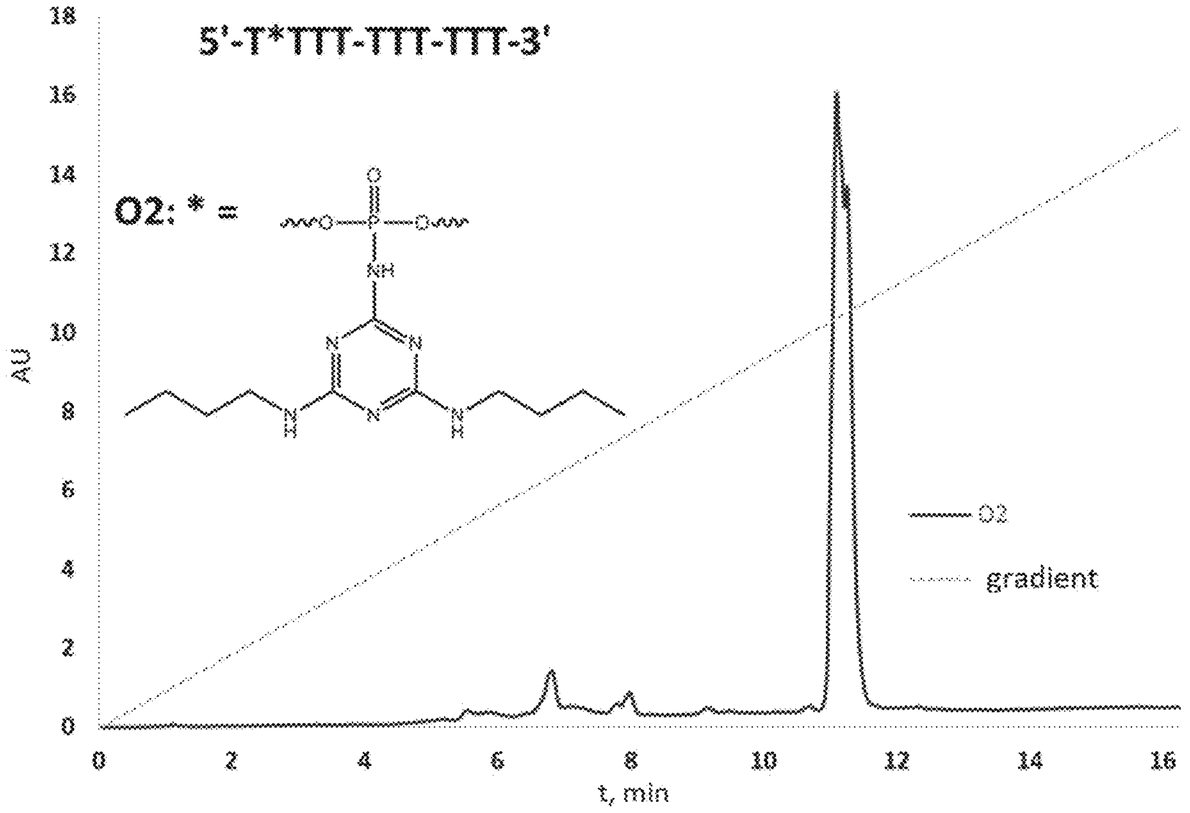
FIG. 3 shows results of chemical stability research for the modified oligonucleotide in alkaline conditions.

Example 44. Study of Chemical Stability of Oligonucleotides Comprising Triazinylamidophosphate Modification Oligonucleotide O2, 5'-d(T*TTTTTTTT), wherein * is an triazinylamidophosphate unit with butyl moieties, was synthesized as defined in Example 10. To study the produced oligonucleotide stability, final deblocking was performed with the concentrated aqueous methylamine solution for 30 min at 65° C. It can be seen from the chromatography profile in FIG. 3 that the reaction does not have any peaks indicating degradation of the produced target product.

To study the oligonucleotide O2 stability, concentrated hydrochloric acid solution was added to the oligonucleotide solution in acidic conditions to achieve the concentration of 0.1 M. In 30, 90, 180, and 780 minutes, equal aliquots of reaction were collected and neutralized by addition of excessive concentrated aqueous ammonia solution. Then aliquots were evaporated and analytical RP-HPLC was performed to estimate the acidic hydrolysis degree of the modified oligonucleotide. Simultaneously, a similar experiment with oligonucleotide Bz 5'-d(T$^b$TTTTTTTTT) was performed, wherein b is a benzylamidophosphate unit.

Figure 4:
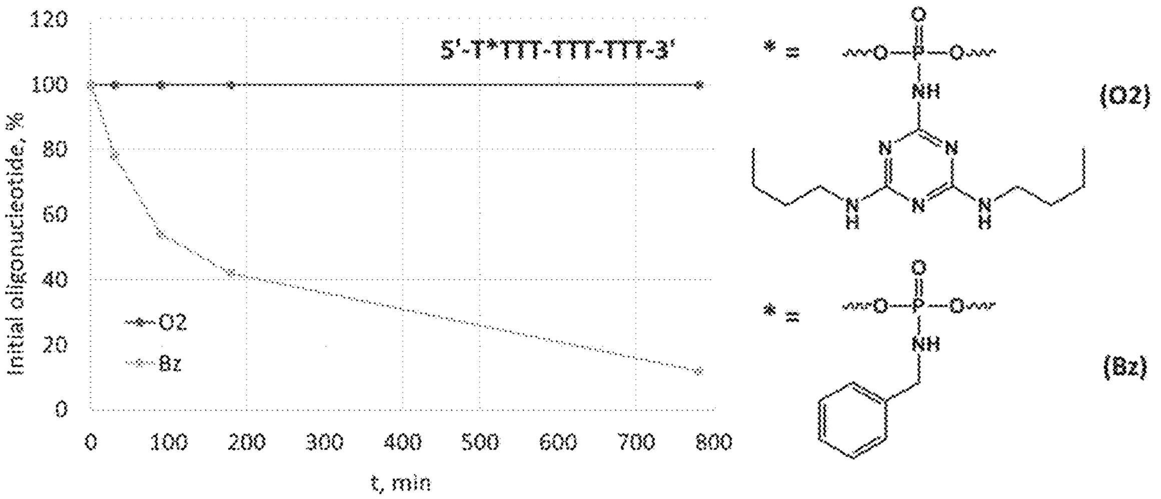
FIG. 4 shows results of chemical stability research for modified oligonucleotides in acidic conditions.

The experiment results provided in FIG. 4 show that the amount of oligonucleotide containing benzylamidophosphate modification (Bz) decreased by more than 60% in three hours, and by more than 80% in 13 hours, relative to the initial amount. Meanwhile, the amount of oligonucleotide containing triazinylamidophosphate modification (O2) did not change throughout the entire experiment. This suggests specific stability of triazinylamidophosphate modification.

Therefore, it was shown that oligonucleotides containing modified phosphate group of Formula (Fx) have a high stability both in alkaline and acidic conditions.

Example 45. Testing Modified Oligonucleotide Resistance to Nucleases from Whole-Cell HEK293T and T98G Extracts To study enzymatic stability, oligonucleotide 5'-[FAM]-CTGACTATGAAGTAT*T-3' was used, wherein * is a position of triazinylamidophosphate unit containing butyl moieties.

Control unmodified oligonucleotide 5'-[FAM]-CTGACTATGAAGTATT-3' was used for reference.

Reactions contained 1 mg/ml proteins of cultured T98G or HEK293T human cell extract, 0.1 μM of one of the said oligonucleotides, and buffer components 10 mM MgCl2, 50 mM tris HCl (pH=8.0), 50 mM NaCl. Reactions were performed for 7.5 and 15 minutes for each extract at 37° C. Reactions were stopped by introducing EDTA until final concentration of 20 mM is achieved. After that, aliquots were analyzed using electrophoresis in PAGE in denaturating conditions [43].

Figure 5:
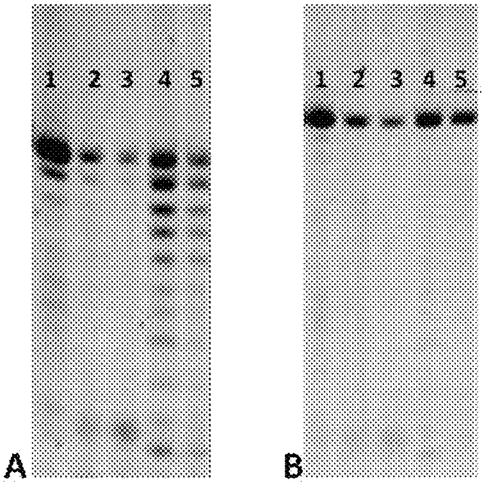
FIG. 5 shows results of enzymatic stability research of triazinylphosphoramidate modified oligonucleotides.

Experiment results are shown in FIG. 5. Panel A provides an electropherogram obtained for unmodified oligonucleotide, and Panel B provides an electropherogram obtained for modified oligonucleotide. The following designations are used for each panel: 1—control oligonucleotide solution; 2—HEK293T, 7.5 min; 3—HEK293T, 15 min; 4—T98G, 7.5 min; 5—T98G, 15 min.

As it can be seen from experimental data, introduction of even one triazinylamidophosphate modification significantly enhances enzymatic stability of modified oligonucleotide in both cell extracts.

Thus, it was shown that oligonucleotides containing modified phosphate group of Formula (Fx) have a high stability in biological media.

Example 46. Study of the HEK293T and T98G Cell Transfection Efficiency with the OSN4F Oligonucleotide by Flow Cytofluorometry To study cell penetration efficiency, oligonucleotide 5'-[FAM]-CTGACTATGAAGTAT*T-3' (OSN4F) was used, wherein * is a position of thiazinylamidophosphate unit carrying two dodecyl moieties, and control unmodified oligonucleotide 5'-[FAM]-CTGACTATGAAGTATT-3' (OSNF).

Figure 6:
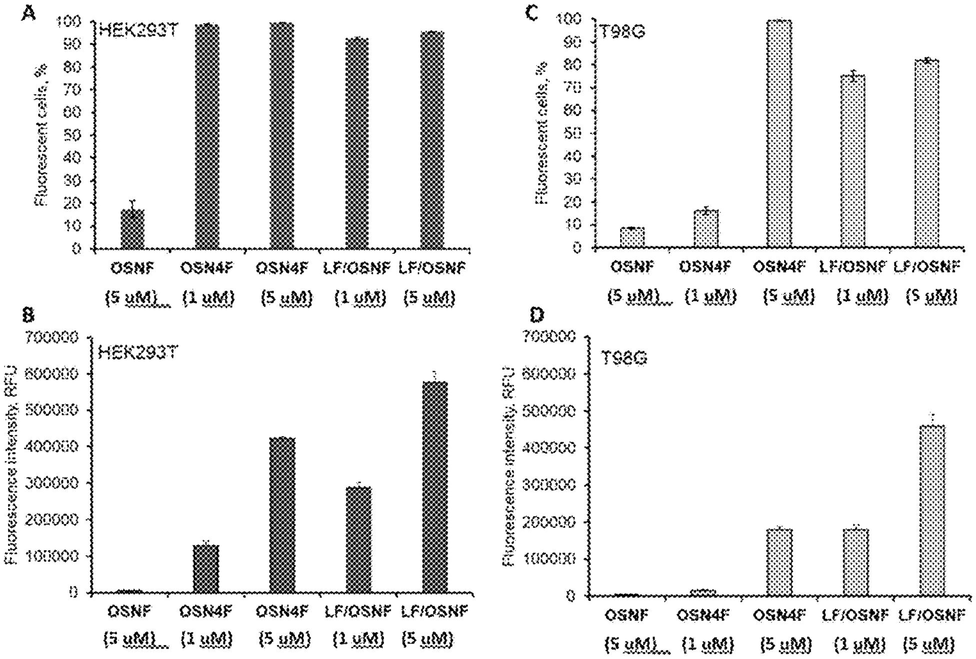
FIG. 6 shows results of penetration efficiency research of the modified oligonucleotide into HEK293T, T98G human cell cultures.

Cultured HEK293T and T98G human cells were plated onto the wells of a 24-well microplate in a concentration 20x104 cells/well (HEK293T) or 12x104 cells/well (T98G) in 500 μl/well IMDM media comprising 10% FBS and 1% solution of antibiotic and antimycotic agents (10 mg/ml streptomycin, 10,000 U/ml penicillin, and 25 mg/ml amphotericin (IMP Biomedicals, Germany) (hereinafter, the complete medium), and incubated for 18 hrs to provide cell attachment. Furthermore, cell medium was replaced with 200 μl/well IMDM medium in the absence of serum and antibiotic agents. Oligonucleotides (OSNF, OSN4F) were dissolved in Opti-MEM and added to the cells until the final concentration of 1 or 5 μM (50 μl/well) was achieved. As a positive control, cell transfection with control oligonucleotide OSNF was used with commercially available transfectant Lipofectamine 2000 (Thermo Fisher Scientific, USA). Transfection was performed according to the manufacturer's protocol. The cells were incubated for 4 hours in standard conditions. After incubation, the cells were removed from the culture plastic using 2% trypsin (MP Biomedicals, USA) resuspended in complete medium IMDM, spin at 200 g for 5 min, washed with PBS and fixed in 2% formaldehyde in PBS (10 min, room temperature). The cells were analyzed on a flow cytometer NovoCyte 3000 (ACEA Biosciences, USA). All experimental points were performed in three replicates for statistical analysis. Oligonucleotide penetration efficiency was characterized by two indicators: % of fluorescent cells in a population and average intensity of cell fluorescence in a sample, which were measured using flow cytometry in 4 hours after transfection. The experiment results are provided in FIG. 6. Histograms A and C show % of fluorescent cells, histograms B and D show average fluorescence intensity. RFU means relative fluorescence units, LF means Lipofectamine 2000. The data are shown as average±standard deviation.

The provided data show that oligonucleotide OSN4F in the absence of an additional transfection agent efficiently penetrates the HEK293T cells both in terms of the number of transfected cells and the fluorescence intensity. At that, the OSN4F penetration efficiency was comparable with the penetration efficiency of control oligonucleotide OSNF in the presence of commercial transfection agent Lipofectamine 2000.

Histograms C and D show that in the absence of additional transfectants, modified oligonucleotide OSN4F penetrates the T98G cells more efficiently than the control oligonucleotide. However, note that, for the T98G glioblastoma cells, oligonucleotide penetration efficiency is reduced relative to the HEK293K kidney cells, while, at the same time, dose-dependent trend of enhancing the transfection efficiency was maintained. A reason of difference in the oligonucleotide penetration efficiency is specifics of the HEK293T and T98G cell membrane composition caused by different cell types.

Thus, modified oligonucleotide OSN4F capable of efficiently penetrating the cultured human cells HEK293T and T98G in the absence of additional transfection agents. At that, its penetration efficiency is much more than of the control unmodified oligonucleotide. It suggests positive impact of the said modification on the ability to penetrate human cells.

Importantly, the penetration efficiency of the modified oligonucleotide OSN4F, without any additional transfection agents is comparable with the penetration efficiency of the control unmodified oligonucleotide using common transfection agent Lipofectamine2000.

Differences in penetration efficiency of the modified oligonucleotide OSN4F into various cell types indicate penetration selectivity which may be caused by specifics of the cell membrane composition. Such selectivity, together with dose-dependent nature of the oligonucleotide penetration efficiency, provides the development of highly specific therapeutic drugs.

Example 46. Confocal Microscopy Data on Penetration of a Modified Oligonucleotide into the Human Cells In this study, oligonucleotide 5'-[FAM]-CTGACTATGAAGTAT*T-3' (OSN4F) was used, wherein * is a position of triazinylamidophosphate unit having two dodecyl moieties.

Cultured human cells HEK293T were plated on slides placed to the wells of the 24-well microplate, in a concentration of 6×104 cells/well in a complete IMDM medium and incubated at 37° C. in 5% CO2 for 12 to 18 hours to provide cell attachment. Then, the medium was replaced to IMDM, in the absence of serum and antibiotic agent, which comprises OSN4F at a concentration of 1 μM. The cells were incubated in the presence of oligonucleotide at 37° C. in 5% CO2 for 4 hours. After the incubation, the cover slides with cells were placed onto the slides into a drop of ProLong Glass Antifade Mounting Medium (ThermoFisher Scientific, USA) containing NucBlue for staining cell nuclei, and the slides were incubated in a horizontal position in darkness at room temperature for 12 hours to provide medium polymerization.

Intracellular location of oligonucleotide OSN4F was studied using confocal microscope LSM710 (Zeiss, Germany) with the plan-apochromat 63×/1.40 Oil DIC M27 (Zeiss, Germany) lens and two channels, blue and green. Fluorescence in a blue channel at exciting laser wavelength of 405 nm corresponded to NucBlue (cell nuclei staining); green channel at exciting laser wavelength of 488 nm corresponded to fluorescence of oligonucleotide OSN4F labelled with a 6-carboxyfluorescein moiety.

Figure 7:
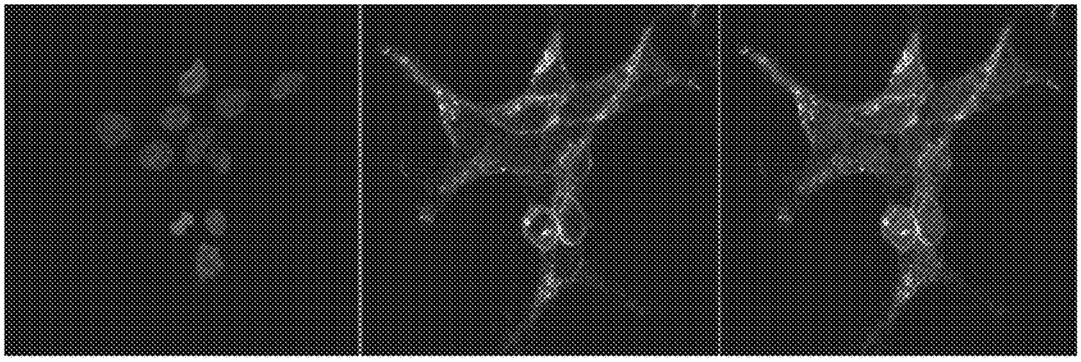
FIG. 7 shows results of laser confocal microscopy of human cells transfected by the modified oligonucleotide.

FIG. 7 shows typical series of microphotographs of the HEK293T cells transfected by modified oligonucleotide OSN4F. The left photo shows cell nuclei, the center photo shows OSN4F (center), the right photo shows channel overlapping.

Confocal microscopy data show that modified oligonucleotide OSN4F efficiently penetrates human cells without adhering to cell membrane but rather positioning in the cytoplasm and various cell compartments. This enables modified oligonucleotides to achieve a wide range of diverse intracellular molecular targets.

Example 47. Comparing Human Cell Penetration Efficiency of Oligonucleotides Comprising Lipophilic Moieties within Various Modification Backbones The study was performed on the cultured human cells HEK293T. The cells were handled and transfection conditions were as described in Example 45.

To study the modification backbone effect on the penetration efficiency, the following modified oligonucleotides were used: OS4F—with triazinylamidophosphate modification; PGO—with phosphoryl guanidine modification; PN—with two amidophosphate modifications; and ODF—with two non-nucleotide units. At that, all oligonucleotides contained two dodecyl moieties.

| | |
|---|---|
| OSN4F | 5'-[FAM]CTGACTATGAAGTAT*T-3' |
| PGO | 5'-[FAM]CTGACTATGAAGTAT*T-3' |
| PN | 5'-[FAM]GGTAGCAAGTCGAGA*C*T-3' |
| ODF | 5'-[FAM]CTGACTATGAAGTAT[D][D]T-3' |

Figure 8:
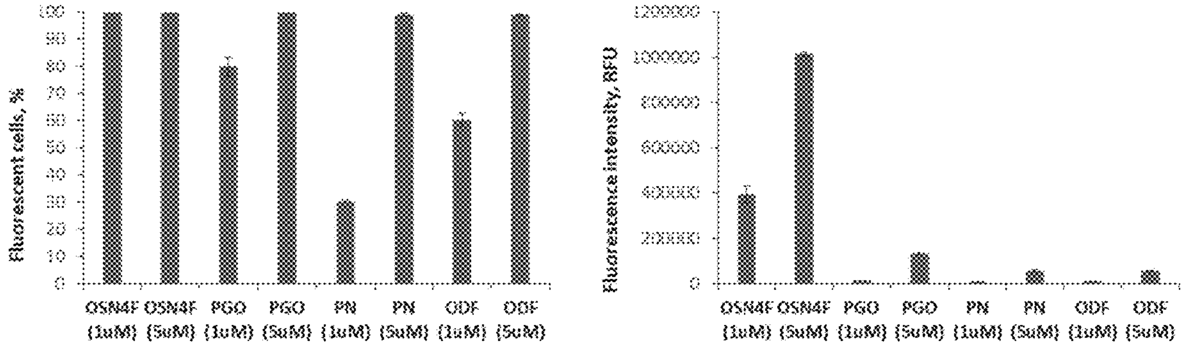
FIG. 8 shows results of penetration efficiency research of oligonucleotides containing dodecyl moieties within modifications with various backbones to the human cells.
Figure 8:
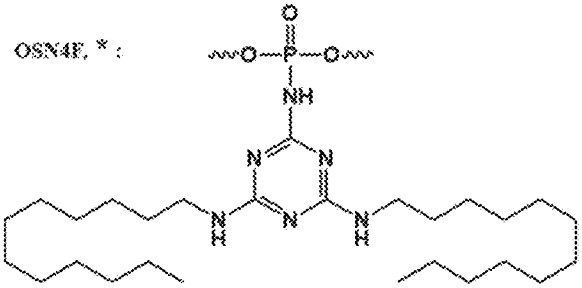
Figure 8:
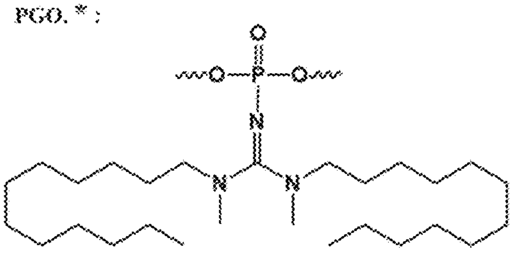
Figure 8:
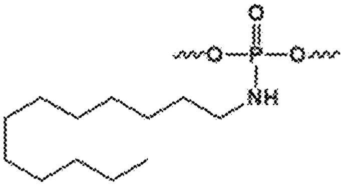
Figure 8:
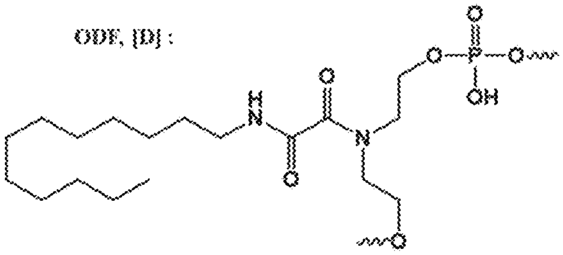

The experiment results are provided in FIG. 8. Cell fluorescence percent (left) and average fluorescence intensity (right) were measured using flow cytometry in 4 hours after transfection. RFU means relative fluorescence units, LF means Lipofectamine 2000. The data are shown as average±standard deviation.

The provided data show that with the concentration of 1 μM oligonucleotide OSN4F efficiently penetrates the cells. In this case, its penetration rate significantly higher than in other oligonucleotides used. When looking at the fluorescence intensity, it becomes clear that oligonucleotide OSN4F penetrates cells in larger amounts than other oligonucleotides.

Note that all oligonucleotides studied herein carry the same amount of lipophilic dodecyl moieties. It means that the triazinylamidophosphate backbone determining attribution to the claimed compound class provides improved cell penetration.

Example 48. Study of Penetration Efficiency of Modified Oligoribonucleotides to the Human Cells Penetration efficiencies of modified oligoribonucleotides (ON1, ON2, and ON3) were compared on a human hepatocellular carcinoma cell line (HepG2). The cells were cultured in a 24-well microplate in a MEM medium containing 10% FBS, 1 mM sodium pyruvate, and a mix of antibiotic agents 100 IU/ml (penicillin/streptomycin). Upon achieving 70% confluency, the medium was removed, and the monolayer was washed with the sodium phosphate buffer to remove serum traces, and then the OptiMEM medium containing a conjugate in a concentration of 1 or 2.5, or 5 μM was poured to the cell culture. The cells in the presence of the oligoribonucleotide conjugate were incubated for 12 hours in a CO2 incubator. Then the medium was replaced with MEM, and the cells were incubated in a CO2 incubator for another 2 hours to completely degrade the conjugate adhered to the cell surface. Oligoribonucleotide cell penetration efficiency was evaluated by flow cytofluorometry; for this, before the assay, the cells were washed by sodium phosphate buffer and detached from the microplate surface using the Trypsin EDTA solution according to the standard protocol. The assay was performed in the DME medium which does not contain phenol red dye.

ON1 5'-rGrArGrCrCrCrCrCrUrArCrArGrGrGrCrUrCrUrUT*T-FAM-3'

ON2 5'-rGrArGrCrCrCrCrCrUrArCrArGrGrGrCrUrCrUrUT*T-FAM-3'

ON3 5'-rGrArGrCrCrCrCrCrUrArCrArGrGrGrCrUrCrUrUT*T-FAM-3'

ON1

(*) =
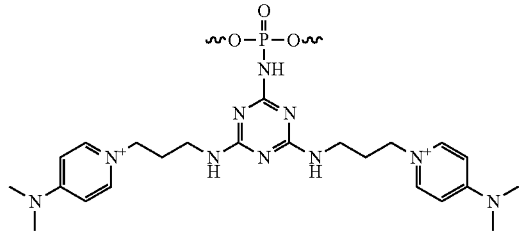

-continued

ON2

(*) =
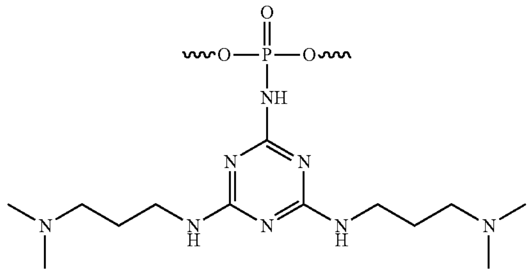

ON3

(*) =
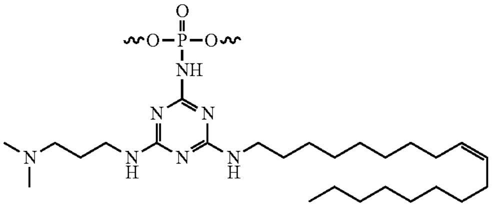

Figure 9:
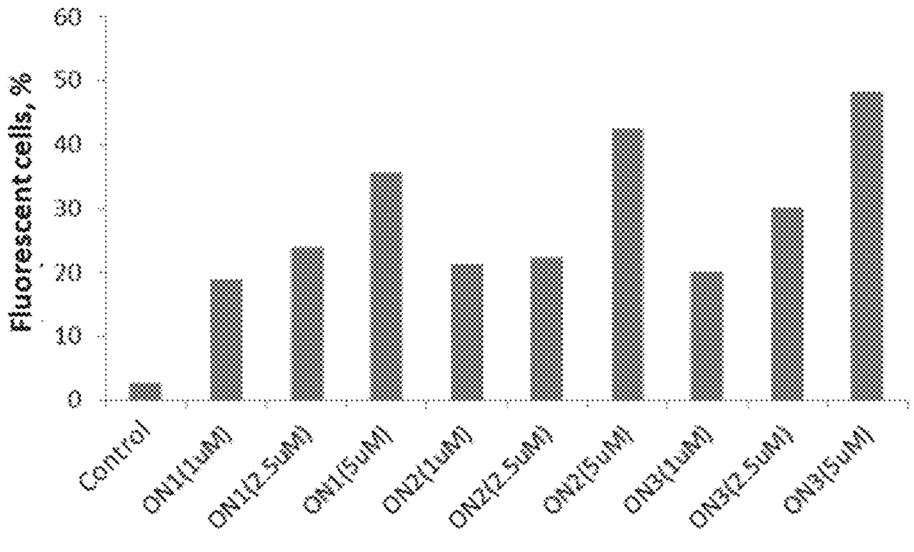
FIG. 9 shows results of penetration efficiency research of modified oligoribonucleotides to the HEPG2 human cells.

The experiment results are provided in FIG. 9. It can be seen that all modified oligoribonucleotides studied herein capable of penetrating the human cells. Wherein the cell penetration efficiency of modified oligoribonucleotides is significantly higher than in controls.

Therefore, the performed assay has shown that different representatives of the claimed compound class have a property of penetrating human cells in the absence of transfection agents.

Example 49. Study of Complementary Complex Formation Efficiency Using Modified Oligonucleotides The complementary complex formation efficiency was studied for modified oligonucleotides containing triazinylamidophosphate group with butyl (OSNF) and dodecyl amine (OSN4, ISN4) moieties as well as unmodified oligonucleotides (OSNF, ISN).

Oligonucleotides OSN1F, OSN4F, and OSNF were mixed with complementary oligonucleotide ISN. Oligonucleotides OSN1F and OSNF were mixed with modified complementary oligonucleotide ISN4. They were mixed in the PBS phosphate buffer at a concentration of oligonucleotides of 2.5 μM. The experiment results of measuring melting points of the produced complementary complexes are provided in the following table.

| Oligonucleotide name | Sequence (5'-3') | Complementary complex | Melting point (° C.) |
|---|---|---|---|
| OSNF | [FAM]CTGACTATGAAGTATT | OSNF/ISN | 50 |
| OSN1F | [FAM]CTGACTATGAAGTAT$^{b}$T | OSN1F/ISN | 49.6 |
| OSN4F | [FAM]CTGACTATGAAGTAT*T | OSN4F/ISN | 49.2 |
| ISN | AATACTTCATAGTCAG | OSNF/ISN4 | 53.6 |
| ISN4 | AATACTTCATAGTCAGT*T | OSN1F/ISN4 | 52.6 |

It can be seen that, in all cases, modified oligonucleotides capable of efficiently binding to complementary oligonucleotides. In this case, melting points of the formed complementary complexes differ only slightly from melting points of complementary complexes formed by oligonucleotides which do not contain triazine modification (OSNF/ISN).

The provided data show that independently of the size of substituents at the triazine group, in a complementary complex, upon formation of complexes with the complementary portions the triazine group becomes exposed outwardly from the double helix and, therefore, does not affect the complementary interaction of nucleobases inside of it.

It suggests that the phosphate group of Formula (Fx) does not significantly affect the ability of oligonucleotides to form strong and selective complementary complexes with a biological target.

Example 50. Cytotoxicity Study of Modified Oligonucleotides

Cytotoxicity of oligonucleotide OSN4F was studied on cell cultures HEK293T and T98G in real time using xCELLigence (ACEA Biosciences, USA), for 24 hours. The cells were plated on 16-well E-microplates with a density of 105 cells/well in 150 μl/well of the complete IMDM medium and incubated under standard conditions for 20 hours to provide cell attachment to the microplate bottom. The medium was then replaced with 150 μl/well of the IMDM medium containing 10% FBS and 0.5, 1, 2.5, 5, 10, 20, 50 μM oligonucleotide OSN4F. The cells were incubated for 24 hours under standard conditions. Cell indices were measured every 30 min. Dose-dependent cell survival curves were plotted using the MS Excel software for a timepoint o 24 hours after the oligonucleotide addition to the cells. IC50 values were calculated as a concentration of oligonucleotide required to reduce cell index by 50% relative to the control cells incubated in the absence of oligonucleotide.

Figure 10:
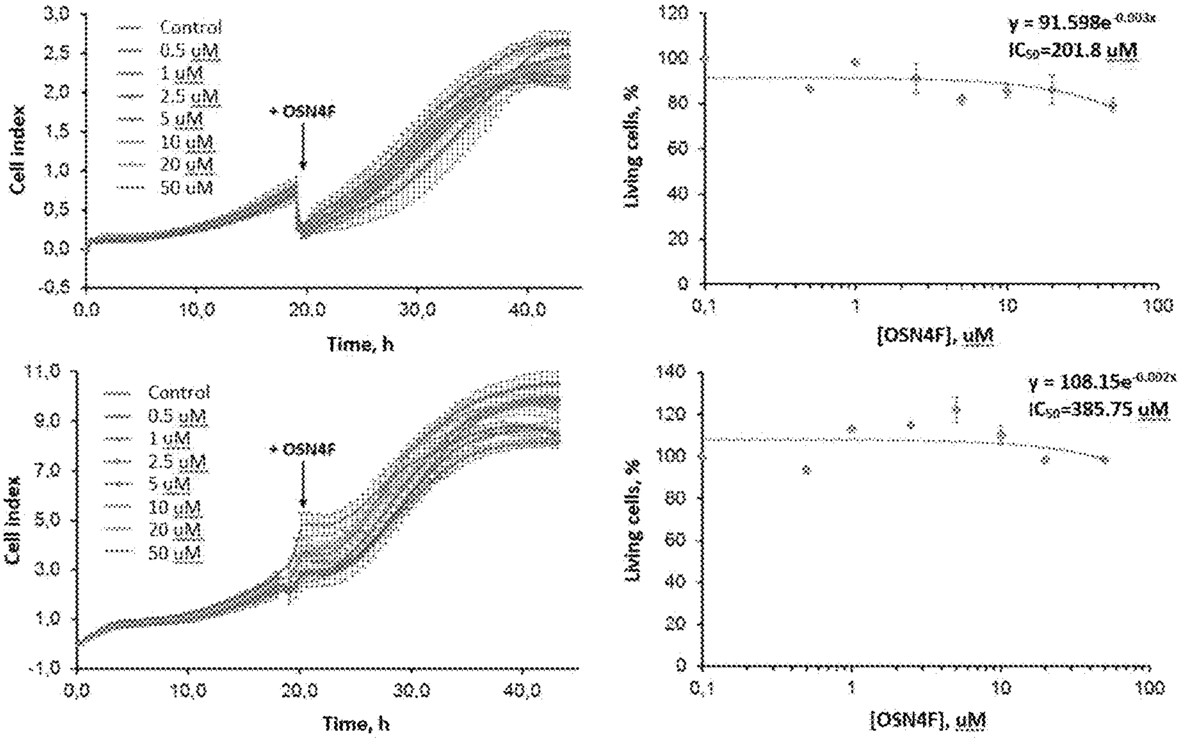
FIG. 10 shows results of cytotoxicity study of modified oligonucleotides.

The experiment results are provided in FIG. 10. It can be seen that oligonucleotide OSN4F is non-toxic to the HEK293T and T98G cells (IC50 of 201.8 μM and 385.8 μM, respectively). The calculated IC50 values significantly exceed typical concentrations of therapeutic oligonucleotides (1 to 5 μM).

Experimental data show that the oligonucleotide modified according to the present invention has a low toxicity to human cells.

REFERENCES

1. Duca M, Vekhoff P, Oussedik K, Halby L, Arimondo P B. The triple helix: 50 years later, the outcome. Nucleic Acids Res. 2008; 36:5123-5138.
2. Nielsen P E. Sequence-selective targeting of duplex DNA by peptide nucleic acids. Curr Opin Mol Ther. 2010; 12:184-191.
3. Zamecnik P C, Stephenson M L. Inhibition of Rous sarcoma virus replication and cell transformation by a specific oligodeoxynucleotide. Proc Natl Acad Sci USA. 1978; 75:280-284.
4. Lee J F, Stovall G M, Ellington A D. Aptamer therapeutics advance. Curr Opin Chem Biol. 2006; 10:282-9.
5. Crooke S T. Progress in antisense technology: The end of the beginning. Methods Enzymol. 2000; 313:3-45.
6. Xu Z J, Yang L F, Sun L Q, Cao Y. Use of DNAzymes for cancer research and therapy. Chinese Sci Bull. 2012; 57:3404-3408.
7. Pérez B, Rodríguez-Pascau L, Vilageliu L, Grinberg D, Ugarte M, Desviat L R. Present and future of antisense therapy for splicing modulation in inherited metabolic disease. J Inherit Metab Dis. 2010; 33:397-403.
8. Ruckman J, Green L S, Beeson J, Waugh S, Gillette W L, Henninger D D, et al. 2'-fluoropyrimidine RNA-based aptamers to the 165-amino acid form of vascular endothelial growth factor (VEGF165): Inhibition of receptor binding and VEGF-induced vascular permeability through interactions requiring the exon 7-encoded domain. J Biol Chem. 1998; 273:20556-67.
9. Lamond A I, Sproat B S. Antisense oligonucleotides made of 2'-O-alkylRNA: their properties and applications in RNA biochemistry. FEBS Lett. 1993; 325:123-7.
10. Chi K N, Eisenhauer E, Fazli L, Jones E C, Goldenberg S L, Powers J, et al. A phase I pharmacokinetic and pharmacodynamic study of OGX-011, a 2'-methoxyethyl antisense oligonucleotide to clusterin, in patients with localized prostate cancer. J Natl Cancer Inst. 2005; 97:1287-96.
11. Kaur H, Babu B R, Maiti S. Perspective on chemistry and therapeutic applications of locked nucleic acid (LNA). Chem Rev. 2007; 107:4672-97.
12. Jäger A, Engels J. Synthesis of deoxynucleoside methylphosphonates via a phosphonamidite approach. Tetrahedron Lett. 1984; 25:1437-40.
13. Hau J F, Asseline U, Thuong N T. Octathymidylates involving alternating neopentylphosphothionotriester-phosphodiester linkages with controlled stereochemistry at the modified P-center. Tetrahedron Lett. 1991; 32:2497-8.
14. Jäger A, Levy M J, Hecht S M. Oligonucleotide N-Alkylphosphoramidates: Synthesis and Binding to Polynucleotides. Biochemistry. 1988; 27:7237-7246.
15. Egholm M, Buchardt O, Nielsen P E, Berg R H. Peptide Nucleic Acids (PNA). Oligonucleotide Analogues with an Achiral Peptide Backbone. J Am Chem Soc. 1992; 114: 1895-1897.
16. Summerton J, Weller D. Morpholino antisense oligomers: Design, preparation, and properties. Antisense Nucleic Acid Drug Dev. 1997; 7:187-95.
17. Spurgers K B, Sharkey C M, Warfield K L, Bavari S. Oligonucleotide antiviral therapeutics: Antisense and RNA interference for highly pathogenic RNA viruses. Antiviral Res. 2008; 78:26-36.
18. Berkhout B, Haasnoot J. Nucleic acids-based therapeutics in the battle against pathogenic viruses. Handb Exp Pharmacol. 2009; 189:243-63.
19. Ahn D G, Lee W, Choi J K, Kim S J, Plant E P, Almazin F, et al. Interference of ribosomal frameshifting by antisense peptide nucleic acids suppresses SARS coronavirus replication. Antiviral Res. 2011; 91:1-10.
20. Lee C H, Kim J H, Lee S W. Prospects for nucleic acid-based therapeutics against hepatitis C virus. World J Gastroenterol. 2013; 19:8949-62.
21. H. F. Rosenberg, J. B. Domachowske. Inflammatory Responses to Respiratory Syncytial Virus (RSV) Infection and the Development of Immunomodulatory Pharmacotherapeutics. Curr Med Chem. 2012; 19:1424-31.

22. Choi J H, Croyle M A. Emerging Targets and Novel Approaches to Ebola Virus Prophylaxis and Treatment. BioDrugs [Internet]. 2013; 27:565-583. Available from: https://www.ncbi.nlm.nih.gov/pmc/articles/PMC3624763/pdf/nihms412728.pdf
23. Maepa M B, Roelofse I, Ely A, Arbuthnot P. Progress and prospects of anti-HBV gene therapy development. Int J Mol Sci. 2015; 16:17589-610.
24. Asha K, Kumar P, Sanicas M, Meseko C, Khanna M, Kumar B. Advancements in Nucleic Acid Based Therapeutics against Respiratory Viral Infections. J Clin Med. 2018; 8:6.
25. Zhang K, Zheludev I N, Hagey R J, Teng M, Wu P, Haslecker R, et al. Cryo-electron Microscopy and Exploratory Antisense Targeting of the 28-kDa Frameshift Stimulation Element from the SARS-CoV-2 RNA Genome. bioRxiv [Internet]. 2020; Available from: https://doi.org/10.1101/2020.07.18.209270
26. Sharad S. Antisense Therapy: An Overview. Intech [Internet]. 2016. p. 1-11. Available from: https://www.intechopen.com/books/advanced-biometric-technologies/liveness-detection-in-biometrics
27. Miller P S, Yano J, Yano E, Carroll C, Jayaraman K, Ts'o POP. Nonionic Nucleic Acid Analogues. Synthesis and Characterization of Dideoxyribonucleoside Methylphosphonates. Biochemistry. 1979; 18:5134-43.
28. Stec W J, Zon G, Egan W, Stec B. Automated Solid-Phase Synthesis, Separation, and Stereochemistry of Phosphorothioate Analogues of Oligodeoxyribonucleotides. J Am Chem Soc. 1984; 106:6077-6079.
29. Burgers P M J, Eckstein F. Diastereomers of S'-O-Adenosyl S'-O-Uridyl Phosphorothioate: Chemical Synthesis and Enzymatic Properties. Biochemistry. 1979; 18:592-596.
30. Seeberger P H, Caruthers M H, Yau E. 2'-Deoxynucleoside Dithiophosphates: Synthesis and Biological Studies. J Am Chem Soc. 1995; 117:1472-1478.
31. Hall A H S, Wan J, Spesock A, Sergueeva Z, Shaw B R, Alexander K A. High potency silencing by single-stranded boranophosphate siRNA. Nucleic Acids Res. 2006; 34:2773-81.
32. Hogrefe R I, Vaghefi M M, Reynolds M A, Young K M, Arnold U. Deprotection of methylphosphonate oligonucleotides using a novel one-pot procedure. Nucleic Acids Res. 1993; 21:2031-2038.
33. Reynolds M A, Hogrefe R I, Jaeger J A, Schwartz D A, Riley T A, Marvin W B, et al. Synthesis and thermodynamics of oligonucleotides containing chirally pure R(p) methylphosphonate linkages. Nucleic Acids Res. 1996; 24:4584-4591.
34. Rait V, Sergueev D, Summers J, He K, Huang F, Krzyzanowska B, et al. Boranophosphate nucleic acids—A versatile DNA backbone. Nucleosides and Nucleotides. 1999; 18:1379-80.
35. Hall A H S, Wan J, Shaughnessy E E, Shaw B R, Alexander K A. RNA interference using boranophosphate siRNAs: Structure-activity relationships. Nucleic Acids Res. 2004; 32:5991-6000.
36. Letsinger R L, Singman C N, Histand G, Salunkhe M. Cationic oligonucleotides. J Am Chem Soc. 1988; 110: 4470-1.
37. Laurent A, Naval M, Debart F, Vasseur J J, Rayner B. Chiral and steric effects in the efficient binding of α-anomeric deoxyoligonucleoside N-alkylphosphoramidates to ssDNA and RNA. Nucleic Acids Res. 1999; 27:4151-4159.
38. Maier M A, Guzaev A P, Manoharan M. Synthesis of chimeric oligonucleotides containing phosphodiester, phosphorothioate, and phosphoramidate linkages. Org Lett. 2000; 2:1819-22.
39. Aboul-Fadl T. Antisense Oligonucleotides: The State of the Art. Curr Med Chem. 2005; 12:2193-214.
40. Alter J, Lou F, Rabinowitz A, Yin H F, Rosenfeld J, Wilton S D, et al. Systemic delivery of morpholino oligonucleotide restores dystrophin expression bodywide and improves dystrophic pathology. Nat Med. 2006; 12:175-7.
41. Wu B, Moulton H M, Iversen P L, Jiang J, Li J, Li J, et al. Effective rescue of dystrophin improves cardiac function in dystrophin-deficient mice by a modified morpholino oligomer. Proc Natl Acad Sci USA. 2008; 105: 14814-9.
42. Sinha N D, Biernat J, Mcmanus J, Köster H. Polymer support oligonucleotide synthesis XVIII: Use of β-cyanoethyi-N,N-dialkylamino-/N-morpholino phosphoramidite of deoxynucleosides for the synthesis of DNA fragments simplifying deprotection and isolation of the final product. Nucleic Acids Res. 1984; 12:4539-4557.
43. Maniatis T, Fritsch E F, Sambrook J. Molecular Cloning: a laboratory manual. 2nd edition. Cold Spring Harb, New York. 1989;

What is claimed is:

1. A compound of Formula F0:

(F0)

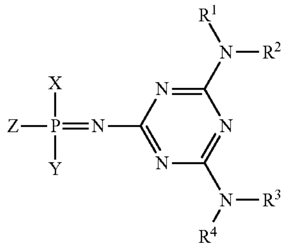

wherein,

Z is selected from the group consisting of: —OH, —SH, —SeH, —$NHR^N$, —O—PG, —S—PG, —Se PG, or —$N(PG)R^N$, X and Y are defined as either:

(i) X is selected from the group consisting of the 5'-O end of a nucleoside or the 5'-O end of an oligonucleotide, and Y is selected from the group consisting of the 3'-O end of a nucleoside or the 3'O end of an oligonucleotide, —H, —OH, —SH, —$NHR^N$, —O—PG, —S—PG, a linker, a monophosphate, or a diphosphate, or (ii) Y is selected from the group consisting of the 5'-O end of a nucleoside or the 5'-O end of an oligonucleotide, and X is selected from the group consisting of the 3'-O end of a nucleoside or the 3'-O end of an oligonucleotide, —H, —OH, —SH, —$NHR^N$, —O—PG, —S—PG, a linker, a monophosphate, or a diphosphate, $R^1$, $R^2$, $R^3$, $R^4$ are selected from the group consisting of of —H, —$C_{1-18}$alkyl, —$C_{2-18}$alkenyl, $C_{2-18}$alkynyl, and —$C_{6-18}$aryl, which may include the groups of —NH—, —N<, —O—, —NHC(O)—, —$NHS(O)_2$, —$N(CH_2CH_2)_2N$—, and/or a group of Formula 1, and terminate in the groups of —$NR_2$, —OR, —SR, —OC(O)R, —NHC(O)R, —C(O)OR, —C(O)NHR, —N═$C(N(R_2))_2$, —S(O)R, —$S(O)_2R$, —$S(O)_2NR_2$, —CN, —Cl, —Br, —I, —F, $N_3$, a group of Formula 2 or a group of Formula 3, or $R^1$ is absent and $R^2$ is ═C—$(NR_2)_2$, or $R^3$ is absent and $R^4$ is ═C—$(NR_2)_2$, or $R^1$ and $R^2$; $R^3$ and $R^4$; $R^5$ and $R^6$; $R^7$ and $R^8$ together with the atom to which they are bound form a 5-8-membered heterocyclic substituent selected from the group consisting of N-pyrrolidinyl, N-piperidinyl, N-azepanyl, N-azocanyl, or N-piperazinyl, Formula 1

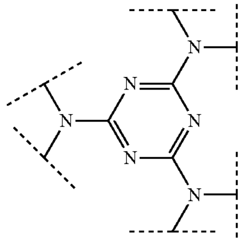

-continued

Formula 2

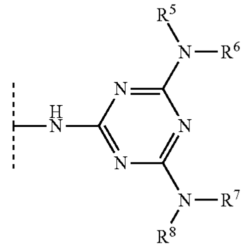

Formula 3

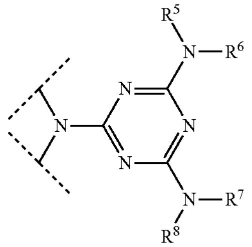

R5, R6, R7, R8 are selected from the group consisting of —H, —$C_{1-18}$alkyl, —$C_{2-18}$alkenyl, $C_{2-18}$alkynyl, and —$C_{6-18}$aryl, which may include the groups of —NH—, —N<, —O—, —NHC(O)—, —$NHS(O)_2$, —$N(CH_2CH_2)N$—, and terminate in the groups of —$NR_2$, —OR, —SR, —OC(O)R, —NHC(O)R, —C(O)OR, —C(O)NHR, —N═$C(N(R^2))_2$, —S(O)R, —$S(O)_2R$, —$S(O)_2NR_2$, —CN, —Cl, —Br, —I, —F, $N_3$, R is a substituent selected from the group consisting of —H, —$C_{1-18}$alkyl, —$C_{2-18}$alkenyl, $C_{2-18}$alkynyl, and —$C_{6-18}$aryl, which may include the groups of —NH—, —N<, —O—, —NHC(O)—, —$NHS(O)_2$, —$N(CH_2CH_2)N$—, and terminate in the groups of —$NR^N{}_2$, —$OR^N$, —$SR^N$, —$OC(O)R^N$, —$NHC(O)R^N$, —$C(O)OR^N$, —$C(O)NHR^N$, —N═$C(N(R^N{}_2))_2$, —$S(O)R^N$, —$S(O)_2R^N$, —$S(O)_2NR^N{}_2$, —CN, —Cl, —Br, —I, —F, $N_3$, PG is a protecting group, and $R^N$ is —H or $C_{1-4}$alkyl.

2. The compound according to claim 1, wherein R1, R2, R3, R4 are selected from the group consisting of —H, —$C_{1-18}$alkyl, —$C_{2-18}$alkenyl, $C_{2-18}$alkynyl, and —$C_{6-18}$ aryl, which may include the groups of —NH—, —N<, —O—, —NHC(O)—, —$NHS(O)_2$, —$N(CH_2CH_2)_2N$—, and/or a group of Formula 1.

3. The compound according to claim 1, wherein R1, R2, R3, R4 are selected from the group consisting of —H, —$C_{1-18}$alkyl, —$C_{2-18}$alkenyl, $C_{2-18}$alkynyl, and —$C_{6-18}$ aryl, which may include the groups of —$NR_2$, —OR, —SR, —OC(O)R, —NHC(O)R, —C(O)OR, —C(O)NHR, —N═$C(N(R^2))_2$, —S(O)R, —$S(O)_2R$, —$S(O)_2NR_2$, —CN, —Cl, —Br, —I, —F, $N_3$, a group of Formula 2 or a group of Formula 3.

4. The compound according to claim 1, wherein $R_1$=$R_3$, $R_2$=$R_4$.

5. The compound according to claim 4, wherein $R_1$=$R_3$=—H or —$CH_3$, $R_2$=$R_4$.

6. The compound according to claim 5, wherein $R_1$=$R_3$=—H or —$CH_3$, $R_2$=$R_4$=—$C_{1-18}$alkyl or —$C_{2-18}$alkenyl.

7. The compound according to claim 1, wherein $R^1$ is absent and $R^2$ is ═C—$(NR_2)_2$, or $R^3$ is absent and $R^4$ is ═C—$(NR_2)_2$.

8. The compound according to claim 1, wherein $R^1$ and $R^2$; $R^3$ and $R^4$; $R^5$ and $R^6$; $R^7$ and $R^8$ together with the atom to which they are bound form a 5-8-membered heterocyclic substituent selected from the group consisting of N-pyrrolidinyl, N-piperidinyl, N-azepanyl, N-azocanyl, or N-piperazinyl.

9. A method for production of a compound according to claim 1 (F0), the method comprising interaction of a trivalent phosphorus derivative of Formula (F1) with an azidotriazine of Formula (F2) to give a compound of Formula (F3), with subsequent processing with amines $HNR^1R^2$, $HNR^3R^4$ or $HNR^XR^Y$, wherein substituents $R^X$ and $R^Y$ will be converted to substituents $R^1$, $R^2$, $R^3$, $R^4$ using conversion reactions known in the art for the respective reactive groups included in $R^X$ and $R^Y$, (F1)

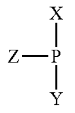

(F2)

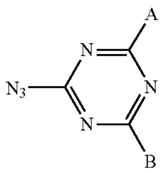

(F3)

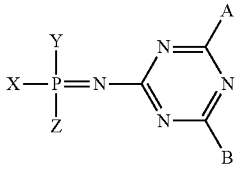

X, Y, Z are defined as in Formula (F0),

A and B may be independently selected from the group consisting of $NR^1R^2$, $NR^3R^4$ or $NR^XR^Y$, -Q, Q is selected from the group consisting of: —OR, —OC(O)R, —$OS(O)_2R$, —CN, —Cl, —Br, —I, —F, —$N_3$, which may be substituted by $NR^1R^2$, $NR^3R^4$ or $NR^XR^Y$ in a reaction with the respective amine $HNR^1R^2$, $HNR^3R^4$ or $HNR^XR^Y$, $R^X$, $R^Y$ are selected from the group consisting of —H, —$C_{1-18}$alkyl, —$C_{2-18}$alkenyl, $C_{2-18}$alkynyl, and —$C_{6-18}$aryl, which may include the groups of —NH—, —N<, —O—, —NHC(O)—, —$NHS(O)_2$, —$N(CH_2CH_2)_2N$—, and terminate in the groups of —$NR_2$, —OR, —SR, —OC(O)R, —NHC(O)R, —C(O)OR, —C(O)NHR, —N═$C(N(R_2))_2$, —S(O)R, —$S(O)_2R$, —$S(O)_2NR_2$, —CN, —Cl, —Br, —I, —F, $N_3$, $R^1$, $R^2$, $R^3$, $R^4$, R are as described in claim 1 (F0).

10. The method according to claim 9, wherein the trivalent phosphorus derivative is an H-phosphonate unit produced according to an H-phosphonate synthesis method, or a phosphite unit produced according to an oligonucleotide phosphoramidite oligonucleotide synthesis method.

11. The method according to claim 10, wherein A=B=-Q.

12. The method according to claim 11, wherein Q=Cl.

13. The method according to claim 10, wherein A=—$NR^1R^2$, B=-Q.

14. The method according to claim 13, wherein Q=Cl.

15. The method according to claim 10, wherein A=—$NR^1R^2$, B=—$NR^3R^4$.

16. An oligonucleotide wherein at least one modified phosphate group is as defined in Formula Fx:

(Fx)

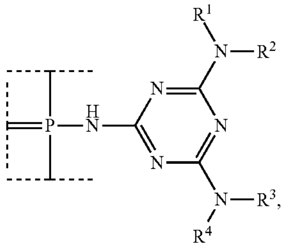

wherein ------ indicates an attachment of substituents respective for the oligonucleotide, and $R^1$, $R^2$, $R^3$, and $R^4$ are as defined in Formula (F0) according to claim 1.

17. A method for exploratory in vitro treatment by administering the oligonucleotide according to claim 16, to a subject in need thereof.

18. A method for exploratory in vivo treatment by administering the oligonucleotide according to claim 16, to a subject in need thereof.

19. A method for diagnostic treatment by administering the oligonucleotide according to claim 16, to a subject in need thereof.

20. A method for therapeutic treatment by administering the oligonucleotide according to claim 16, to a subject in need thereof.

21. A method for treatment of a viral infection by administering the oligonucleotide according to claim 16, to a subject in need thereof.

22. A method for treatment of a microbial infection by administering the oligonucleotide according to claim 16, to a subject in need thereof.

23. A method for treatment of cancer by administering the oligonucleotide according to claim 16, to a subject in need thereof.

24. A method for treatment of cancer via modulating micro-RNA expression by administering the oligonucleotide according to claim 16, to a subject in need thereof.

* * * * *

SEQUENCE LISTING

```
<160> NUMBER OF SEQ ID NOS: 1

<210> SEQ ID NO 1
<211> LENGTH: 132
<212> TYPE: DNA
<213> ORGANISM: Artificial Sequence
<220> FEATURE:
<223> OTHER INFORMATION: model modified oligonucleatides

<400> SEQUENCE: 1

aaatacttca tagtcagaat acttcatagt cagtacatau cctgactatg aagtatctga     60

ctatgaagta ttgggtagca agtcgagatt atactttttt tttttttttt tttttttttt    120

tttttttttt tu                                                        132
```